US010301392B2

(12) United States Patent
Chen et al.

(10) Patent No.: US 10,301,392 B2
(45) Date of Patent: May 28, 2019

(54) METHODS OF INHIBITING T-CELL MEDIATED B-CELL ANTIBODY PRODUCTION USING ANTI-CD27 ANTIBODIES

(71) Applicant: Janssen Biotech, Inc., Horsham, PA (US)

(72) Inventors: John Chen, San Diego, CA (US); Johan Fransson, Toronto (CA); Natalie Fursov, Harleysville, PA (US); Damon Hamel, San Diego, CA (US); Thomas Malia, Philadelphia, PA (US); Galina Obmolova, Phoenixville, PA (US); Tatiana Ort, Plymouth Meeting, PA (US); Michael Rycyzyn, Berwyn, PA (US); Michael Scully, Medford, NJ (US); Raymond Sweet, Bryn Mawr, PA (US); Alexey Teplyakov, Phoenixville, PA (US); John Wheeler, Devon, PA (US); Juan Carlos Almagro, Brookline, MA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 15/596,609

(22) Filed: May 16, 2017

(65) Prior Publication Data

US 2017/0320957 A1  Nov. 9, 2017

Related U.S. Application Data

(62) Division of application No. 14/790,144, filed on Jul. 2, 2015, now Pat. No. 9,683,046, which is a division of application No. 13/835,518, filed on Mar. 15, 2013, now Pat. No. 9,102,737.

(60) Provisional application No. 61/611,332, filed on Mar. 15, 2012.

(51) Int. Cl.
*A61K 39/00*     (2006.01)
*C07K 16/28*    (2006.01)

(52) U.S. Cl.
CPC .... *C07K 16/2878* (2013.01); *A61K 2039/505* (2013.01); *C07K 2317/24* (2013.01); *C07K 2317/34* (2013.01); *C07K 2317/55* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,223,409 A | 6/1993 | Ladner et al. |
| 5,403,484 A | 4/1995 | Ladner et al. |
| 5,427,908 A | 6/1995 | Dower et al. |
| 5,569,825 A | 10/1996 | Lonberg et al. |
| 5,571,698 A | 11/1996 | Ladner et al. |
| 5,573,924 A | 11/1996 | Beckmann et al. |
| 5,580,717 A | 12/1996 | Dower et al. |
| 5,885,793 A | 3/1999 | Griffiths et al. |
| 5,969,108 A | 10/1999 | McCafferty et al. |
| 6,172,197 B1 | 1/2001 | McCafferty et al. |
| 6,300,129 B1 | 10/2001 | Lonberg et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,713,610 B1 | 3/2004 | Kucherlapati et al. |
| 6,982,361 B1 | 1/2006 | Raber et al. |
| 7,119,183 B2 | 10/2006 | Seed et al. |
| 7,148,061 B2 | 12/2006 | Lenardo et al. |
| 2005/0142635 A1 | 6/2005 | Tsuchiya et al. |
| 2007/0014720 A1 | 1/2007 | Gazit-Bornstein et al. |
| 2009/0118127 A1 | 5/2009 | Raghunathan |
| 2010/0173324 A1 | 7/2010 | Mori et al. |
| 2011/0052579 A1 | 3/2011 | Weiss et al. |
| 2011/0217318 A1 | 9/2011 | Takayama et al. |
| 2011/0274685 A1 | 11/2011 | Keler et al. |

(Continued)

FOREIGN PATENT DOCUMENTS

| | | |
|---|---|---|
| WO | WO 90/07861 A1 | 7/1990 |
| WO | WO 02/43478 A2 | 6/2002 |
| WO | WO 03/025019 A1 | 3/2003 |

(Continued)

OTHER PUBLICATIONS

Lynch et al. Preclinical safety evaluation of monoclonal antibodies, in Therapeutic Antibodies. Handbook of Experimental Pharmacology 181, Y. Chernajovsky, A. Nissim (eds.) Springer-Verlag, Berlin, Heidelberg 2008. (Year: 2008).*

Alegre, et al., "A Non-Activating "Humanized" anti-CD3 Monoclonal Antibody Retains Immunosuppressive Properties in Vivo," Transplantation, 57: 1537-1543 (1994).

Almagro, et al., "Humanization of Antibodies," Frontiers in Bioscience, 13: 1619-1633 (2008).

(Continued)

*Primary Examiner* — Elly-Gerald Stoica
(74) *Attorney, Agent, or Firm* — Eric Dichter

(57) ABSTRACT

Human antibodies immunospecific for human CD27 are capable of blocking CD27 binding to its ligand CD70 and neutralizing bioactivity of CD27 including, but not limited to, CD27 intracellular signaling, T-cell proliferation and activation, B-cell proliferation and differentiation, plasmablast formation and alleviation of antibody responses, stimulation of tumor cells by CD70, and the production of soluble mediators from T and B-cells. The antibodies are useful in diagnosing or treating CD27 activity associated diseases and conditions.

5 Claims, 4 Drawing Sheets

Specification includes a Sequence Listing.

(56) References Cited

U.S. PATENT DOCUMENTS

2012/0093805 A1 4/2012 Kubota

FOREIGN PATENT DOCUMENTS

| WO | WO 03/068268 A2 | 8/2003 |
| --- | --- | --- |
| WO | WO 2004/074320 A2 | 9/2004 |
| WO | WO 2008/051424 A2 | 5/2008 |
| WO | WO 2009/085462 A1 | 7/2009 |
| WO | WO 2009/100942 A1 | 8/2009 |
| WO | WO 2011/130434 A2 | 10/2011 |
| WO | WO 2012/004367 A1 | 1/2012 |

OTHER PUBLICATIONS

Angal, et al., "A Single Amino Acid Substitution Abolishes the Heterogeneity of Chimeric Mouse/Human (IgG4) Antibody," Molecular Immunology, 30(1): 105-108 (1993).

Bird, et al., "Single-Chain Antigen-Binding Proteins," Science, 242: 423-426 (1988).

Borst, et al., "CD27 and CD70 in T Cell and B Cell Activation," Current Opinion in Immunology, 17: 275-281 (2005).

Brüggemann, et al., "Production of human antibody repertoires in transgenic mice," Current Opinion in Biotechnology, 8: 455-458 (1997).

Brüggemann, et al., "Human antibody production in transgenic mice: expression from 100 kb of the human IgH locus," European Journal of Immunology, 21: 1323-1326 (1991).

Brugnoni, et al., "CD70 expression on T-cell subpopulations: study of normal individuals and patients with chronic immune activation," Immunology Letters, 55: 99-104 (1997).

Camerini, et al., "The T Cell Activation Antigen CD27 is a Member of the Nerve Growth Factor/Tumor Necorsis Factor Receptor Gene Family," The Journal of Immunology, 147: 3165-3169 (1991).

Ramakrishna, et al., "In Vitro Characterization of Novel Anti-Human CD27 (TNFRSF7) mAbs," Celldex therapeutics Poster, 97th Annual Meeting of AAI Immunology, Baltimore, MD (2010).

Francis Ka-Ming Chan, "Three is better than one: Pre-ligand receptor assembly in the regulation of TNF Receptor Signaling," Cytokine, 37: 101-107 (2007).

Francis Ka-Ming Chan, "A Domain in TNF Receptors that mediates Ligand-Independent Receptor Assembly and Signaling," Science, 228: 2351-2354 (2000).

Chothia, et al.., "Canonical Structures for the Hypervariable Regions of Immunoglobulins," Journal of Molecular Biology, 196: 901-917 (1987).

Co, et al., "Chimeric and Humanized Antibodies with Specificity for the CD33 Antigen," The Journal of Immunology, 148 (4): 1149-1154 (1992).

Michael Croft, "Costimulation of T cells by OX40, 4-1BB, and CD27," Cytokine & Growth Factor Reviews, 14: 265-273 (2003).

Guo-Min Deng, "Tumor Necrosis Factor Receptor Pre-Ligand Assembly Domain is an Important Therapeutic Target in Inflammatory Arthritis," Biodrugs, 21(1): 23-29 (2007).

de Wildt, et al., "Analysis of Heavy and Light Chain Pairings Indicates that Receptor Editing Shapes the Human Antibody Repertoire," Journal of Molecular Biology, 285: 895-901 (1999).

Dörner, et al., "Correlation of circulating CD27 high plasma cells and disease activity in systemic lupus erythematosus," Lupus, 13: 283-289 (2004).

Drachman, et al., "SGN-70: Phase la Study of a Novel Humanized Antibody Targeting CD70 for the Treatment of Autoimmune Diseases," Arthritis & Rheumatism, 62 Suppl 10: 1273 (2010) (Abstract).

Erlichman, et al., "CD27 Signals Through PKC in Human B Cell Lymphomas," Cytokine, 11(7): 476-484 (1999).

Fazekas, et al., "Production of Monoclonal Antibodies: Strategy and Tactics," Journal of Immunological Methods, 35: 1-21 (1980).

Fishwild, et al., "High-avidity human IgGκ monoclonal antibodies from a novel strain of minilocus transgenic mice," Nature Biotechnology, 14: 845-851 (1996).

Fransson, et al., "Human Framework Adaptation of a Mouse Anti-Human IL-13 Antibody," Journal of Molecular Biology, 398: 214-231 (2010).

French, et al., "Eradication of lymphoma by CD8 T cells following anti-CD40 monoclonal antibody therapy is critically dependent on CD27 costimulation," Blood, 109: 4810-4815 (2007).

GenBank Accession No. NP_001233, Dated Nov. 17, 2013.

GenBank Accession No. NP_001243, Dated Sep. 22, 2013.

GenBank Accession No. NP_006418, Dated Aug. 12, 2013.

GenBank Accession No. NP_068355, dated Aug. 12, 2013.

Gravestein, et al., "Novel mAbs reveal potent co-stimulatory activity of murine CD27," International Immunology, 7(4): 551-557 (1995).

Green, et al., "Antibody engineering Via genetic engineering of the mouse: XenoMouse strains are a vehicle for the facile generation of therapeutic human monoclonal antibodies," Journal of Immunological Methods, 231: 11-23 (1999).

Green, et al., "Regulation of B Cell Development by Variable Gene Complexisity in Mice Reconstituted with Human Immunologlobulin Yeast Artificial Chromosomes," Journal of Experimental Medicine, 188(3): 483-495 (1998).

Green, et al., "Antigen-specific human monoclonal antibodies from mice engineered with human Ig heavy and light chain YACs," Nature Genetics, 7: 13-21 (1994).

Hendriks, et al., "CD27 is required for generation and long-term maintenance of T cell immunity," Nature Immunology, 1(5): 433-440 (2000).

Henikoff, et al., "Amino acid substitution matrices from protein blocks," Proceedings of the National Academy of Science USA, 89: 10915-10919 (1992).

Hintzen, et al., "Elevated levels of a soluble forms of the T cell activation antigen CD27 in cerebrospinal fluid of multiple sclerosis patients," Journal of Neuroimmunology, 35: 211-217 (1991).

Hoogenboom, et al., "By-passing Immunisation Human Antibodies from Synthetic Repertoires of Germline $V_H$ Gene Segments Rearranged in Vitro," Journal of Molecular Biology, 227: 381-388 (1992).

Huston, et al., "Protein engineering of antibody binding sites: Recovery of specific activity in an anti-digoxin single-chain Fv analogue products in *Escherichia coli*," Proceedings of the National Academy of Science USA, 85: 5879-5883 (1988).

Jacobs, et al., "Cross-Interaction Chromatography: A Rapid Method to Identify Highly Soluble Monoclonal Antibody Candidates," Pharmaceutical Research, 27(1): 65-71 (2010).

Serge Jacquot, et al., "CD27/CD70 Interactions Regulate T Dependent B Cell Differentiation," Immunologic Research, 21(1): 23-30 (2000).

Kaas, et al., "IMGT/3Dstructure-DB and IMGT/StmcturalQuery, a database and a toll for immunoglobulin, T cell receptor and MHC structural data," Nucleic Acids Research, 32: D208-D210 (2004).

Kobata, et al., "CD27-CD70 interactions regulate B-cell activation by T Cells," Proceedings of the National Academy of Science USA, 92: 11249-11253 (1995).

Knappik, et al., "Fully Synthetic Human Combinatorial Antibody Libraries (HuCAL) Based on Modular Consensus Frameworks and CDRs Randomized with Trinucleotides," Journal of Molecular Biology, 296: 57-86 (2000).

LeFranc, et al., IMGT, the international ImMunoGeneTics information system®, Nucleic Acids Research, 33: D593-D597 (2005).

Lonberg, et al., "Antigen-specific human antibodies from mice comprising four distinct genetic modifications," Nature, 368: 856-859 (1994).

Lonberg, et al., "Human Antibodies from Transgenic Mice," International Review of Immunology, 13: 65-93 (1995).

Manz, et al., "Renaissance for mouse models of human hematopoiesis and immunobiology," Nature Immunology, 10: 1039-1042 (2009).

Marks, et al., "By-Passing Immunization Human Antibodies from V-gene Libraries Displayed on Phage," Journal of Molecular Biology, 222: 581-597 (1991).

Mendez, et al., "Functional transplant of megabase human immunoglobulin loci recapitulates human antibody response in mice," Nature Genetic, 15: 146-156 (1997).

(56) References Cited

OTHER PUBLICATIONS

Oekle, et al., "Overexpression of CD70 and Overstimulation of IgF Synthesis by Lupus T Cells and T Cells Treated with DNA Methylation Inhibitors," Arthritis & Rheumatism, 50 (6): 1850-1860 (2004).
Queen, et al., "A humanized antibody that binds to the interleukin 2 receptor," Proceedings of the National Academy of Science USA, 86: 10029-10033 (1989).
Raman, et al., "Ligation of CD27 on B Cells In Vivo during Primary Immunization Enhances Commitment to memory B Cell Responses," The Journal of Immunology, 171: 5876-5881 (2003).
Sakanishi, et al., "Biochemical and Biophysical Research Communication," Biochemical and Biophysical Research Communications, 393: 829-835 (2010).
Sali, et al., "Comparative Protein Modelling by Satisfaction of Spatial Restraints," Journal of Molecular Biology, 234: 779-815 (1993).
Sheets, et al., "Efficient construction of a largenonimmune phage antibody library: The production of high-affinity human single-chain antibodies to protein antigens," Proceedings of the National Academy of Science USA, 95: 6157-6162 (1998).
Shi, et al., "De Novo Selection of High-Affinity Antibodies from Synthetic Fab Libraries Displayed on Phage as pIX Fusion Proteins," Journal of Molecular Biology, 397: 385-396 (2010).
Sugita, et al., "The 1A4 Molecule (CD27) is Involved in T Cell Activation," The Journal of Immunology, 147: 1477-1483 (1991).
Tak, et al., "Expression of the Activation Antigen CD27 in Rheumatoid Arthritis," Clinical Immunology and Immunopathology, 80 (2): 129-138 (1996).
Tornetta, et al., "Antibody Fab display and selection through fusion to the pIX coat protein of filamentous phage," Journal of Immunological Methods, 360: 39-46 (2010).
Vaughn, et al., "Human Antibodies with Sub-nanomolar Affinities Isolated from a Large Non-immunized Phage Display Library," Nature Biotechnology, 14: 309-314 (1996).
Ward, et al., "Binding activities of a repertoire of single immunoglobulin variable domains secreted from *Escherichia coli*," Nature, 341: 544-546 (1989).
Wu, et al., "An Analysis of the Sequences of the Variable Regions of Bence Jones Proteins and Myeloma Light Chains and Their Implications for Anti-Body Complementarity," Journal of Experimental Medicine, 132: 211-250 (1970).
Yamamoto, et al., "NF-κB Activation in CD27 Signaling: Involvement of TNF Receptor-Associated Factors in Its Signaling and Identification of Functional Region of CD27," Journal of Immunology, 161: 4753-4759 (1998).
Yang, et al., "Eradication of Established Tumors by a Fully Human Monoclonal Antibody to the Epidermal Growth Factor Receptor without Concomitant hemotherapy," Cancer Research, 59: 1236-1243 (1999).

* cited by examiner

METHODS OF INHIBITING T-CELL MEDIATED B-CELL ANTIBODY PRODUCTION USING ANTI-CD27 ANTIBODIES

CROSS-REFERENCE TO RELATED APPLICATIONS

This application is a divisional of U.S. application Ser. No. 14/790,144, filed 2 Jul. 2015, now U.S. Pat. No. 9,683,046, issued 20 Jun. 2017, which is a divisional of U.S. application Ser. No. 13/835,518, filed 15 Mar. 2013, now U.S. Pat. No. 9,102,737, issued 11 Aug. 2015, which claims the benefit of U.S. Provisional Application Ser. No. 61/611,332, filed 15 Mar. 2012, the entire contents of which are incorporated herein by reference in their entireties.

BACKGROUND OF THE INVENTION

Field of the Invention

The present invention relates to human antibodies to the CD27 protein and their uses and, more particularly, human antibodies to human CD27 protein and their use in treating inflammatory disorders.

Related Art

CD27 is a type I transmembrane protein and member of the TNF receptor superfamily (TNFSF27) expressed as a surface antigen on a majority of T cells, natural killer cells and antibody secreting plasma and memory B-cells. CD70 is a cytokine, also called tumor necrosis factor ligand superfamily member 7 (TNFSF7), and the cognate ligand for CD27. TNFSF ligand-receptor interactions are able to regulate T-dependent B-cell differentiation (Jacquot S. 2000 Immunol Res. 21(1):23-30) and induce apoptotic cell death in different cells.

CD27:CD70 ligation results in activation of canonical and non-canonical NF-kβ signaling pathways that in turn stimulates B- and T-cell proliferation, plasma cell differentiation and subsequent antibody secretion (Yamamoto, H. 1998 J Immunol. 161(9): 4753-9). CD27 co-stimulation with OX40, 4-1BB also promotes the survival of activated T cells (Croft, M. 2003 Cytokine Growth Factor Rev. 14(3-4): 265-73), thereby regulating a number of effector and memory T cells and controls T cell function directly by promoting production of cytokines, such as IL-4 and IFNgamma, or modulating T-cell responses to the actions of other cytokines, such as IL2 and IL-12.

Studies in both humans and animals suggest an important role of the CD27:CD70 pathway in various immune-related diseases, including systemic lupus erythematosus (SLE) (Doerner T Lupus 2004 13(5):283-9), rheumatoid arthritis (Tak, P P et al. 1996 clin Immunol Immunopathol 80(2): 129-38) and multiple sclerosis (Hintzen R Q et al. 1991 J Neuroimmunol 35(1-3):211-7). On the other hand, CD70 has been reported to be expressed to varying degrees on malignant B cells and the CD70:CD27 complex is able to mediate an antitumor response by activating antitumor immunity and reducing tumor growth (Borst J, Hendriks J and Xiao Y. 2005. Curr Opin Immunol. 17(3):275-81). CD27 may also control the accumulation of CD4+ and CD8+ T-cells at sites of infection (Hendricks et al. 2000 Nature Immunol 1, 433-440).

CD70 is not expressed on normal non-hematopoietic cells. CD70 expression appears to be temporally restricted to antigen-activated T- and B cells and its expression is down-regulated when antigenic stimulation ceases. Evidence from animal models suggests that CD70 may contribute to immunological disorders such as, e.g., rheumatoid arthritis (Brugnoni et al., 1997 Immunol. Lett. 55:99-104), psoriatic arthritis (Brugnoni et al., 1997, Immunol. Lett. 55:99-104), and lupus (Oelke et al., 2004, Arthritis Rheum. 50:1850-60). In addition to its potential role in inflammatory responses, CD70 is also expressed on a variety of transformed cells including lymphoma B cells, Hodgkin's and Reed-Sternberg cells, malignant cells of neural origin, and a number of carcinomas.

Agonist CD27 binding antibodies described in WO2008/051424 (Univ. South Hampton) are noted as useful for promoting T-cell immunity and such antibodies have a binding epitope which causes them to be unaffected (not inhibited) by CD70.

While studies in rodents involving alteration of CD27 and/or CD70 have demonstrated potentially important roles of this receptor ligand interaction, there is a need to provide human antibodies specific for human CD27 and other CD27:CD70 interaction blocking agents that can exert a clinically useful cytotoxic, cytostatic, or immunomodulatory effect on CD27-expressing cells, particularly without exerting undesirable agonist effects on CD27-expressing cells in the absence of CD70. Such compounds may be useful therapeutic agents in modulating the development of neoplastic cells or immune disorders that are mediated by CD27-expressing cells.

SUMMARY OF THE INVENTION

The present invention provides human CD27 binding, monoclonal antibodies capable of blocking activities associated with CD27-CD70 interaction on cells, tissues, or organs in a host subject. Amino acid sequences of exemplary CD27 binding monoclonal antibodies are provided which are encoded by nucleic acids for expression in a host cell. In addition, the CD27 monoclonal antibodies of the invention define at least three non-overlapping epitopes on the extracellular domain of CD27 which when engaged by an antibody of the invention, are prevented from CD70-type ligand ligation driven signaling and downstream biological activity.

Another aspect of the invention is an isolated anti-CD27 antibody reactive with a CD27 protein epitope defined by residues between positions 21-191 of the CD27 protein.

Another aspect of the invention is an isolated antibody having a heavy chain variable region sequence selected from the sequences shown in SEQ ID NOs: 76, 78, 80, 102-126, 128-136, and 145-147, and a light chain variable region sequence selected from the sequences shown in SEQ ID NOs: 77, 79, 81-101, 127, 137-144, and 148, including variants of those sequences, e.g., conservative substitutions.

A further aspect of the invention is an isolated antibody having heavy and light chain CDR sequences selected from the sequences shown in SEQ ID NOs: 1-75 and 151-158, including variants of those sequences, e.g., conservative substitutions.

Another aspect of the invention is an isolated polynucleotide encoding an antibody of the invention.

In another aspect, the invention relates to an antibody which binds to a common epitope defined by the region on the protein to which antibodies C2177 and/or C2186 or human antibodies generated therefrom described in Tables 30-39 bind or which compete for binding to the CD27 protein with antibodies C2177 and/or C2186 or human antibodies generated therefrom described in Tables 30-39. In another embodiment, the invention relates to an antibody which binds to an epitope of the extracellular domain of CD27 defined by the region on the protein to which antibody C2191 bind or human antibodies generated therefrom described in Tables 30-39 and competes for binding to the CD27 protein with antibody C2191 or human antibodies generated therefrom described in Tables 30-39. In another embodiment, invention relates to an antibody which binds to an epitope of the extracellular domain of CD27 defined by the region on the protein to which antibody C2192 binds or human antibodies generated therefrom described in Tables 30-39 and competes for binding to the CD27 protein with antibody C2192 or human antibodies generated therefrom described in Tables 30-39. In another aspect, the invention comprises an antibody or fragment thereof derived from one or more of antibodies C2177, C2186, C2191, and C2192 or human antibodies generated therefrom described in Tables 30-39 having other functional binding characteristics exhibited by one or more of antibodies C2177, C2186, C2191, and C2192, or human antibodies generated therefrom described in Tables 30-39, such as inhibiting the binding of CD27 to CD70 positive cells.

Thus, one aspect of the invention relates to an engineered antibody comprising an engineered (e.g., humanized or human adapted) heavy chain and light chain, wherein:
(1) the engineered heavy chain variable region comprises or is derived from one or more complementarity determining regions (CDRS) from the mouse antibodies C2177, C2191, C2192 and C2186 heavy chain and a framework from a human acceptor antibody heavy chain, optionally having one or more human framework residue substitutions, and
(2) the engineered light chain variable region comprises one or more complementarity determining regions from the mouse antibodies C2177, C2191, C2192 and C2186 light chain and a framework from a human acceptor antibody light chain optionally having one or more human framework residue substitutions; and
(3) the engineered antibody specifically binds to human CD27 and interferes with its interaction with CD70.

In a further embodiment, the engineered antibody may be composed of one or more CDRs that are further engineered with one or more substitutions or deletions, for example, those that are 90%, 95%, 98% or 99.5% identical to one or more CDRs of antibodies C2177, C2191, C2192 and/or C2186.

Another embodiment relates to the treatment or prevention of pathological conditions associated with CD27 bioactivity by administering a therapeutically or prophylactically effective amount of an antibody of the present invention, portion thereof or a mixture of antibodies of the present invention or portions thereof to a subject in need of such treatment.

In a further embodiment, the invention comprises antigen epitopes as a component of a vaccine. The polypeptides or polynucleotides encoding the polypeptide epitopes described above comprising subfragments or three-dimensional analogs of some or all of SEQ ID NO: 1 residues 21-191, or conservative changes thereof, are recognized by the antibodies of the invention. The polypeptides and polynucleotides are useful for actively immunizing a host to elicit production of antibodies against CD27 capable of the combating or preventing pathological conditions associated with CD27 bioactivity.

The invention also relates to methods of generating, purifying, formulating, and packaging an antibody of the invention for use in the treatment or prevention of pathological conditions associated with CD27 bioactivity by administering a therapeutically or prophylactically effective amount of an antibody or portion thereof.

DETAILED DESCRIPTION

Abbreviations

Figure 1:
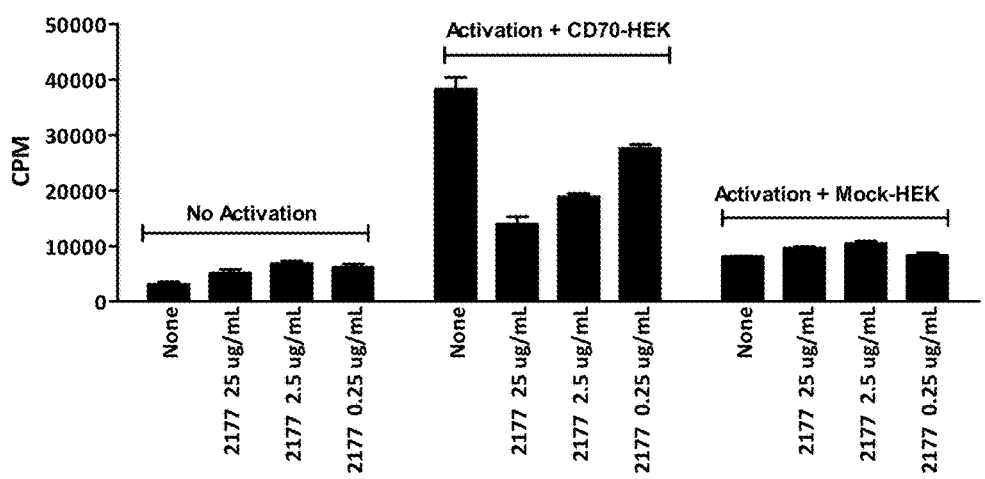
FIG. 1 is a graph showing the effects of the C2177 antibody on T-cell proliferation.

CDR—complementarity determining region; CFSE—carboxyfluorescein diacetate, succinimidyl ester; ECD—extracellular domain; FR—framework; H—heavy chain; GvHD graft-versus-host disease; L—light chain; IFN—interferon (g, gamma); Ig—immunoglobulin; Mab—monoclonal antibody; MMP—matrix metalloproteinase; PBMC—peripheral blood mononuclear cells; VL—Variable light chain; VH—Variable heavy chain Definitions As used herein, an "antibody" includes whole antibodies and any antigen binding fragment or a single chain thereof. Thus, the antibody includes any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, which can be incorporated into an antibody of the present invention. The term "antibody" is further intended to encompass antibodies, digestion fragments, specified portions and variants thereof, including antibody mimetics or comprising portions of antibodies that mimic the structure and/or function of an antibody or a specified fragment or portion thereof, including single chain and single domain antibodies and fragments thereof. Functional fragments include antigen-binding fragments to a preselected target. Examples of binding fragments encompassed within the term "antigen binding portion" of an antibody include (i) a Fab fragment, a monovalent fragment consisting of the VL, VH, CL and CH, domains; (ii) a F(ab')2 fragment, a bivalent fragment comprising two Fab fragments linked by a disulfide bridge at the hinge region; (iii) a Fd fragment consisting of the VH and CH, domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (I 988) Science 242:423-426, and Huston et al. (1988) Proc. Natl. Acad Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Conversely, libraries of scFv constructs can be used to screen for antigen binding capability and then, using conventional techniques, spliced to other DNA encoding human germline gene sequences. One example of such a library is the "HuCAL: Human Combinatorial Antibody Library" (Knappik, A. et al. J Mol Biol (2000) 296(1):57-86).

The term "CDR" refers to the complementarity determining region or hypervariable region amino acid residues of an antibody that participate in or are responsible for antigen-binding. The hypervariable region or CDRs of the human IgG subtype of antibody comprise amino acid residues from residues 24-34 (L1), 50-56 (L2) and 89-97 (L3) in the light chain variable domain and 31-35 (H1), 50-65 (H2) and 95-102 (H3) in the heavy chain variable domain as described by Kabat et al. (1991 Sequences of Proteins of Immunological Interest, 5th Ed. Public Health Service, National Institutes of Health, Bethesda, Md.) and/or those residues from a hypervariable loop (i.e., residues 26-32 (L1), 50-52 (L2) and 91-96 (L3) in the light chain variable domain and 26-32 (H1), 53-55 (H2) or the current H2 Chothia definition of 52-57, and 96-101 (H3) in the heavy chain variable domain as described by (Chothia et al., J. Mol. Biol. 196: 901-917 (1987)).

Framework or FR1-4 residues are those variable domain residues other than and bracketing the hypervariable regions. More recently, a universal numbering system has been developed and widely adopted, international ImMunoGeneTics information System® (IMGT) (LaFranc, et al. 2005. Nucl Acids Res. 33:D593-D597).

Herein, the CDRs are referred to in terms of both the amino acid sequence and the location within the light or heavy chain by sequential numbering. As the "location" of the CDRs within the structure of the immunoglobulin variable domain is conserved between species and present in structures called loops, by using numbering systems that align variable domain sequences according to structural features, CDR and framework residues and are readily identified. This information is used in grafting and replacement of CDR residues from immunoglobulins of one species into an acceptor framework from, typically, a human antibody.

The term "CD27" refers to the human TNF receptor superfamily (TNFSF27), the product of the human gene 939 (CD27 gene), also called human CD27L receptor, MGC20393, S152, T14, T-cell activation antigen CD27 and include all of the variants, isoforms and species homologs of CD27. The expressed human CD27 (NCBI Accession No. NP 001233) is a polypeptide of 260 amino acids in length having a 20 amino acid secretion signal at the N-terminus. Accordingly, the antibodies of the invention may, in certain cases, cross-react with CD27 from species other than human. In other cases, the antibodies may be completely specific for human CD27 and not exhibit species or other types of cross-reactivity. By CD27 biological activities is meant, any downstream activities resulting from CD27 receptor binding and/or activation as a result of activation of CD27 by one or more ligands, especially CD70 polypeptides (TNFSF7, NP_001243), or other ligands, such as SIVA. CD27 transduces signals that lead to the activation of NF-κ-β and MAPK8/JNK. Adaptor proteins TRAF2 and TRAF5 have been shown to mediate the signaling process of this receptor. CD27 biologic activities may also result from the binding of certain truncated forms of CD27 or fragments of CD27 to ligands which themselves exhibit biologic activities, for example, a polypeptide which comprises from about residues 21-191 of the full-length protein can bind to CD70. The CD27 antigen cytoplasmic tail, residues 213-260, binds to the N-terminus of the SIVA protein (also known as the apoptosis-inducing factor: CD27BP; SIVA1, Siva-1, NP_006418 (175 aa)); and Siva-2, SIVA2, NP_068355 (110 aa).

The term "epitope" means a protein determinant capable of specific binding to an antibody. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents.

"Humanization" (also called Reshaping or CDR-grafting) or "engineering" includes established techniques for reducing the immunogenicity of monoclonal antibodies (mAbs) from xenogeneic sources (commonly rodent) and for improving affinity or the effector functions (ADCC, complement activation, C1q binding). The engineered mAb can be produced using the techniques of molecular biology, using phage displayed randomized sequences, or synthesized de novo. For example, in order to construct a humanized antibody with incorporated CDR regions from a nonhuman species, the design might include variations, such as conservative amino acid substitutions in residues of the CDRs, and back substitution of residues from the nonhuman mAb into the human framework regions (backmutations). The positions can be discerned or identified by sequence comparison methods, consensus sequence analysis, or structural analysis of the variable regions' 3D structure. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way or by simple sequence alignment algorithms (e.g., Clustal W), FR (framework) residues can be selected from known antibody sequences, found in such publicly accessible databases as VBASE or Kabat, and the consensus sequences optimized so that the desired antibody characteristic, such as affinity for the target antigen(s), is achieved. As the datasets of known parameters for antibody structures increases, so does the sophistication and refinement of these techniques. Another approach to humanization is to modify only surface residues of the rodent sequence with the most common residues found in human mAbs and has been termed "resurfacing" or "veneering." A large number of both human and non-human Ig sequences are now known and freely available and used by those skilled in the art, e.g., the database and tools developed by LeFranc et al found under the name IMGT; websites curated by the U.S. National Center for Biologics (NCBI); Kabat et al., Sequences of Proteins of Immunological Interest, U.S. Dept. Health (1983) now also greatly expanded and available online, each entirely incorporated herein by reference. Humanization or engineering of antibodies of the present invention can be performed using any method known or those developed using human immunoglobulin sequence information. Such methods are taught in, for example, Winter U.S. Pat. No. 6,982,361 and Bowdish et al. WO03/025019, the contents of which are incorporated herein by reference.

As used herein, $K_D$ refers to the dissociation constant, specifically, the antibody $K_D$ for a predetermined antigen, and is a measure of affinity of the antibody for a specific target. High affinity antibodies have a $K_D$ of $10^{-8}$ M or less, more preferably $10^{-9}$ M or less and even more preferably $10^{-10}$ M or less, for a predetermined antigen. The reciprocal of $K_D$ is $K_A$, the association constant. The term "$k_{dis}$" or "$k_2$," or "$k_d$" as used herein, is intended to refer to the dissociation rate of a particular antibody-antigen interaction. The "$K_D$" is the ratio of the rate of dissociation ($k_2$), also called the "off-rate ($k_{off}$)" to the rate of association rate ($k_1$) or "on-rate ($k_{on}$)." Thus, $K_D$ equals $k_2/k_1$ or $k_{off}/k_{on}$, and is expressed as a molar concentration (M). It follows that the smaller the $K_D$, the stronger the binding. Thus, a $K_D$ of $10^{-6}$ M (or 1 microM) indicates weak binding compared to $10^{-9}$ M (or 1 nM). These values may be calculated using surface plasmon resonance and/or the Kinexa method as known in the art.

The terms "monoclonal antibody" or "monoclonal antibody composition" as used herein refer to a preparation of antibody molecules of single molecular composition. A monoclonal antibody composition displays a single binding specificity and affinity for a particular epitope. The term also includes "recombinant antibody" and "recombinant monoclonal antibody" as all antibodies are prepared, expressed, created or isolated by recombinant means, such as (a) antibodies isolated from an animal or a hybridoma prepared by the fusion of antibody secreting animal cells and an fusion partner, (b) antibodies isolated from a host cell transformed to express the antibody, e.g., from a transfectoma, (c) antibodies isolated from a recombinant, combinatorial human or other species antibody library, and (d) antibodies prepared, expressed, created or isolated by any other means that involve splicing of immunoglobulin gene sequences to other DNA sequences. An "isolated antibody," as used herein, is intended to refer to an antibody which is substantially free of other antibodies having different antigenic specificities. An isolated antibody that specifically binds to an epitope, isoform or variant of human CD27 may, however, have cross-reactivity to other related antigens, e.g., from other species (e.g., CD27 species homologs). Moreover, an isolated antibody may be substantially free of other cellular material and/or chemicals. In one embodiment of the invention, a combination of "isolated" monoclonal antibodies having different specificities are combined in a well defined composition.

As used herein, "specific binding," "immunospecific binding" and "binds immunospecifically" refers to antibody binding to a predetermined antigen. Typically, the antibody binds with a dissociation constant ($K_D$) of $10^{-7}$ M or less, and binds to the predetermined antigen with a $K_D$ that is at least twofold less than its $K_D$ for binding to a non-specific antigen (e.g., BSA, casein, or any other specified polypeptide) other than the predetermined antigen. The phrases "an antibody recognizing an antigen" and "an antibody specific for an antigen" are used interchangeably herein with the term "an antibody which binds specifically to an antigen." As used herein "highly specific" binding means that the relative $K_D$ of the antibody for the specific target epitope is at least 10-fold less than the $K_D$ for binding that antibody to other ligands.

As used herein, "isotype" refers to the antibody class (e.g., IgM or IgG) that is encoded by heavy chain constant region genes. Some antibody classes further encompass subclasses which are also encoded by the heavy chain constant regions and further decorated by oligosaccharides at specific residues within the constant region domains (e.g. IgG1, IgG2, IgG3 and IgG4) which further impart biological functions to the antibody. For example, in human antibody isotypes IgG1, IgG3 and to a lesser extent, IgG2 display effector functions as do murine IgG2a antibodies.

By "effector" functions or "effector positive" is meant that the antibody comprises domains distinct from the antigen specific binding domains capable of interacting with receptors or other blood components such as complement, leading to, for example, the recruitment of macrophages and events leading to destruction of cells bound by the antigen binding domains of the antibody. Antibodies have several effector functions mediated by binding of effector molecules. For example, binding of the C1 component of complement to antibodies activates the complement system. Activation of complement is important in the opsonisation and lysis of cell pathogens. The activation of complement stimulates the inflammatory response and may also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

1. Composition of an Antibody of the Invention

A CD27-neutralizing antibody of the invention is an antibody that inhibits, blocks, or interferes with at least one CD27 activity or CD70 binding, in vitro, in situ and/or in vivo and does not promote, stimulate, induce, or agonize CD27 activity or ligand binding nor does antibody binding mimic the downstream effects of CD27-ligand ligation, in particular CD70 interaction with CD27, such as signal transduction in a host cell. A suitable CD27-neutralizing antibody, specified portion, or variant can also, optionally, affect at least one CD27 activity or function, such as but not limited to, RNA, DNA or protein synthesis, protein release, T-cell activation, B-cell proliferation or differentiation, antibody secretion, CD27 receptor signaling, CD27 cleavage, CD27-ligand binding, CD27 or CD70 induction, synthesis or secretion.

In relation to the CD27:CD70 co-stimulatory pathway blocking activity of the CD27-neutralizing antibodies of the present invention, the treatment of autoimmune disorders with elevated T- or B-cell effector functions may be beneficial.

The present invention is based upon the discovery of anti-human CD27 monoclonal antibodies capable of inhibiting CD27 activation by CD70 and incapable of CD27 self-activation in the absence of CD70 stimulus. Hybridomas and transfectomas capable of secreting such an antibody were generated. An NF-kβ reporter gene assay was used to identify several candidate antibodies capable of inhibiting CD70-mediated NF-kβ reporter activation of CD27 expressing host cells. Second, the antibodies were characterized as being unable to induce dose-dependent agonistic activity when incubated with CD27 coupled luciferase reporter transfected cells in the absence of CD70 stimulus. Third, it was demonstrated that the antibodies dose-dependently inhibit CD70-dependent human naïve CD4 T-cell proliferation. Fourth, the CD27-neutralizing antibodies generated are capable of reducing CD70-mediated stimulation of plasma cell generation from human primary B-cells in a dose dependent manner. Fifth, no significant dose-dependent agonistic activity was observed in primary T- or B-cells with tested anti-CD27 antibodies.

The antibodies of the invention can interfere with CD27:CD70 ligation, inhibit both T-cell effector functions and B-cell differentiation to plasma cells in cell culture and thus may be beneficial for treatment of immune-mediated diseases including, but not limited to, rheumatoid arthritis, systemic lupus erythematosus, multiple sclerosis, inflammatory bowel disease, Crohn's Disease, chronic obstructive pulmonary disease or other syndrome, pathology, disease or disorder related to the aberrant functions or activation of CD27-expressing cell populations. The CD27-binding antibodies described herein recognize at least three distinct regions on the extracellular domain of human CD27, indicating the additional discovery of multiple sites on CD27 suitable for the targeting of antibodies or other compounds with similar function blocking capabilities. Thus, expression and purification of the antibody binding domains provided herein as amino acid sequences further provides a tool which can be the means for selection of novel molecules exhibiting CD27-neutralizing activity.

In one embodiment, the anti-human CD27 antibody, has a binding region comprising a light chain variable (VL) or heavy chain variable (VH) region having the amino acid sequence as shown in SEQ ID NO: 76-144 and which antibody or binding portion thereof immunospecifically binds CD27. In another embodiment of the invention, the antibody or antigen binding portion thereof, binds to CD27 protein and, in addition, the antibodies possesses specified functional properties of antibodies of the invention, such as:
binding to immobilized human CD27;
inhibition of human soluble CD27 binding to cells expressing CD70;
inhibition of human CD70 mediated CD27 signaling measured by NF-kappaB reporter gene assay at an IC50 of less than 0.5 ug/ml;
inhibition of CD70-mediated proliferation of naïve T-cells;
inhibition of CD70 mediated plasma blast formation from primary human B-cells;
inhibition of human CD70-mediated soluble mediator release from T and B primary cells or cell lines;
binding to human CD27 with $K_d$ of less than 100 nM ($10^{-7}$ M);
minimal activation of CD27 signaling in the absence of CD70 stimulus; and
binding to an epitope on the human CD27 extracellular domain to which the Mabs having one or more of the variable region sequences of SEQ ID NOS: 76-144 bind and competes for binding with the Mabs identified having one or more of the variable region sequences of SEQ ID NOS: 76-144.

Since it is well known in the art that antibody heavy and light chains CDR domains play a particularly important role in the binding specificity/affinity of an antibody for an antigen, the recombinant antibodies of the invention disclosed herein preferably comprise one or more of the heavy and light chain CDRs of SEQ ID NOS: 1-75. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

In one embodiment, the human antibodies of the invention have the sequence of one or more of the heavy and light chain CDRs of SEQ ID NOS: 1-75. In addition to these CDR sequences, the ordinarily skilled artisan will appreciate that some deviation from the exact CDR sequences may be possible or desirable while still retaining the ability of the antibody to bind CD27 (e.g., conservative substitutions). Accordingly, in another embodiment, the human antibody may be composed of one or more CDRs that are, for example, 90%, 95%, 98% or 99.5% identical to the CDRs listed in SEQ ID NOs: 1-75.

In another embodiment, the epitope bound by the antibodies of the invention, comprising as few as five to all of residues 21-191 of CD27 protein or a nucleic acid coding sequence therefor, can be used to immunize a subject in order to produce the antibodies of the invention directly in the host for the purpose of treating, preventing, or ameliorating disease or symptoms of disease associated with the production of CD27.

2. Generation of CD27-Neutralizing Antibodies

A CD27-neutralizing antibody exhibiting the desired bioactivity spectrum as exemplified herein by the disclosed and described antibodies, can be generated by a variety of techniques, including the standard somatic cell hybridization technique (hybridoma method) of Kohler and Milstein (1975) Nature 256:495. In the hybridoma method, a mouse or other appropriate host animal, such as a hamster or macaque monkey, is immunized as described herein to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

A CD27-neutralizing antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-CD27 antibody can be isolated from such animals and immortalized using suitable methods, such as the methods described herein. Alternatively, the antibody coding sequences may be cloned, introduced into a suitable vector, and used to transfect a host cell for expression and isolation of the antibody by methods taught herein and those known in the art.

The use of transgenic mice carrying human immunoglobulin (Ig) loci in their germline configuration provides for the isolation of high affinity fully human monoclonal antibodies directed against a variety of targets including human self antigens for which the normal human immune system is tolerant (Lonberg, N. et al., U.S. Pat. Nos. 5,569, 825, 6,300,129 and 1994, Nature 368:856-9; Green, L. et al., 1994, Nature Genet. 7:13-21; Green, L. & Jakobovits, 1998, Exp. Med. 188:483-95; Lonberg, N and Huszar, D., 1995, Int. Rev. Immunol. 13:65-93; Kucherlapati, et al. U.S. Pat. No. 6,713,610; Bruggemann, M. et al., 1991, Eur. J. Immunol. 21:1323-1326; Fishwild, D. et al., 1996, Nat. Biotechnol. 14:845-851; Mendez, M. et al., 1997, Nat. Genet. 15:146-156; Green, L., 1999, J. Immunol. Methods 231:11-

23; Yang, X. et al., 1999, Cancer Res. 59:1236-1243; Brüggemann, M. and Taussig, M J., Curr. Opin. Biotechnol. 8:455-458, 1997; Tomizuka et al. WO02043478). The endogenous immunoglobulin loci in such mice can be disrupted or deleted to eliminate the capacity of the animal to produce antibodies encoded by endogenous genes. In addition, companies, such as Abgenix, Inc. (Freemont, Calif.) and Medarex (San Jose, Calif.) can be engaged to provide human antibodies directed against a selected antigen using technology as described above.

In another embodiment, the human antibody is selected from a phage library, where that phage comprises human immunoglobulin genes and the library expresses human antibody binding domains as, for example, single chain antibodies (scFv), as Fabs, or some other construct exhibiting paired or unpaired antibody variable regions (Vaughan et lo al. Nature Biotechnology 14:309-314 (1996): Sheets et al. PITAS (USA) 95:6157-6162 (1998)); Hoogenboom and Winter, J. Mol. Biol., 227:381 (1991); Marks et al. J. Mol. Biol., 222:581 (1991)). Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and U.S. Pat. No. 5,571,698 to Ladner et al.; U.S. Pat. Nos. 5,427,908 and 5, 580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Preparation of immunogenic antigens, and monoclonal antibody production can be performed using any suitable technique, such as recombinant protein production. The immunogenic antigens can be administered to an animal in the form of purified protein, or protein mixtures including whole cells or cell or tissue extracts, or the antigen can be formed de novo in the animal's body from nucleic acids encoding said antigen or a portion thereof.

The isolated nucleic acids of the present invention can be made using (a) recombinant methods, (b) synthetic techniques, (c) purification techniques, or combinations thereof, as well-known in the art. DNA encoding the monoclonal antibodies is readily isolated and sequenced using methods known in the art (e.g., by using oligonucleotide probes that are capable of binding specifically to genes encoding the heavy and light chains of murine antibodies). Where a hybridoma is produced, such cells can serve as a source of such DNA. Alternatively, using display techniques wherein the coding sequence and the translation product are linked, such as phage or ribosomal display libraries, the selection of the binder and the nucleic acid is simplified. After phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria.

Humanized Antibodies

The invention further provides humanized (engineered or human adapted) immunoglobulins (or antibodies) which bind human CD27. The humanized forms of immunoglobulins have variable framework region(s) substantially from a human immunoglobulin (termed an acceptor immunoglobulin) and CDRs substantially from a non-human Mab which specifically binds CD27. The constant region(s), if present, are also substantially from a human immunoglobulin. The humanized antibodies exhibit $K_D$ for CD27 of at least about $10^{-6}$ M (1 microM), about $10^{-7}$ M (100 nM), or less. The binding affinity of the humanized antibodies may be greater or less than that of the mouse antibody from which they were derived. To affect a change in affinity, e.g., improve affinity, of the humanized antibody for CD27 substitutions in either the CDR residues or the human residues may be made.

The substitution of mouse CDRs into a human variable domain framework is most likely to result in retention of their correct spatial orientation if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies, be derived from human germline immunoglobulin sequences, or can be consensus sequences of several human antibody and/or germline sequences.

Suitable human antibody sequences are identified by computer comparisons of the amino acid sequences of the mouse variable regions with the sequences of known human antibodies. The comparison is performed separately for heavy and light chains but the principles are similar for each.

In one example, the amino acid sequence of a CD27-neutralizing mAb is used to query a human antibody database compiled from public antibody sequence databases. The heavy chain variable regions disclosed or described herein can be used to find the human variable region with the highest sequence identity. The variable region of the light chain disclosed or described herein can, similarly, be used to find the human variable region with the highest sequence identity. A DNA construct in which the regions coding for the CDRs of one of the heavy chain variable regions from the murine Mab donor are transferred into the selected human heavy chain variable sequence, replacing the CDRs of the human variable region is prepared for each murine variable region.

The unnatural juxtaposition of murine CDR regions with human variable framework region can result in unnatural conformational restraints, which, unless corrected by substitution of certain amino acid residues, lead to loss of binding affinity.

As noted supra, the humanized antibodies of the invention comprise variable framework region(s) substantially from a human immunoglobulin and CDRs substantially from a mouse immunoglobulin (e.g., C2177, C2186, C2191, or C2192 mouse antibodies). Having identified the CDRs of mouse antibodies and appropriate human acceptor immunoglobulin sequences, the next step is to determine which, if any, residues from these components should be substituted to optimize the properties of the resulting humanized antibody. In general, substitution of human amino acid residues with murine should be minimized, because introduction of murine residues increases the risk of the antibody eliciting a HAMA response in humans. Amino acids are selected for substitution based on their possible influence on CDR conformation and/or binding to antigen. Investigation of such possible influences can be done by modeling, examination of the characteristics of the amino acids at particular locations, or empirical observation of the effects of substitution or mutagenesis of particular amino acids. With regard to the empirical method, it has been found to be particularly convenient to create a library of variant sequences that can be screened for the desired activity, binding affinity or specificity. One format for creation of such a library of variants is a phage display vector. Alternatively, variants can be generated using other methods for varigation of a nucleic acid sequence encoding the targeted residues within the variable domain.

Another method of determining whether further substitutions are required, and the selection of amino acid residues for substitution, can be accomplished using computer modeling. Computer hardware and software for producing three-dimensional images of immunoglobulin molecules are widely available. In general, molecular models are produced starting from solved structures for immunoglobulin chains or domains thereof. The chains to be modeled are compared for amino acid sequence similarity with chains or domains of solved three dimensional structures, and the chains or domains showing the greatest sequence similarity is/are selected as starting points for construction of the molecular model. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

Usually the CDR regions in humanized antibodies are substantially identical, and more usually, identical to the corresponding CDR regions in the mouse antibody from which they were derived. Although not usually desirable, it is sometimes possible to make one or more conservative amino acid substitutions of CDR residues without appreciably affecting the binding affinity of the resulting humanized immunoglobulin. Occasionally, substitutions of CDR regions can enhance binding affinity.

Other than for the specific amino acid substitutions discussed above, the framework regions of humanized immunoglobulins are usually substantially identical, and, more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin.

Because of the degeneracy of the code, a variety of nucleic acid sequences will encode each immunoglobulin amino acid sequence. The desired nucleic acid sequences can be produced by de nova solid-phase DNA synthesis or by PCR mutagenesis of an earlier prepared variant of the desired polynucleotide. All nucleic acids encoding the antibodies described in this application are expressly included in the invention.

The variable segments of humanized antibodies produced as described supra are typically linked to at least a portion of a human immunoglobulin constant region. The antibody will contain both light chain and heavy chain constant regions. The heavy chain constant region usually includes CH1, hinge, CH2, CH3, and, sometimes, CH4 domains.

The humanized antibodies may comprise any type of constant domains from any class of antibody, including IgM, IgG, IgD, IgA and IgE, and any subclass (isotype), including IgG1, IgG2, IgG3 and IgG4. When it is desired that the humanized antibody exhibit cytotoxic activity, the constant domain is usually a complement-fixing constant domain and the class is typically IgG$_1$. When such cytotoxic activity is not desirable, the constant domain may be of the IgG$_2$ class. The humanized antibody may comprise sequences from more than one class or isotype.

Nucleic acids encoding humanized light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence (see Queen et al., Proc. Natl. Acad. Sci. USA 86, 10029 (1989); WO 90/07861; Co et al., J. Immunol. 148, 1149 (1992), which are incorporated herein by reference in their entirety for all purposes).

Efficacy of a therapeutic protein can be limited by unwanted immune reactions. Non-human monoclonal antibodies can have substantial stretches of linear amino acid sequences and local structural conformations that can elicit immune response in humans. The first attempt to reduce immunogenicity of non-human antibodies was the construction of human-murine antibody chimeras, which was then followed by methods for humanization of those chimeras in the late 1980's (review in Almagro and Fransson, *Front Biosci* 13: 1619-1633, 2008).

One of the most often used humanization approaches is the so-called "Complementarity-Determining Regions (CDR) grafting" wherein murine CDR's are grafted into human antibody Framework Regions (FR's). Nevertheless, application of this method more often than not results in a substantial loss of binding to antigen and thus a reduction in potency of the antibody-based drug. Hence, it is highly valuable to use sound design principles for creating antibody molecules that elicit minimal immunogenic reactions while retaining the binding and biophysical profiles of the parent non-human molecule when injected into humans.

The humanization of 2177 and 2191, two mouse monoclonal antibodies (mAb) with binding specificity to CD27 is described. The frameworks (FR) of these antibodies were replaced by human germline gene FRs using the first step of the Janssen proprietary humanization technology called Human Framework Adaption (HFA) disclosed in the patent application Raghunathan, G., US20090118127 A1 and further exemplified in Fransson et al (J Mol Biol 398:214-231, 2010). This technology enables a set of mAbs specific for CD27 with superior binding and inhibition properties to those measured for the parental mouse antibodies 2177 and 2191.

3. Methods of Using an Anti-CD27 Antibody

As described in detail below, the present invention demonstrates that four isolated monoclonal antibodies (C2177, C2186, C2191, and C2192) bind three non-overlapping epitopes on CD27 and display in vitro and/or in vivo CD27 inhibiting activities. Significantly, the reactivity of the MAbs includes the ability to dose-dependently block CD27 interaction with CD70, reduce CD27 signaling in the presence of CD70, reduce IL-4 and IFNg production by T-cells, and inhibit CD70-dependent human naïve CD4+ T-cell proliferation, CD70-dependent B-cell proliferation and plasma cell generation. Moreover, isolated antibodies do not significantly induce CD27 activation in the absence of CD70 stimulus.

Given the properties of the monoclonal antibodies as described in the present invention, the antibodies or antigen binding fragments thereof are suitable both as therapeutic and prophylactic agents for treating or preventing CD27-associated conditions in humans and animals.

In general, use will comprise administering a therapeutically or prophylactically effective amount of one or more monoclonal antibodies or antigen binding fragments of the present invention, or an antibody or molecule selected to have similar spectra of binding and biologic activity, to a susceptible subject or one exhibiting a condition in which CD27 activity is known to have pathological sequelae, such as immunological disorders or tumor growth and metastasis. Any active form of the antibody can be administered, including Fab and F(ab')2 fragments.

Preferably, the antibodies used are compatible with the recipient species such that the immune response to the MAbs does not result in an unacceptably short circulating half-life or induce an immune response to the MAbs in the subject. The MAbs administered may exhibit some secondary functions, such as binding to Fc receptors of the subject and activation of ADCC mechanisms, in order to deplete the target cell population using cytolytic or cytotoxic mechanisms or they may be engineered to by limited or devoid of these secondary effector functions in order to preserve the target cell population.

Treatment of individuals may comprise the administration of a therapeutically effective amount of the antibodies of the present invention. The antibodies can be provided in a kit as described below. The antibodies can be used or administered as a mixture, for example, in equal amounts, or individually, provided in sequence, or administered all at once. In providing a patient with antibodies, or fragments thereof, capable of binding to CD27, or an antibody capable of protecting against CD27 in a recipient patient, the dosage of administered agent will vary depending upon such factors as the patient's age, weight, height, sex, general medical condition, previous medical history, etc.

In a similar approach, another therapeutic use of the monoclonal antibodies of the present invention is the active immunization of a patient using an anti-idiotypic antibody raised against one of the present monoclonal antibodies. Immunization with an anti-idiotype which mimics the structure of the epitope could elicit an active anti-CD27 response (Linthicum, D. S. and Farid, N. R., Anti-idiotypes, Receptors, and Molecular Mimicry (1988), pp 1-5 and 285-300).

Likewise, active immunization can be induced by administering one or more antigenic and/or immunogenic epitopes as a component of a vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cysteine and derivatives thereof. Alternative protein modification techniques may be used, e.g., NH2-acetylation or COOH-terminal amidation, to provide additional means for coupling or fusing the peptide to another protein or peptide molecule or to a support.

The antibodies capable of protecting against unwanted CD27 bioactivity are intended to be provided to recipient subjects in an amount sufficient to effect a reduction, resolution, or amelioration in the CD27-related symptom or pathology. An amount is said to be sufficient or a "therapeutically effective amount" to "effect" the reduction of symptoms if the dosage, route of administration, etc. of the agent are sufficient to influence such a response. Responses to antibody administration can be measured by analysis of subject's affected tissues, organs, or cells as by imaging techniques or by ex vivo analysis of tissue samples. An agent is physiologically significant if its presence results in a detectable change in the physiology of a recipient patient.

Therapeutic Applications

The CD27-neutralizing antibodies of the present invention, antigen binding fragments, or specified variants thereof can be used to measure or cause effects in an cell, tissue, organ or animal (including mammals and humans), to diagnose, monitor, modulate, treat, alleviate, help prevent the incidence of, or reduce the symptoms of, a condition mediated, affected or modulated by CD27 or cells expressing CD27. Thus, the present invention provides a method for modulating or treating at least one CD27 related disease, in a cell, tissue, organ, animal, or patient, as known in the art or as described herein, using at least one CD27 antibody of the present invention. Particular indications are discussed below.

Immune Related Disease

The present invention also provides a method for modulating or treating an immune related inflammatory disease, in a cell, tissue, organ, animal, or patient including, but not limited to rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, OKT3 therapy, anti-CD3 therapy, cytokine therapy, chemotherapy, radiation therapy (e.g., including but not limited to asthenia, anemia, cachexia, and the like), chronic salicylate intoxication, and the like.

Pulmonary Disease

The present invention also provides a method for modulating or treating a pulmonary or pleural disease in a cell, tissue, organ, animal or patient, including, but not limited to, modulating the immune-response to associated or ancillary cells or cellular processes involving CD27 in, for example, pneumonia; lung abscess; occupational lung diseases caused be agents in the form or dusts, gases, or mists; asthma, bronchiolitis fibrosa obliterans, respiratory failure, hypersensitivity diseases of the lungs including hypersensitivity pneumonitis (extrinsic allergic alveolitis), allergic bronchopulmonary aspergillosis, and drug reactions; adult respiratory distress syndrome (ARDS), Goodpasture's Syndrome, chronic obstructive airway disorders (COPD), idiopathic interstitial lung diseases such as idiopathic pulmonary fibrosis, sarcoidosis, desquamative interstitial pneumonia, acute interstitial pneumonia, respiratory bronchiolitis-associated interstitial lung disease, idiopathic bronchiolitis obliterans with organizing pneumonia, lymphocytic interstitial pneumonitis, Langerhans' cell granulomatosis, idiopathic pulmonary hemosiderosis; acute bronchitis, pulmonary alveolar proteinosis, bronchiectasis, pleural disorders, atelectasis, cystic fibrosis, and tumors of the lung, and pulmonary embolism.

Malignant Disease

The present invention also provides a method for modulating or treating a malignant disease in a cell, tissue, organ, animal or patient, including, but not limited to, modulating the immune-response to associated or ancillary cells or cellular processes involving CD27 in, at least one of: leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, solid tumors as primary disease or as metastatic disease, Kaposi's sarcoma, colorectal carcinoma, pancreatic carcinoma, renal cell carcinoma, lung cancer including mesothelioma, breast cancer, nasopharyngeal carcinoma, malignant histiocytosis, paraneoplastic syndrome/hypercalcemia of malignancy, adenocarcinomas, squamous cell carcinomas, sarcomas, malignant melanoma, particularly metastatic melanoma, hemangioma, metastatic disease, cancer related bone resorption, cancer related bone pain, and the like.

Cardiovascular Disease

The present invention also provides a method for modulating or treating a cardiovascular disease in a cell, tissue, organ, animal, or patient, including, but not limited to, modulating the immune-response to associated or ancillary cells or cellular processes involving CD27 in, at least one of myocardial infarction, congestive heart failure, stroke, ischemic stroke, hemorrhage, arteriosclerosis, atherosclerosis, restenosis, diabetic atheriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occulsion of the abdominal aorta and its branches, peripheral vascular disorders, occulsive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like.

Neurologic Disease

The present invention also provides a method for modulating or treating at neurologic disease in a cell, tissue, organ, animal or patient, including, but not limited to, modulating the immune-response to associated or ancillary cells or cellular processes involving CD27 in: neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders, such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi.system disorder); demyelinating core disorders, such as multiple sclerosis, acute transverse myelitis; and disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome; diffuse Lewy body disease; senile dementia related to Lewy body development; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Such a method can optionally comprise administering an effective amount of a composition or pharmaceutical composition comprising at least one TNF antibody or specified portion or variant to a cell, tissue, organ, animal or patient in need of such modulation, treatment or therapy.

Other Therapeutic Uses of CD27-Neutralizing Antibodies

In addition to the above described conditions and diseases, the present invention also provides a method for modulating or treating fibrotic conditions of various etiologies by modulating the immune-response to associated or ancillary cells or cellular processes involving CD27 in, for example: liver fibrosis (including but not limited to alcohol-induced cirrhosis, viral-induced cirrhosis, autoimmune-induced hepatitis); lung fibrosis (including but not limited to scleroderma, idiopathic pulmonary fibrosis); kidney fibrosis (including but not limited to scleroderma, diabetic nephritis, glomerular pehpritis, lupus nephritis); dermal fibrosis (including but not limited to scleroderma, hypertrophic and keloid scarring, burns); myelofibrosis; neurofibromatosis; fibroma; intestinal fibrosis; and fibrotic adhesions resulting from surgical procedures.

The present invention also provides a method for modulating or treating or ameliorating the symptoms of an infectious disease in a cell, tissue, organ, animal or patient, by modulating the immune-response to associated or ancillary cells or cellular processes involving CD27 in, for example: acute or chronic bacterial infection, acute and chronic parasitic or infectious processes, including bacterial, viral and fungal infections, HIV infection/HIV neuropathy, meningitis, hepatitis (A, B or C, or the like), septic arthritis, peritonitis, pneumonia, epiglottitis, *E. coli*, hemolytic uremic syndrome, malaria, dengue hemorrhagic fever, leishmaniasis, leprosy, toxic shock syndrome, streptococcal myositis, gas gangrene, *mycobacterium tuberculosis, mycobacterium avium intracellulare, pneumocystis carinii* pneumonia, pelvic inflammatory disease, orchitis or epidydimitis, *legionella*, lyme disease, influenza a, Epstein-Barr virus, vital-associated hemaphagocytic syndrome, vital encephalitis/aseptic meningitis, and the like.

The contents of all cited references (including literature references, issued patents, published patent applications, and co-pending patent applications) throughout this application are hereby expressly incorporated by reference.

Other features of the invention will become apparent in the course of the following descriptions of exemplary embodiments which are given for illustration of the invention and are not intended to be limiting thereof.

4. Pharmaceutical Formulations

The invention provides for stable formulations of an CD27-neutralizing antibody, which is preferably an aqueous phosphate buffered saline or mixed salt solution, as well as preserved solutions and formulations as well as multi-use preserved formulations suitable for pharmaceutical or veterinary use, comprising at least one CD27-neutralizing antibody in a pharmaceutically acceptable formulation. Suitable vehicles and their formulation, inclusive of other human proteins, e.g., human serum albumin, are described, for example, in e.g. Remington: The Science and Practice of Pharmacy, 21st Edition, Troy, D. B. ed., Lipincott Williams and Wilkins, Philadelphia, Pa. 2006, Part 5.

In order to form a pharmaceutically acceptable composition suitable for effective administration, such compositions will contain an effective amount of the above-described compounds together with a suitable amount of carrier vehicle. Additional pharmaceutical methods may be employed to control the duration of action. Controlled release preparations may be achieved through the use of polymers to complex or absorb the compounds. Another possible method to control the duration of action by controlled release preparations is to incorporate the compounds of the present invention into particles of a polymeric material such as polyesters, polyamino acids, hydrogels, poly (lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions. Such techniques are disclosed in Remington supra (2006).

5. Administration of a CD27-Neutralizing Antibody

At least one CD27-neutralizing antibody in either the stable or preserved formulations or solutions described herein, can be administered to a patient in accordance with the present invention via a variety of delivery methods including intravenous (I.V.), intramusclular (I.M.); subcutaneously (S.C.); transdermal, pulmonary, transmucosal, using an formulation in an implant, osmotic pump, cartridge, micropump, or other means appreciated by the skilled artisan, as well-known in the art.

In one method of administering a CD27-neutralizing antibody, the drug substance is given intravenously from a previously installed catheter equipped with an infusion bag. The CD27-neutralizing antibody is supplied in 20-ml single-use vials, such as those supplied by ImmunoGen, Inc. (Cambridge, Mass.). Each vial contains protein at a concentration of from 0.05 to about 2.0 mg/ml in a buffered solution (pH 6.5±0.5) comprised essentially of monobasic potassium phosphate (0.57 mg/ml), monobasic sodium phosphate monohydrate (0.20 mg/ml), dibasic sodium phosphate (0.555 mg/ml), and sodium chloride (8.16 mg/ml) in purified water, USP. The drug product is prefiltered twice upon instilling the dose volume into the infusion bag by passing it through a low protein-binding 5-μ filter and is administered to patients through an inline 0.22 μm filter within 8 h of preparation. After infusion, the i.v. line should be flushed with fluid to ensure delivery of the full drug dose.

In general, if administering a systemic dose of the antibody, it is desirable to provide the recipient with a dosage of antibody which is in the range of from about 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg (body weight of recipient), although a lower or higher dosage may be administered. Dosages as low as about 1.0 mg/kg may be expected to show some efficacy. Preferably, about 5 mg/kg is an acceptable dosage, although dosage levels up to about 50 mg/kg are also preferred especially for therapeutic use. Alternatively, administration of a specific amount of the antibody may be given which is not based upon the weight of the patient such as an amount in the range of 1 ug-100 ug, 1 mg-100 mg, or 1 gm-100 gm. For example, site specific administration may be to body compartment or cavity such as intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, vaginal, rectal, buccal, sublingual, intranasal, or transdermal means.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

6. Articles of Manufacture Comprising a CD27-Neutralizing Antibody

The invention includes an article of manufacture containing materials useful for the treatment of the disorders described above comprising a CD27-neutralizing antibody, a container and a label or package insert on or associated with the container. The article of manufacture preferably contains at least one vial comprising a solution of at least one CD27-neutralizing antibody with the prescribed buffers and/or preservatives, optionally in an aqueous diluent, wherein said packaging material comprises a label that indicates that such solution can be held over a period of time. The invention may comprise an article of manufacture, comprising packaging material, a first vial comprising lyophilized CD27-neutralizing antibody, and a second vial comprising an aqueous diluent of prescribed buffer or preservative, wherein said packaging material comprises a label that instructs a practitioner or patient how to reconstitute the CD27-neutralizing antibody in the aqueous diluent to form a solution.

Suitable containers include, for example, bottles, vials, syringes, etc. The containers may be formed from a variety of materials such as glass or plastic. The container may have a sterile access port (for example the container may be an intravenous solution bag or a vial having a stopper, optionally, capable of being pierced by a hypodermic injection needle).

At least one active agent in the composition is a CD27-neutralizing antibody. The label or package insert indicates that the composition is used for treating the indication of choice, such as SLE. The package insert herein may indicate that the antibody or composition is used to treat a condition that does not respond, or respond poorly, to treatment with the standard of care as outlined herein for specific diseases and diagnoses. In other embodiments, the package insert may indicate that the antibody, antibody-conjugate or composition can be used also to treat a disease characterized by the need to modulate the immune-response of cellular processes involving CD27.

Yet another aspect of the present invention is a kit for detecting CD27 in a biological sample. The kit includes a container holding one or more antibodies which binds an epitope of CD27 and instructions for using the antibody for the purpose of binding to CD27 to form an immunological complex and detecting the formation of the immunological complex such that the presence or absence of the immunological complex correlates with presence or absence of CD27 in the sample. Examples of containers include multiwell plates which allow simultaneous detection of CD27 in multiple samples.

While having described the invention in general terms, the embodiments of the invention will be further disclosed in the following examples.

Example 1: CD27 Reagents and Methods

In order to generate and test CD27-binding monoclonal antibodies, protein constructs were generated which represent the full length of human CD70 and human CD27 and the extracellular domain (ECD) of human CD27.

Human CD27 (SEQ ID NO: 149) is a type 1 transmembrane protein comprised of a signal peptide (from residues 1 to 20), extracellular (ECD, from residues 21 to 191), transmembrane (TM, from residues 191 to 212) and intracellular (ICD, from residues 213 to 260) domains. Human CD70 (SEQ ID NO: 2) is a type 2 transmembrane polypeptide of 193 amino acids in length comprised of, from the N-terminus, an intracellular domain (ICD, from residues 1 to 17), transmembrane (TM, from residues 18 to 38) and extracellular domain (ECD, from residues 39 to 193). The complete CD70 coding sequence was clonally expressed on the surface of HEK 293 cells.

For mAb ELISA and Proteon-based direct binding assays, amino acids 1-121 of the CD27 ECD were transiently expressed in HEK293 cells with a C-terminal His6-tag peptide and purified by metal ion chromatography. For phage panning and ELISA assays, amino acids 1-173 of the ECD with a C-terminal His6-tag were HEK expressed and purified by metal ion chromatography followed by size exclusion chromatography on Superdex 75. Both of these CD27 proteins were biotinylated using NHS-ester chemistry targeting amine residues on the protein. For crystallization, amino acids 1-101 with a C-terminal His6-tag were expressed in a baculovirus system and purified by metal ion chromatography by Proteose, Inc. For mouse immunization, CD27-Fc protein was purchased from R&D systems. For some studies, the complete CD27 coding sequence was clonally expressed on the surface of HEK 293 cells.

Human CD27 and human CD70 cDNA clones were ordered from Open Biosystems. Standard molecular biology techniques were used to generate expression constructs. Briefly, the open reading frames of the CD27 and CD70 genes were PCR amplified and cloned into the mammalian expression vectors via restriction endonuclease digestion and ligation, or via ligase independent cloning (LIC). Full length CD27 and CD70 genes were cloned into the expression vector and were clonally expressed on the surface of mammalian cells. The extracellular domain of CD27 was cloned into mammalian expression vectors and transiently expressed in HEK293 cells with a hexa-his tail.

Example 2: GENERATION of CD27-NEUTRALIZING ANTIBODIES

Murine anti-human CD27 antibodies were generated by the hybridoma method of Kohler and Milstein (1975). Ten 12-14 week old C3H/HeJ mice were obtained from Charles River Laboratories. The mice were immunized subcutaneously (SQ) at the base of tail (BOT) with 50 microgm Hu CD27 Fc (R&D Systems) in combination with $0.33 \times 10^5$ units each of murine interferon-alpha and -beta (Biosource) in a final volume of 100 microL on day 1. On days 2 and 3, the mice were injected SQ BOT with the interferons (same doses as on day 1). The mice were boosted with 50 microgm Hu CD27-Fc in combination with 50 microgm anti-murine CD40 agonist Mab (R&D Systems, MAB440) given SQ BOT in PBS on day 14; four days prior to splenic harvest for fusion.

For titer assessment, a capture phase EIA was performed. Briefly, plates (Nunc-Maxisorp) were coated with 0.1 microgram goat anti-ms Fc (Jackson Immunotech) in bicarbonate buffer overnight at 4° C. After blocking and washing steps, dilutions of sera were added and plates were incubated for 30 minutes at RT. Following washing steps, the plates were incubated for 30 minutes at RT with 0.25 microgm/mL of biotinylated Hu CD27-ECD in blocking buffer and probed with HRP labeled Streptavidin (Jackson Immunotech)

diluted 1:40,000 in 0.4% BSA/PBS of for 30 minutes at RT. Plates were washed as described above; then OPD (Sigma fast tabs) substrate solution was added, incubation for 10 minutes at room temperature, the color substrate development stopped by the addition of 4N sulfuric acid at 25 microL/well, and the absorbance measured at 490 nm.

A cell bank of the non-secreting BALB/c mouse myeloma fusion partner, FO was purchased from ATCC (# CRL-1646). One frozen vial of FO cells was thawed and resuspended in DMEM with Glutamax™ (modified) medium (Invitrogen) supplemented with 10% (v/v) FBS (Hyclone). The cells were expanded, cryopreserved and deemed sterile and free of mycoplasma by Charles River Laboratories. The C1833A (Centocor) cell line was also used in this fusion. This cell line was derived in-house by knocking down expression of the CHOP gene in the FO cell line so it requires growth under selection with geneticin. Cells were treated as FO's above with the exception of growing in DMEM with Glutamax™ (modified) medium supplemented with 10% (v/v) FBS (Hyclone) and 500 ug/mL of geneticin (Gibco). Both the FO and C1833A cell lines were subjected to cell synchronization prior to fusion. Briefly, 1.5-2×10$^8$ cells were seeded into 180 mL of DMEM with Glutamax™ (modified) medium supplemented with 0.25% (v/v) FBS (Hyclone) and incubated at 37° C. for 13 hours. An additional 20 mL of FBS was added for a final FBS concentration of 10% and incubated for an additional 13 hours at 37° C. prior to use. C1833A cells were constantly under geneticin selection throughout cell synchronization process. The myeloma cells were washed in PBS, counted, and viability determined (>78%) via Guava Viacount software prior to fusion.

On the day of fusion, the animals were euthanized by $CO_2$ asphyxiation. The spleens were removed aseptically and immersed in 10 mL of cold phosphate-buffered saline (PBS) containing antibiotics (PSA) (Sigma).

A single cell suspension of splenocytes was prepared and subjected to RBC lysis using RBC lysis buffer (Sigma). Washed cells were labeled for magnetic sorting as per the manufacturer's instructions, using anti-murine Thy1.2, anti-murine/human CD11b and anti-murine IgM magnetic beads (Miltenyi Biotec #130-049-101, 130-149-601 and 130-047-301 respectively) and then sorted using the AutoMacs Pro instrument by running the Deplete program. Both the unlabeled (plasmablast B cell enriched) and labeled cell fractions were collected then counted via the Guava PCA. Positively labeled cells were discarded. Unlabeled cells were divided in half for fusion to both FO and C1833A fusion partners. Fusions were carried out at a 1:1 ratio of murine myeloma cells to viable spleen cells according to the method of De St. Groth (J Immunological Methods. 35:1-21. 1980). Briefly, spleen and myeloma cells were mixed together, pelleted and washed once in 50 mL of PBS. The pellet was resuspended with 1 mL of polyethylene glycol (PEG) solution (2 g PEG molecular weight 4000, 2 mL DMEM, and 0.4 mL DMSO) at 37° C. over 30 seconds. The cell/fusion mixture was then immersed in a 37° C. water bath for approximately 60 seconds with gentle agitation. The fusion reaction was stopped by slowly adding 37° C. DMEM over 1 minute. The fused cells were allowed to rest or 5 minutes at room temperature and then centrifuged at 150×g for 5 minutes. Cells were then resuspended in HAT medium [DMEM with Glutamax™ (modified), supplemented with 20% FBS, 5% Origen, 25 microg/mL gentamicin (Sigma) and HAT (100 microM hypoxanthine, 0.4 microM aminopterin, and 16 microM thymidine (Sigma), and seeded in 96-well flat bottom polystyrene tissue culture plates (Corning #3997) or methylcellulose medium (StemCell Technologies, MediumD cat#03804) containing ~2.25 µg/mL of AF488 human CD27 (Janssen Research & Development, LLC). Plates were incubated in a humidified 37° C. incubator with 7% $CO_2$ for 7-10 days. Single colonies were selected from methylcellulose plates for screening utilizing the ClonepixFL or under a white light microscope.

Example 3: Bioactivity of Recombinant Mabs

The ability of the binding domains from the murine antibodies to bind CD27 and to block certain bioactivities of CD27 was analyzed using various in vitro assays as described below.

A solid phase EIA was used to screen the hybridoma supernatants for antibodies capable of binding human CD27. Plates (Nunc-Maxisorp #446612) were coated overnight with 4 µg/mL Fab goat anti-huFc (Jackson #109-006-098) in Bicarbonate buffer O/N at 4° C. Without washing, the wells were blocked with 200 microL of 0.4% (w/v) bovine serum albumin (BSA) in PBS for 1 hr at RT. After washing with 0.15 M saline containing 0.02% (w/v) Tween 20, 50 microl of huCD27-Fc in 0.4% BSA/PBS was added to the plates for 1 hr at RT. After washing again, 50 microl of undiluted hybridoma supernatants were incubated on coated plates for 30 minutes at RT. Plates were washed three times and then incubated with 50 microL of goat anti-murine Fc HRP (Jackson #115-036-071) diluted 1:10,000 for 30 minutes at RT. Plates were again washed and developed as described above for titer assessment. For assessment relative binding capacity of hybridoma Mabs similar assay was performed using Maxisorp 384 well plates (NUNC 464718) with serially diluted hybridoma supernatants (normalized to a starting concentration of 5 microg/mL. This assay identified 386 positive hybridomas.

All 386 CD27 specific hybridomas were screened for the ability to inhibit binding of huCD27 to huCD70 using biochemical binding assays with IM-9 cells, a B-lymphoblastoid cell line found to endogenously expressing human CD70. Maxisorp plates (VWR #62409-314) were coated with recombinant human CD27/Fc (R&D Systems, Cat#382-CD) at 250 nanogram (ng)/mL and incubated overnight at 4° C. The next day plates were blocked with blocking buffer (Pierce, Cat#37543) and then washed with wash buffer I, that contains PBS without Ca++ or Mg++, 0.01% Tween-20. Controls (mouse MAB to hCD27, R&D Systems, Cat# MAB382; Mouse IgG1 isotype control, R&D Systems, Cat# MAB002; mouse IgG2a isotype control, R&D Systems, Cat# MAB003) were included on each plate. 50 uL/well of hybridoma samples or controls were mixed with 50 µL/well of harvested IM-9 cells, human B-lymphoblastoid cell line (ATCC, CCL-159) and were incubated for 1 hour at RT without shaking. At the end of incubation, plates were washed with wash buffer II, to remove all unbound cells, and then lysed with 50 uL/well of Cell Titer Glo reagent (Promega, Cat# G7571). After 10 minutes incubation with shaking, plates were read on Envision (PerkinElmer, 2102 Multilabel reader). The luminescent signal generated is proportional to the amount of ATP present and directly correlated to the number of live cells present in the well captured by CD27 binding. Based on the results of the biochemical binding assay, about 50% of CD27 specific clones were neutralizing.

To eliminate redundancy among the neutralizing clones, competition binding assays were performed to bin the antibodies into competition groups. In this assay, hybridoma supernatants were assessed individually as both capture and detection reagents with each of the positive hybridomas in the panel. Antibodies forming effective capture/detection reagents with each other likely recognize spatially-separated epitopes on the CD27 protein, thus allowing both antibodies to bind to the target protein at the same time. Groups of clones exhibiting similar patterns of activity across the entire panel likely bind to similar epitopes. Selecting clones from different groups therefore provided antibodies recognizing different epitopes. Briefly, 384 well Nunc Maxisorp plates (464718) were coated with goat anti-mouse Fc (JIR115-005-071) in coating buffer overnight at 4° C. Plates were then blocked with 0.4% BSA in PBS for 30 minutes at room temperature. At this step and all subsequent steps plates are washed with PBS, 0.02% Tween-20. Each well of a row (one row per supernatant) received 20 uL of supernatant (neat supernatant was used for the initial screen but for rescreening the subclones, supes were normalized to 2 ug/ml of mAb) was along with controls (mouse anti-huCD27, R&D Systems, Cat# MAB382; mouse isotype control Cat#555439, Becton-Dickenson) then incubated for 30 minutes at RT. After washing, 25 uL of unlabeled Hu CD27-ECD-His-tag was prepared in PBS plus 10% mouse sera (Bioreclamation mouse serum CD-1 lot#MSEBREC.18565) at 0.3 (or 0.8 for concentration normalized) microg/ml was added to all wells, followed by 30 minutes incubation at room temperature then washed. Each supernatant was added down a single column and incubated for 30 minutes at RT with 25 uL of a mixture prepared as follows: (—pre-incubate supernatants with goat anti-mouse Fc HRP (Jackson 115-036-008), by mixing 150 uL of 1:1000 goat anti-mouse Fc HRP with each 1000 uL of supernatant (for the primary screen) or 90 uL of 1:2000 per 600 uL of supernatant adjusted to 2 ug/mL: (for rescreening subclones). After 30 minutes incubation at room temperature, add 200 microL of 100% normal mouse sera per mL and incubate an additional 30 minutes at RT. Plates were washed then incubated for 15 minutes at RT with 100 uL/well of citrate-phosphate substrate solution (0.1 M citric acid and 0.2 M sodium phosphate, 0.01% H2O2, and 1 mg/mL OPD). Substrate development was stopped by addition of 25 uL of 4N sulfuric acid and the absorbance measured at 490 nm using an automated plate reader. This binning assay identified three groups that recognize non-overlapping binding sites on huCD27 antigen. Selected antibodies from all three groups were scaled up for antibody production, purification and further testing in functional assays.

Inhibition of Cell Signaling

Binding of CD70 to CD27 induces signaling that leads to downstream activation of the transcription factor, NF-kβ. A NF-kβ reporter assay was established for further antibody characterization. The assay was run in two modes: (1) to assess antibody antagonism by neutralization of CD70 induced CD27 activation and (2) to assess antibody agonism by activation of CD27 signaling without CD70 ligation. HEK-293F cells were transfected with a total of 36 ng of DNA containing both human CD27 and luciferase constructs, under control of the NF-kβ promoter. HEK-293F transfectants were plated $5 \times 10^4$ cells per well in 40 uL Freestyle media (Gibco) in 96-well plates. Dilutions of CD27-neutralizing hybridoma mAbs were added to the assay plate in Freestyle media (Gibco) for a final concentration of 50 ug/mL with 1:3 dilutions and plates were incubated at 37° C. (95% $O_2$/5% $CO_2$) for one hour. To test for ability of hybridoma mAbs to neutralize CD70:CD27 signaling, terminally irradiated (4000 rads) HEK-293E CD70 episomal cells were added at 20% of the number of CD27 transfectant cells to the assay plate. To test for agonist activity of hybridoma mAbs, addition of CD70 episomal cells was omitted. Assay plates were incubated overnight at 37° C. (95% $O_2$/5% $CO_2$) and developed using the Steady-Glo® Luciferase Assay System (Promega) according to the instructions of the manufacturer. Four CD27-neutralizing hybridoma mAbs, C2177, C2186, C2191, and C2192, that dose-dependently blocked the CD70-mediated CD27 signaling without causing significant dose-dependent agonistic activation of the CD27 receptor in the absence of CD70 stimulus were selected for further characterization. The $IC_{50}$s for blocking IM-9 cell binding to CD27 and CD70-mediated signaling in NF-kβ reporter gene assay are summarized for these four antibodies in Table 1. Agonism activity in the NF-kβ reporter gene assay is shown as fold increase in CD27 signaling relative to an irrelevant isotype control antibody (mouse IgG1 to rat EMP protein) in the absence of CD70 stimulus at the maximum tested concentration of antibody.

Affinity for CD27

The Kms of antibodies C2177, C2186, C2191, and C2192 for monomeric soluble CD27 at 25° C. were measured by Biacore and are reported in Table 1. Assays were carried out on a BIACORE 3000 (BIAcore, Inc.) surface plasmon resonance (SPR) instrument. The samples were prepared in Dulbecco's phosphate buffered saline pH 7.4 containing 0.005% surfactant (polysorbate 20). Goat anti-mouse Fc specific antibody (Jackson Immunoresearch laboratories Prod #115-005-071) was covalently attached to carboxymethyl dextran coated gold surfaces (CM-5 Chip, Biacore). Prior to immobilization the chip was pretreated with 50 mM NaOH, 100 mM HCl and 0.1% sodium dodecyl sulfate with injection of deionized water in between the pre-treatments. The antibodies were diluted with 10 mM sodium acetate buffer pH 4.5 and coupled to the carboxymethylated dextran surface of the chip using the manufacturer instructions for amine-coupling chemistry. The remaining reactive groups on the surface were deactivated using ethanolamine-HCl. The mAb were captured on the sensor surface via Fc domain. The associations of human CD27 ECD injected at increasing concentrations (0.6-150 nM, 4-fold dilution series) were monitored for three minutes and the dissociations for ten minutes. Regeneration of capture surfaces to baseline was optimized using two 3 second pulses of 100 mM phosphoric acid. Data were processed using the Scrubber software, version 1.1 g (BioLogic Software). Double reference subtraction of the data was performed to correct for buffer contribution to the signal and instrument noise. The kinetic analysis of the processed data was carried out using the Biaevaluation 4.0.1 software (GE Healthcare Bio-Sciences, Uppsala, Sweden). Binding profiles were described by a 1:1 binding model indicating a monovalent binding of CD27.

TABLE 1

| mAb | Isotype | Biacore $K_D$ nM | IM-9 Binding[1] $IC_{50}$ ug/ml | NF-kβ Reporter $IC_{50}$[2] ug/ml | Agonism[3] at 50 ug/ml |
|---|---|---|---|---|---|
| C2177 | mIgG1 | 3.07 | 0.063 | 0.040 | 1.850 |
| C2186 | mIgG1 | 2.55 | 0.059 | 0.105 | 2.547 |
| C2191 | mIgG1 | 2.62 | 0.059 | 0.080 | 3.053 |
| C2192 | mIgG2a | 0.21 | 0.054 | 0.232 | 5.394 |

[1]$IC_{50}$ for mAb inhibition of IM-9 cells binding to immobilized CD27
[2]$IC_{50}$ for mAb inhibition in the reporter gene assay
[3]Agonist activity of mAbs at 50 ug/ml in the absence of CD70, measured as fold-increase in reporter gene signal relative to isotype control antibodies.

Inhibition of Cell Proliferation

The proliferation of T-cells sub-optimally activated in culture with anti-CD3 plus anti-CD28 antibodies is enhanced by CD70 ligation of CD27 expressed on the T-cells. The four murine neutralizing antibodies were assessed for their ability to inhibit T-cell proliferation in the presence of CD70 and to induce proliferation in the absence CD70. Frozen CD4+ T cells were purchased from AllCells, LLC. Cells were thawed and placed into IMDM medium containing 10% FBS, 1% 1-glutamine, and 1% Penicillin-Streptomycin. Prior to plating cells, anti-CD3 (OKT3) antibody was coated onto a U-bottom plate at 1 ug/☐mL in PBS overnight at 4° C. Cells were counted, brought to a concentration of $1\times10^6$ cells/mL, and plated at $1\times10^5$ cells/well. Soluble anti-CD28 was added as a secondary activation signal at 1 ug/mL per well. Irradiated (6000 rads) HEK cells transfected with either human CD70 or vector alone (mock) were added to appropriate wells at $2\times10^4$ cells/well (20%). Cells were stimulated for 3 days, 0.9 uCi thymidine [methyl-3H] was added to all sample wells and the cells were incubated for 18-24 hours. On the fourth day of stimulation, cells were harvested onto a filter plate using the PE Filtermate Harvester. The plate was allowed to dry and 30 uL of MicroScint™-20 was added to all sample wells. The plate was read on a PE TopCount NXT, and data collected was as CPM. Antibody C2177 shows dose-dependent inhibition of CD70 mediated T-cell proliferation and very weak intrinsic agonistic activity in the absence of CD70 (FIG. 1). Similar results were observed for the C2186, C2191 and C2192 antibodies. The $IC_{50}$ and maximal % inhibition for these antibodies are reported in Table 2. None of the antibodies showed consistent stimulation of proliferation in the absence CD70 ligation, indicating a lack of intrinsic agonist activity.

In addition, the C2177, C2186, C2191 and C2192 antibodies showed dose-dependent inhibition of CD70-mediated T-cell proliferation as measured in a CSFE assay with no effect on proliferation in the absence of CD70 stimulus. Frozen CD3+ T cells were purchased from AllCells, LLC. Cells were thawed and placed into IMDM medium containing 10% FBS, 1% L-glutamine, and 1% Penicillin-Streptomycin. Cells were pre-labeled with 2.5 mM CFSE (Invitrogen), quenched with FBS and washed with T cell media. CFSE is a dye that passively diffuses into cells and become highly fluorescent upon binding with intracellular amines. Upon cell division each daughter cell will contain half of the CFSE label of the parental cell, thus cell proliferation may be monitored by tracking numbers of cells with different CFSE intensity. The cells were brought to a concentration of $1\times10^6$ cells/mL, and plated at $1\times10^5$ cells/well. Prior to plating cells, anti-CD3 (OKT3) antibody was coated onto a U-bottom plate at 0.5 ug/mL in PBS overnight at 4° C. Soluble anti-CD28 was added as a secondary activation signal at 0.1 ug/mL per well. Irradiated (6000 rads) HEK cells transfected with either human CD70 or vector alone (mock) were added to appropriate wells at $2\times10^4$ cells/well (20%). Cells were stimulated for 4 days and analyzed by FACS analysis to count divided cells containing different intensity levels of CFSE label.

Inhibition of Plasma Blast Differentiation

The CD27-neutralizing hybridoma mAbs were also tested in a plasma blast differentiation assay with primary human B-cells. CD19+ human B lymphocytes that had been negatively selected from peripheral blood of normal donors (obtained from AllCells) were cultured for 6 days in the presence of either 1 ug/mL anti-CD40 antibody (clone MAB89, Abcam) and 100 ng/mL Interleukin 21 (Invitrogen) or 1 ug/mL soluble human recombinant CD40 ligand and 2 ug/mL 'enhancer for ligands' (both Alexis Biochemicals) and 100 ng/ml Interleukin 21 in 96-well plates at $10^5$ B cell per well. CD27-neutralizing hybridoma or isotype control antibodies were added in the presence or absence of $2\times10^4$ irradiated (6000 rads) CD70-expressing HEK 293 cells or MOCK-transfected HEK 293 cells. CD27-neutralizing hybridoma mAbs and matching isotype controls were used at 25, 2.5, and 0.25 ug/mL. On day 6, cell samples were analyzed by flow ☐cytometry and fractions of plasma blasts were identified as forward scattering/high, IgDminus, CD38bright, CD20low. The effect of CD27-neutralizing mab was calculated as plasma blast frequency in B-cell cultures containing CD70 expressing cells and hybridoma mabs normalized to plasma blast frequency in corresponding B-cell cultures containing mock-transfected cells. The percent inhibition by the C2177, C2186, C2191 or C2192 mAbs at 2.5 ug/mL is shown in Table 2. Agonistic activity in the absence of CD70 stimulus was not observed for any of these mAbs.

TABLE 2

| MAb | $IC_{50}$ ug/ml | T-Cell Proliferation - CD4+ Cells % Inhibition at highest concentration (30 ug/ml) (Mean ± SEM) | Plasma blast differentiation % Inhibition at 2.5 ug/ml (Mean ± SEM) |
| --- | --- | --- | --- |
| C2177 | 0.245 | 75.4 ± 4.1 (n = 6, 2 donors) | 78 ± 20 (n = 4) |
| C2186 | 0.775 | 65.3 ± 4.4 (n = 6, 2 donors) | 93 ± 27 (n = 4) |
| C2191 | 0.3 | 58.3 ± 6.0 (n = 6, 2 donors) | 105 ± 9 (n = 4) |
| C2192 | 0.445 | 75.7 ± 5.7 (n = 6, 2 donors) | 74 ± 0 (n = 2) |

Example 4: Epitope Mapping and Grouping

To more carefully evaluate the initial binning, competition assays were carried out with some of the purified neutralizing mAbs and with the CD27-neutralizing antibody, MAB 382 (R&D Systems). Briefly, 5 µl (10 µg/mL) of CD27-Fc chimeric protein (R&D Sysytems, Cat#382-CD) was coated on a MSD HighBind plate (Meso Scale Discovery, Gaithersburg, Md.) per well for 2 hr at RT. 5% MSD Blocker A buffer (Meso Scale Discovery, Gaithersburg, Md.) was added to each well and incubated for 2 hr at RT. Plates were washed three times with 0.1 M HEPES buffer, pH 7.4, followed by the addition of a mixture of 10 nM labeled CD27 antibody with different concentrations of a competitor antibody (1 nM to 2 uM). Antibodies were labeled with MSD Sulfo-Tag™ NHS-ester, an amine-reactive N-hydroxysuccinimide ester which couples to primary amine groups of proteins to form a stable amide bond. After a 2-hour incubation with gentle shaking at RT, plates were washed 3 times with 0.1M HEPES buffer (pH 7.4). MSD Read Buffer T was diluted with distilled water (4-fold) and dispensed at a volume of 150 µL/well. The plates were analyzed using a SECTOR Imager 6000 which detects electrochemiluminescence through Sulfo-Tag labels that emit light upon electrochemical stimulation initiated at the electrode surfaces of MSD microplates.

The competition studies defined three competition groups for the antibodies summarized in Table 3, confirming the initial binning assays. C2179, C2192 and MAB382 constitute one group; C2177, C2182, C2186 and C2193 are a second group; and C2191 constitutes a separate group.

TABLE 3

| Competitor | Labeled Antibody | | | | |
|---|---|---|---|---|---|
|  | C2179 | C2177 | C2182 | C2186 | C2191 |
| C2177 | − | + | + | + | − |
| C2179 | + | − | − | − | − |
| C2182 | − | +/− | + | + | − |
| C2186 | − | + | + | + | − |
| C2191 | − | − | − | − | + |
| C2192 | + | − | + | + | − |
| C2193 | − | +/− | + | + | − |
| MAB382 | + | − | − | − | − |

Example 5: Epitope and Paratope Identification by X-Ray Crystallography

The detailed epitopes and paratopes of antibodies C2177 and C2191 were determined by co-crystallization of their corresponding Fabs with CD27 ECD fragment (residues 1-101) as a trimeric complex and structure determination by X-ray crystallography. The His-tagged chimeric versions (mouse variable domain, human constant domain) of C2177 Fab and C2191 Fab were expressed in HEK293 cells and purified using affinity and size exclusion chromatography. The His-tagged ECD fragment (residues 1-101) of human CD27 was further purified by anion exchange chromatography. The ternary complex CD27:C2177 Fab:C2191 Fab was prepared by mixing CD27 with the excess of Fabs at a molar ratio 1:1.25:1.25. The complex was incubated for 2 h at 4° C., separated from the uncomplexed species using size-exclusion chromatography, and concentrated to 12 mg/mL in 20 mM Tris pH 8.5, 250 mM NaCl. Crystallization of the complex was carried out by the vapor-diffusion method in sitting drops at 20° C. The crystals of the complex were obtained from 24% PEG 3350, 0.2 M ammonium chloride, 0.1 M Tris buffer, pH 8.5. For X-ray data collection, one crystal was soaked for a few seconds in a cryoprotectant solution containing crystallization solution supplemented with 20% glycerol, and flash frozen in the stream of nitrogen at 100 K. Diffraction data were collected at the Rigaku MicroMax™-007HF X-ray generator equipped with a Saturn 944 CCD detector and an X-stream 2000 cryocooling system (Rigaku) over a 240° crystal rotation with 2-min exposures per 0.25°-image and were processed with the program XDS (Kabsch W. 2010. Acta Crystallogr. D66:125-132). The crystals belong to the monoclinic space group P21 with unit cell parameters: a=141.1 Å, b=53.0 Å, c=143.4 Å, $\alpha$=90°, $\beta$=112.2°, $\gamma$=90°.

Figure 2:
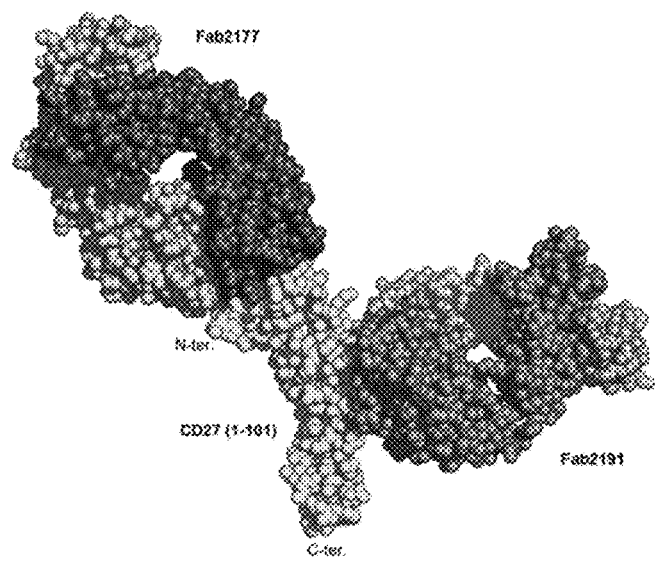
FIG. 2 shows the crystal structure of CD27:C2177:C2191 ternary complex. N- and C-termini of CD27 fragment are labeled. Heavy chains of Fabs are darker than their light chains.
Figure 3:
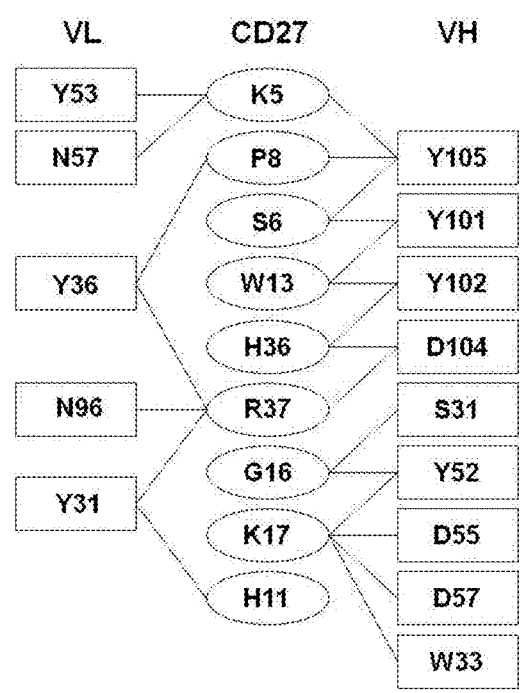
FIG. 3 is a diagram of CD27 protein-C2177 antibody contacts with CD27 protein residues (epitope) in circles and C2177 antibody residues (paratope) in boxes.

The crystal structure of the ternary complex was determined at 3.5 Å resolution and refined to the crystallographic R-factor of 26%. The Fabs of C2177 and C2191 bind CD27 at spatially distinct non-overlapping epitopes (FIG. 2). C2177 Fab binds the N-terminal (distal from the cell surface) portion of CD27. The epitope covers 700 Å2 and includes 9 residues: K5, S6, P8, H11, W13, G16, K17, H36, R37 (FIG. 3). The paratope is defined as antibody residues in contact (within 4 Å) with the antigen. The C2177 paratope includes 5 residues from VL (Y31, Y36, Y53, N57, N96) and 9 residues from VH (S31, W33, Y52, D55, D57, Y101, Y102, D104, Y105) (FIG. 3). All 6 CDRs are involved in antigen recognition. H36 and R37 are the central residues of the epitope. They stack against Y31 of VL and Y102 of VH; H36 also forms a salt bridge to D104 of VH.

Figure 4:
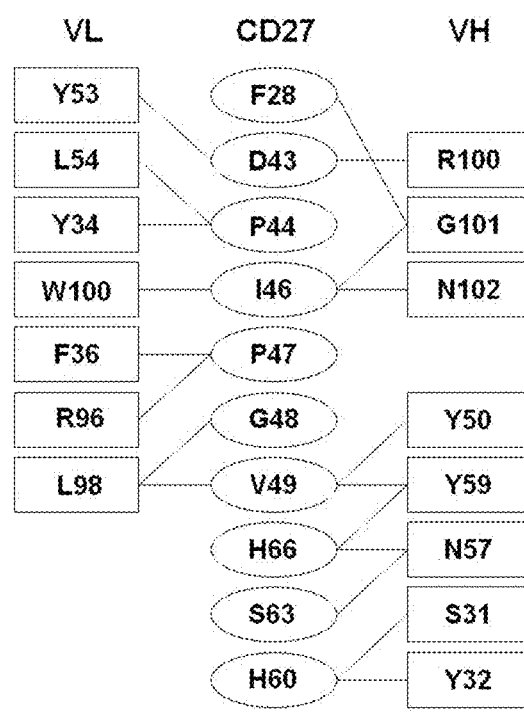
FIG. 4 is a diagram of CD27 protein-C2191 antibody contacts with CD27 protein residues (epitope) are in circles and C2191 antibody residues (paratope) in boxes.

C2191 Fab binds CD27 at the 'side' surface (FIG. 2) and covers 800 Å2 of the surface. The epitope includes 10 residues: F28, D43, P44, I46, P47, G48, V49, H60, S63, H66. The C2191 paratope includes 7 residues from VL (Y34, F36, Y53, L54, R96, L98, W100) and 8 residues from VH (S31, Y32, Y50, N57, Y59, R100, G101, N102) (FIG. 4). The antibody-antigen interactions are dominated by the hydrophobic interactions between residues 44-49 of CD27 and a hydrophobic patch at the VL CDRs.

The different location of the C2177 and C2191 epitopes suggests different mechanisms of action of these antibodies. C2191 probably directly competes with CD70 ECD for the overlapping epitopes on the 'side' surface of CD27. C2177 antibody, on the contrary, does not compete for the same epitope but rather prevents the approach of the cells bearing CD27 and CD70. This observation is supported by the fact that C2191 prevents binding of soluble CD70 ECD to CD27 whereas C2177 does not.

Example 6: Antibody Modulation of Human Lymphocyte Response

An immune deficient mouse model, NOD/SCID-IL2R$\gamma^{null}$ (NSG) mice, was developed to study aspects of the human immune system control by T-cell responses (Markus G Manz & James P Di Santo Renaissance for mouse models of human hematopoiesis and immunobiology Nature Immunology 10, 1039-1042 (2009)). Adoptive transfer of human PBMCs into immune-compromised (NSG) mice was employed to evaluate the effects of an anti-CD27 antibody on human cell engraftment and/or proliferation. The model allows the evaluation of the effects of targeting human CD27 on antibody production and T-cell mediated responses.

Antibodies C2177 and C2191 were administered at the time of cell transfer and then twice a week for 3 weeks. On day 21, the mice were sacrificed, cells were purified from blood and spleen and subsequently characterized by flow cytometry. CTLA4-Ig (Orencia, BMS) was included as a positive control for immune suppression. Human cell engraftment/expansion was measured by evaluating the presence of human $CD45^+$ cells in the blood and spleen samples.

The mice were closely monitored and the time of sacrifice was determined based on XGVH symptoms in accordance with animal welfare guidelines. The experimental readouts used to evaluate the effects of anti-CD27 treatment included: body weight (twice weekly), observable signs of XGVH (twice weekly), such as posture, activity level, grooming, skin lesions (in particular, around the eyes and ears) using 1-5 score system, absolute count of human cell subsets and activation status using flow cytometric analysis of (1) human PBMC injected, (2) mouse PB (once/week), and (3) spleen and bone marrow; determination of total human Ig, IgM and IgG in serum, spleen and BM using an ELISA, and, upon sacrifice, histology or immunohistochemistry to determine the levels of human infiltration in target organs, such as liver, kidney, lung and spleen.

The treatment groups were as follows:
1. PBMC (20 to 40 million cells per mouse, i.p.)
2. PBMC+CTLA4-Ig (10 mg/kg)
3. PBMC+Isotype control antibody, 2×/week for 3 weeks
4. PBMC+anti-CD27 antibody 2×/week for 3 weeks Mice dosed with 10 mg/kg anti-CD27 mAbs, C2177 and C2191, (hybridoma antibodies chimerized on a human IgG4 (ala/ala, ser->pro) scaffold) had statistically significant fewer human $CD45^+$ cells when compared to PMBC alone or isotype control in PMBCs isolated from the blood or spleen samples.

Example 7: Human Framework Adaptation of the C2177 and C2191 MABS

The antigen-binding site and the regions used to transfer the antigen specificity from antibodies C2177 and C2191 into the human FR's were reclassified as outlined in Raghunathan G. US20090118127 A1, 2009. In brief, the antigen-binding regions have been defined using various terms (review in Almagro and Fransson, *Front Biosci* 13: 1619-1633, 2008). The term "Complementarity Determining Regions (CDRs)" is based on sequence variability (Wu and Kabat, J. Exp. Med. 132:211-250, 1970). There are six CDRs; three for $V_H$ (H-CDR1, H-CDR2, H-CDR3), and three for VL (L-CDR1, L-CDR2, L-CDR3) (Kabat et al., Sequences of Proteins of Immunological Interest, 5th Ed. Public Health Service, National Institutes of Health, Bethesda, Md., 1991). "Hypervariable regions," "HVR's," or "HVL's" refers to the regions of an antibody variable domain which are variable in structure as defined by Chothia and Lesk (Chothia and Lesk, Mol. Biol. 196:901-917, 1987). There are six HVR's, three for VH (H1, H2, and H3) and three for VL (L1, L2, and L3).

In the HFA method, the regions targeted for transferring the specificity of the non-human antibody into the human FRs (HFRs) are the CDRs as defined by Kabat (Kabat et al., Sequences of Proteins of Immunological Interest, 5th Ed. Public Health Service, National Institutes of Health, Bethesda, Md., 1991) except in the region corresponding to the CDR-1 of $V_H$. For this region a combination of CDR and HVL (extended CDR-1 of $V_H$) are transferred from the non-human antibody into the human FRs (as provided in Tables 30, 31, 34, 35). In addition, variants with a shorter transferred CDR-H2 (called Kabat-7 [Raghunathan G. US20090118127 A1, 2009]) are generated and tested.

Human FR Selection.

Human FRs, defined as the regions in the V regions not comprised in the antigen-binding site, were selected from the repertoire of functional human germilne IGHV, IGKV, IGKJ and IGHJ genes. The repertoire of human germline gene sequences was obtained by searching IMGT database (Kaas, et al., Nucl. Acids. Res. 32, D208-D210, 2004; Lefranc M.-P et al., Nucl. Acids Res., 33, D593-D597, 2005) and compiling all "01" alleles as of Oct. 1, 2007. From this compilation, redundant genes (100% identical at amino acid level) and those with unpaired cysteine residues were removed from the compilation.

Initial selection of human sequences for HFR was based on sequence similarity of the human IGHV germline genes to the entire length of the mouse $V_H$ region including FR-1 to 3 as well as H-CDR-1 and H-CDR-2. In the next stage, the selected human sequences were rank ordered using a score that takes into account both the length of the CDRs and sequence similarities between CDRs of mouse and human sequences. A standard mutation matrix, such as the BLOSUM 62 substitution matrix (Henikoff and Henikoff, Proc Natl Acad Sci USA. 89, 10915-9, 1992) was used for scoring alignments of the CDRs of mouse and human sequences and a large penalty was applied if there was an insertion and/or deletion in the CDR loops. FR-4 was selected based on sequence similarity of the IGHJ germline genes (Kaas, et al., Nucl. Acids. Res. 32, D208-D210, 2004; Lefranc M.-P et al., Nucl. Acids Res., 33, D593-D597, 2005) with mouse antibodies C2177 and C2191 sequences. A similar procedure was used to choose human FRs for $V_L$. IGVK, germline genes were used for selecting FRs 1-3 and L-CDR 1-3. IGJK germline genes were used for selecting FR-4.

In addition to sequence criteria, a 3D homology model for the Fv fragments was constructed using Modeler (Sali and Blundell. J. Mol. Biol. 234: 779, 1993) in the program suite from Accelrys, Inc. The models were utilized for analysis of the HFR variants, including CDR characterization and assessment of developability liabilities. Additional considerations for selection of HFR variants were to minimize the number of exposed methionine and tryptophan residues, eliminate potential N-glycosylation sites and to favor human germlines with the highest expression profile in silico (de Wildt, J. Mol. Biol. 185: 895, 1999).

For path 1 framework adaptation and optimization of C2177, six $V_H$ and four $V_L$ HFR variants were included in the library. The $V_H$ and $V_L$ HFR variants were paired in a combinatorial manner to yield 24 HFR variant pairs plus 10 controls pairing all HFR variants with the counterpart V region of C2177 plus the parent C2177 itself to give a total of 35 combinations. Similarly for C2191, five $V_H$ and four $V_L$ HFR variants were paired in a combinatorial manner to yield 20 HFR plus 9 controls combining all HFR V variants paired with the counterpart V region of C2191 plus the parent C2191 parent itself for a total of 30 variants. DNA encoding the selected variable domains was recombined using standard methods to assemble complete MAbs with human IgG1 and kappa constant regions. The resulting reference chimeric antibody of C2177, designated M40, is comprised of variable regions H7 and L18. The corresponding chimeric antibody of C2191, designated M41, is comprised of variable regions H10 and L20. The mAbs were transiently expressed in 48-well plates in HEK 293E cells. Supernatant fluid from the cultures was tested for expression and binding activity 96 hours following transfection. The expression level of secreted mAb was evaluated using Octet technology to measure the rate of antibody binding to Protein A biosensors. The expression level was quantified by comparison to standard samples of known antibody concentration. An 8-point standard curve consisting of a 1:2 serial dilution of antibody of the identical isotype, was assembled, starting at 100 ug/ml. Biosensors were hydrated for 10 minutes in spent medium, and the binding rate of standards and unknown samples was measured for 2 minutes. Data was analyzed using the 5 parameter weighted dose-response equation and the initial slope binding rate algorithm. Samples with expression >1 ug/ml were diluted to 1 ug/ml with spent medium and screened using a single point ELISA. For this ELISA, 96 well black maxisorp plates were coated with 50 uL of 3 ug/ml goat anti human IgG FC diluted in carbonate-bicarbonate buffer, pH 9.4 at 4 C overnight and then washed three times with wash buffer (PBS with 0.05% Tween-20), blocked with 300 μl StartingBlock (Thermo Scientific) solution for 1 hour, then washed as before. Samples or standards were diluted to 100 ng/ml in spent medium, and 50 ul was added to the assay plate at room temperature for 1 hour with shaking. The plates were washed thrice and 50 ul per well of human CD27 ECD with His Tag was added at 60 ng/ml diluted in Assay Buffer (PBS with 1% FBS and 0.05% Tween-20) and incubated for 1 hour at room temperature. After washing, 50 ul per well of Qiagen peroxidase conjugated penta-his at 1:2000 dilution in assay buffer was added and incubated 1 hour at room temperature with shaking. The BM ChemiLum Substrate (BM Chemilum, POD, Roche) was mixed per manufacturer's instructions, and 50 ul was added to the plates after a final wash. After 10 minutes the plates are read on Perkin Elmer Envision Reader.

The results of screening the C2177 combinatorial library showed that all V-regions bind to CD27 with varying strengths. Several HFR variants gave a higher binding signal than the parent C2177 while others showed binding that was comparable or lower than the parent. All VLs bound antigen at detectable levels and did not influence binding HFR variants expressed at acceptable but lower levels than parent. Twenty-four of the C2177 HFR antibodies (VH, VL combinations) showed CD27 binding and expression >1 ug/ml.

The results of screening the C2191 combinatorial library showed that all except one VH bound to CD27 with varying signals. With the exception of pairing with this VH, all VLs showed binding to CD27. Several HFR variants gave a higher binding signal than the parent C2177, while others showed binding that was comparable or lower than the parent. Seventeen C2191 HFR antibodies (VH, VL combinations) demonstrated CD27 binding and expression >1 ug/ml.

Based on relative binding affinity for CD27 measured by ELISA, fifteen C2177 and eleven C2191 variants were chosen for pilot-scale expression and purification. Pilot-scale expression was done transiently in CHO-S cells at a volume of 750 ml. The harvested supernatants were purified via Protein A chromatography and the purified proteins were assessed for their affinity and functional activity.

The affinities of the HFR C2177 human MAb variants were measured by Surface Plasmon Resonance (SPR) using a ProteOn XPR36 protein interaction array system (Bio-Rad). The rates of CD27 association and dissociation were measured for each variant. The biosensor surface was prepared by covalently coupling Goat anti-Human IgG (Fc) antibodies to the surface of a GLC chip (BioRad) using the manufacturer instructions for amine-coupling chemistry. Approximately 5,000 RU (response units) of antibody were immobilized. The kinetic experiments were performed at 25° C. in running buffer (PBS, 0.01% P20, 0.01% BSA). 1:3 serial dilutions of human CD27 ECD from, starting at 300 nM were prepared in running buffer. About 350 RU of mAb were captured on each channel of the sensor chip. An isotype-matched antibody control was immobilized in channel 6 and used as a reference surface. Capture of mAb was followed by three minutes injection (association phase) of antigen at 30 uL/min, followed by 10 minutes of buffer flow (dissociation phase). The chip surface was regenerated by injection of 0.85% phosphoric acid at 100 uL/min. Data was processed on the instrument software. Double reference subtraction of the data was performed by subtracting the curves generated by buffer injection from the reference-subtracted curves for analyte injections. Kinetic analysis of the data was performed using 1:1 Langmuir binding model with global fit. The result for each mAb was reported in the format of $K_a$ (On-rate), $K_d$ (Off-rate), $K_D$ (Equilibrium dissociation constant), and percent activity. The affinities of the C2177 HFR variants were similar to the parent M40 mAb, showing less than a threefold change in $K_D$ for all variants. Similarly, the affinities of the HFR C2191 human mAb variants showed less than a two-fold difference from the parent M41 mAb.

The bioactivity of the HFR variants was measured by their inhibition of CD70-mediated induction of NFkB in a Luciferase reporter assay. HEK cells were transfected with an NFkB inducible luciferase expression vector pGL4-32-NFkB-Luc2 (Promega), and CD27 expression plasmid or empty vector and incubated overnight in Freestyle expression medium (Gibco, #12338). The next day cells were plated in 96-well culture plates in 40 uL, and 50,000 cells per well. Then, 40 uL antibodies or controls were added to cells using a serial dilution of 1:3, starting at 30 ug/ml final in-well concentration, and incubated for 1 to 2 hours. During this incubation, CD70 episomal cells are prepared for stimulation. Briefly, adherent cells were resuspended using standard cell culture techniques and incubated for 1 hour with Mitomycin C at 25 ug/mL to stop cell expansion. After incubation, CD70+ cells were washed in medium, diluted, and 40 uL was added at 10,000 cells per well. The plates were incubated overnight. The next day Steady Glo reagent (Promega) was prepared per the manufacturer's instructions and 120 uL was added per well. Plates were incubated at room temperature for 20 minutes while shaking. Luminescence was measured on a Perkin Elmer Envision Reader. The $IC_{50}$s of the C2177 HFR variants were similar to each other and to M40 parental MAb, ranging from 0.11 nM to 0.21 nM. The $IC_{50}$s of the C2191 HFR variants also were similar to each other and to the M41 parent, varying from 0.13 nM to 1.39 nM.

Consideration of affinity, bioactivity and biophysical properties led to the selection of the C2177 variant M69, comprised of the variable regions H28 (SEQ ID NO: 111) and L35 (SEQ ID NO: 82), and the C2191 variant M91, comprised of the variable regions H31 (SEQ ID NO: 131) and L42 (SEQ ID NO: 140), for affinity maturation. A summary of $K_D$s, purification yield, binding to CD27 ECD for the cell culture supernatants ("ELISA"), and inhibition ($IC_{50}$) of CD27 mediated NFκβ response by CD70 for the M40 parent and its M69 HFR variant and for the M41 parent and its M91 variant are shown in Table 4.

TABLE 4

| Protein ID | VH | VL | Proteon KD (nM) | Yield (mg) | ELISA signal | NFkB IC50 (nM) |
|---|---|---|---|---|---|---|
| C2177 parent | | | | | | |
| M40 | H7 | L18 | 0.96 | n.d. | 1.00 | 0.14 |
| M69 | H28 | L35 | 0.77 | 10.08 | 1.09 | 0.11 |
| C2191 parent | | | | | | |
| M41 | H10 | L20 | 10.3 | n.d. | 1.00 | 0.30 |
| M91 | H31 | L42 | 7.9 | 5.64 | 1.09 | 0.28 |

Example 8: Optimization of C2177 HFR MAB M69

M69 has an affinity around 1 nM to human CD27 ECD and contains the same CDRs as C2177, and the HFA parent CD27M40. Optimization of M69 involved multiple libraries to increase affinity and remove PTM sites introduced or identified in the process.

As described in Example 9, a parallel phage display library approach for HFR and optimization of C2177 identified diversity in the proline at position 52a of CDR-H2. This position was not randomized in the library design. The co-structure of the C2177 and C2191 Fabs with CD27 (Example 5) indicates that P52a is not directly involved in antigen binding. Nevertheless, mutation at this position could alter the CDR-H2 loop conformation and enable more optimal interactions with CD27 by surrounding residues D27. Thus, a library was designed to randomly diversify P52a and its neighboring residues Y52, G53 and D54 using NNK mutagenesis (library C27H28L2). Also in the path 2 optimization, a Y32 to F mutation in CDR-L1 showed improved binding. Thus, a second library was designed with random diversity in Y32 together with diversity in residues Y30a, D30d, A50, which lie in the same structural plane as Y32 (library C27L35L2).

In addition, the complete CDR-H3 and CDR-L1 loops were evaluated using libraries of limited diversity. Tables 5 and 6 show the design of these libraries.

TABLE 5

Limited diversity affinity maturation design for CDR-H3 (C27H28L3)

| VH Parent amino acid and position | Diversity |
|---|---|
| Ser95 | A, S |
| Asp96 | A, D |
| Tyr97 | A, D, S, Y |
| Tyr98 | A, D, S, Y |
| Gly99 | A, G |
| Asp100 | A, D |
| Tyr100a | A, D, S, Y |
| Gly100b | A, G |
| Phe100c | A, F, S, V |
| Ala101 | A, G |
| Tyr102 | A, D, S, Y |

TABLE 6

Limited diversity affinity maturation design for CDR-L1 (C27L35L3)

| VH Parent amino acid and position | Diversity |
|---|---|
| Lys24 | A, K, E, T |
| Ala25 | A, G |
| Ser26 | A, S |
| Gln27 | A, Q, E, P |
| Ser28 | A, S |
| Val29 | A, V |
| Asp30 | A, D |
| Tyr30a | A, D, S |
| Ala30b | A, G |
| Gly30c | A, G |
| Asp30d | A, D |
| Ser31 | A, S |
| Tyr32 | A, D, S |
| Met33 | A, M, T, V |
| Asn34 | A, N, D, T |

Fab libraries were constructed in a pIX phage Fab display system as described in WO2009/085462, Shi et al, J Mol Biol 397: 385-396 (2010), and Tornetta et al. J Immunol Methods 360: 39-46 (2010) with minor modifications to restriction enzyme sites. These libraries were panned against biotinylated CD27-ECD according to panning schemes known in the art, such as described in WO2009/085462 and in Shi et al, J Mol Biol 397: 385-396 (2010), directed to increasing affinity by selecting for a slower off-rate or faster on-rate. Phage was produced by helper phage infection. Binders were retrieved by addition of beads to form a bead/antigen/phage complex. After the final wash, phage was rescued by infection of exponentially growing TG-1 Escherichia coli cells. Phage was again produced and subjected for additional rounds of panning.

For follow-up screening, DNA was prepared from glycerol stocks of phage panning rounds and the pIX gene was excised by NheI/SpeI digestion. After ligation, the DNA was transformed into TG-1 cells and grown on LB/Agar plates overnight. The next day, colonies were picked, grown overnight, and the cultures used for (i) colony PCR and sequencing of the V-regions, and (ii) induction of Fab production. For Fab production, the overnight culture was diluted 10-100 fold in new media and grown for 5-6 hours at 37 degrees C. Fab production was induced by the addition of fresh media containing IPTG and the cultures were grown overnight at 30 degrees C. The following day, the cultures were spun down and the supernatants, containing the soluble Fab proteins, were used for Fab ELISA. For the ELISA, the soluble Fab proteins were captured onto plates by a polyclonal anti-Fd(CH1) antibody. After washing and blocking, biotinylated human CD27 ECD was added at 0.2 nM concentration. This concentration enables ranking of the Fab variants, defined as percent binding of the parent, in which the parent Fab, present as a control in all plates, is defined as 100% binding. The biotinylated CD27 ECD was detected by HRP-conjugated streptavidin and chemiluminescence read in a plate reader. At this concentration of CD27, ranking of the Fab variants, normalized to the parent Fab, is possible. By this criterion, 10 heavy and 6 light chains binding human CD27 at 100% or higher relative to M69 Fab were selected.

From the CDR-H2 library (C27H28L2), the parental Y was predominantly selected at position 52 indicating preference for this residue. At position 52a, P was replaced with A, S, V, and G residues among the Fabs with the best binding activity. At position 53, the parental G was selected along with R and N. At position 54, only the parental D was recovered. Nine clones from this library (Table 7) were subcloned into IgG vectors for expression and characterization as mAbs.

TABLE 7

Nine VH clones selected from full diversity library C27H28L2

| Peptide ID | Y52 | P52a | G53 | D54 |
|---|---|---|---|---|
| H237 | F | V | R | D |
| H238 | Y | V | G | D |
| H239 | Y | A | G | D |
| H240 | Y | A | R | D |
| H241 | Y | G | R | D |
| H242 | Y | A | N | D |
| H243 | Y | G | G | D |
| H244 | Y | S | G | D |
| H245 | Y | S | R | D |

For the CDR-H3 library (C27H28L3), the only diversity recovered was S95A and A101G. One clone from this library containing both mutations (Table 8) was subcloned into the IgG vectors for expression and characterization as a mAb.

TABLE 8

Single VH clone selected from C27H28L3

| Peptide ID | S95 | D96 | Y97 | Y98 | G99 | D100 | Y100a | G100b | F100c | A101 | Y102 |
|---|---|---|---|---|---|---|---|---|---|---|---|
| H236 | A | D | Y | Y | G | D | Y | G | F | G | Y |

For the four position L-CDR1 library (C27L35L2), position 30a showed enrichment of the parental Y and W. At position 30d, residues S, H, and E were enriched along with the parental D. At position 32, the parental Y was replaced with F and W. At position 50, T was preferred over the parental A. In general, the best clones had more hydrophobic side chains compared to parent. Five clones from this library (Table 9) were subcloned into IgG vectors for expression and characterization as mAbs.

For the complete CDR-L1 library with limited diversity (C27L35L3), only one sequence was recovered, with the only difference from parent being Y32 changed to F, similar to the four position VL library above. This complete CDR-L1 library did not include an F in position 32, and thus the recovered clone was likely a contaminant from the four position VL library. This clone (L255) was subcloned into the IgG vectors for expression and characterization as a mAb (Table 9).

TABLE 9

Six VL clones selected from C27L35L1 and C27L35L2

| Peptide ID | Y30a | D30d | Y32 | A50 |
|---|---|---|---|---|
| L255 | Y | D | F | A |
| L256 | Y | D | W | V |
| L257 | Y | D | W | T |
| L258 | Y | S | F | T |
| L260 | W | H | W | T |
| L261 | Y | S | F | E |

The 6 variant light chains were paired with the 10 variant heavy chains to give 60 combinations that were expressed HEK293E cells. Supernatants were screened for expression level, binding to human CD27 ECD as measured by ELISA, and affinity as measured on a ProteOn instrument. The expression level of all variants was sufficient for screening purposes. Affinity was increased up to 40-fold for some variants. Two mAbs M596 and M600, were selected for further mutagenesis to remove potential sites of post-translational modification. The VH and VL chain combinations for these mAbs are given in Table 10. The antibodies differ by only two residues in their light chains.

M596 differs from the parent molecule, M69, at three positions: P52aA in CDR-H2, Y32W in CDR-L1, and A50T in CDR-L2. M600 differs from M69 at two positions: P52aA mutation in CDR-H2 and Y32F in CDR-L1.

Three shared potential post-translational modification sites were identified in M596 and M600. There is a potential N-linked glycosylation site at position N58 in CDR-H2 and two potential isomerization sites in CDR-H2 and CDR-L1 encoded by "DG" and "DS," respectively. In addition, M596 contains a non-germline tryptophan residue in CDR-L1 that could be susceptible to oxidation.

To remove the glycosylation risk, three individual single substitutions were created at N58 and one at S60 (Table 11). The constructs were expressed in HEK293E cells and supernatants were evaluated for affinity to CD27 using the ProteOn instrument. All of the variants had affinities close to those of the parents which were 25 pM and 49 pM for M596 and M600, respectively. Variants M680 and M678, both derived from M600, were selected for evaluation of further substitutions to eliminate the isomerization sites. Variants M680 and M678 have A at positions 60 and 58, respectively, and have the additional advantage of lacking the tryptophan in CDR-L1 that was present in the M596 parent.

TABLE 11

| VH Parent amino acid and position | Diversity |
|---|---|
| Asn58 | N, A, R, T |
| Ser60 | S, A |

To evaluate the impact of mutating the potential isomerization sites in M678 and M680, a small library was designed to remove both sites in parallel. Each mutation was substituted individually into CDR-H2 of the heavy chains or CDR-L1 of the common light chain and then paired in a combinatorial library. The diversity of this library is shown in Table 12.

TABLE 10

Heavy and light chain pairing of selected C2177 affinity matured leads

| Antibody ID | Light Chain Peptide ID | CDR-L1 (SEQ ID NO) | CDR-L2 (SEQ ID NO) | Heavy Chain Peptide ID | CDR-H2 (SEQ ID NO) |
|---|---|---|---|---|---|
| M596 | L257 | KASQSVDYAGDSWMN (26) | TASNLES (39) | H239 | RIYAGDGDTN (residues 1-10 of 15) |
| M600 | L255 | KASQSVDYAGDSFMN (25) | AASNLES (37) | H239 | RIYAGDGDTN (residues 1-10 of 15) |

TABLE 12

| VH Parent amino acid and position | Diversity |
|---|---|
| Asp54 | D, E |
| Gly55 | G, A |
| VL Parent amino acid and position | |
| Asp34 | D, E |

These mAbs were expressed and affinity was evaluated as for the glycosylation site variants. The D34E mutation in the CDR-L1 potential isomerization site led to a consistent two-fold increase in affinity and therefore this site was successfully removed. The D54E mutation in the CDR-H2 potential isomerization site lowered the affinity more than tenfold. However, the G55A mutation did not significantly affect the affinity. Variants M703 and M706 retain the affinity of the M600 parent and have a reduced risk of impact on function from PTM. Table 13 shows the selected variants from each stage of the PTM-risk assessment, their heavy and light chain pairing, affinity, and sequence modifications in the CDRs. The mutation selected to remove the potential glycosylation site is underlined. The mutations to remove the two potential isomerization sites are bolded and double underlined.

TABLE 13

| mAb ID | VH | VL | KD (pM) | CDR-H2 (SEQ ID NO) | CDR-L1 (SEQ ID NO) |
|---|---|---|---|---|---|
| M596 | H239 | L257 | 25 | RIYAGDGDTNYSPSFQG (165) | KASQSVDYAGDSWMN (26) |
| M600 | H239 | L255 | 49 | RIYAGDGDTNYSPSFQG (165) | KASQSVDYAGDSFMN (25) |
| M678 | H259 | L255 | 53 | RIYAGDGDTAYSPSFQG (166) | KASQSVDYAGDSFMN (25) |
| M680 | H260 | L255 | 30 | RIYAGDGDTNYAPSFQG (167) | KASQSVDYAGDSFMN (25) |
| M703 | H270 | L267 | 28 | RIYAGDADTAYSPSFQG (168) | KASQSVDYAGESFMN (29) |
| M706 | H272 | L267 | 13 | RIYAGDADTNYAPSFQG (169) | KASQSVDYAGESFMN (29) |

Example 9: Combinded HFR and Optimization of C2177 MAB

In this approach, a limited set of HFR variants were evaluated in a Fab format for expression, pIX display and binding and the best candidates were then advanced into optimization. CDRs from C2177 were human framework adapted into two heavy chains VH5-51 (SEQ ID NO: 102 H24) and VH1-46 (SEQ ID NO: 106 H25) and two light chains Vk4-1 and Vk012 (SEQ ID NO: 90 L36). These HFA variable domains were paired together in a 2×2 matrix as Fabs with human CH1 and Ck constant regions in the Fab pIX phage display vector. The VH1-46/Vk012 variant (M55, H25/L36) showed binding to CD27 and good display characteristics and was selected for construction of affinity maturation libraries.

The Fab libraries for pIX phage display were constructed as described above for Example 8. Based on the experimental co-structure of CD27 with C2191 and C2177 (Example 5), diversity libraries were designed in CDR residues in and around the antibody paratope. The emphasis on variation was in CDRs L1, L3, and H2. A total of 4-6 residues within an individual CDR were diversified with an NNK codon, encoding for all 20 amino acids. The size of each library was estimated to ≤6×10$^7$ variants, which can be covered using standard library restriction endonuclease cloning techniques. Table 14 shows the residues that were subjected to full diversification in the different CDR libraries.

TABLE 14

Affinity maturation library design for C2177

| | Parent amino acid and position |
|---|---|
| VH CDR | |
| CDR-H2 | Y52 |
| | G53 |
| | D54 |
| | D56 |
| | N58 |
| CDR-H3 | Y97 |
| | Y98 |
| | D100 |
| | Y100a |
| VL CDR | |
| CDR-L1 | Y30a |
| | A30b |

TABLE 14-continued

Affinity maturation library design for C2177

| | Parent amino acid and position |
|---|---|
| | G30c |
| | D30d |
| | Y32 |
| CDR-L3 | Q90 |
| | N92 |
| | E93 |
| | D94 |
| | Y96 |

Fab libraries displayed on phage coat protein IX were panned against biotinylated hCD27ECD/Fc. Phage was produced by helper phage infection of a plasmid library of the variants. Binders were retrieved by addition of streptavidin-coated magnetic beads to form a bead/antigen/phage complex. After the final wash, phage was rescued by infection of exponentially growing MC1061F' *Escherichia coli* cells. Phage was again produced and subjected for additional rounds of panning. Soluble Fab from selected clones was produced and evaluated for binding activity as described about for Path 1. Hits were obtained only from the CDR-L1 and CDR-L2 libraries. Twenty-one clones from these two libraries demonstrated binding greater than that of the parent HFR Fab. Clones containing C or M in the diversified sequences were discarded. Ten Fabs were converted for expression in a IgG4SPAAa/kappa background for further characterization. The IgG4PAA heavy chain is human IgG4 containing a serine to proline substitution in the hinge region (Angal et al., Mol Immunol 30: 105 (1993) and alanine substitutions at two positions in CH2 (M L Alegre et al, Transplantation; 57: 1537-43 (1994)). The mAbs were produced in HEK293E cells as replicas of the Fabs and as a matrix of heavy and light chain combinations. Affinity was measured on a ProteOn instrument using the culture supernatants (Table 15). Mutation of P52a to Q (M158) or S (M157) in CDR-H2 decreased the $K_D$ 6-fold compared to that of the parental mAb (M159). The Y36F mutation in CDR-L1 (M149) decreased $K_D$ 4-fold and the addition of G33H and D34E mutations (M155) led to a 6-fold decrease in $K_D$. Combination of the P52S mutation with either Y36F (M160) or Y36F plus G33H and D34E decreased the $K_D$ 20-fold to 100 pM. The combinations of substitutions in M158, M160 and M166 were selected for further characterization.

TABLE 15

Initial panel of mAbs derived from Fab maturation libraries

| Protein DNA ID | H&L | CDR-H2 (SEQ ID NO) | CDR-L1 (SEQ ID NO) | $K_D$ (nM) |
|---|---|---|---|---|
| M149 | H25, L219 | RIYPGDGDTNYNGKFKG (3) | KASQSVDYAGDSFMN (25) | 0.54 |
| M150 | H25, L218 | RIYPGDGDTNYNGKFKG (3) | KASQSVDYFGDSLMN (32) | 4.04 |
| M151 | H25, L224 | RIYPGDGDTNYNGKFKG (3) | KASQSVDYYNSSFMN (36) | 1.07 |
| M152 | H25, L223 | RIYPGDGDTNYNGKFKG (3) | KASQSVDYWSDSFMN (35) | 1.54 |
| M153 | H25, L222 | RIYPGDGDTNYNGKFKG (3) | KASQSVDYVGTSFMN (34) | 1.41 |
| M154 | H25, L221 | RIYPGDGDTNYNGKFKG (3) | KASQSVDYFRTSFMN (33) | 1.56 |
| M155 | H25, L217 | RIYPGDGDTNYNGKFKG (3) | KASQSVDYAHESFMN (31) | 0.37 |
| M156 | H25, L216 | RIYPGDGDTNYNGKFKG (3) | KASQSVDYFSESFMN (170) | 0.71 |
| M157 | H197, L220 | RIYQGDGDTNYNGKFKG (22) | KASQSVDYAGDSYMN (24) | 0.39 |
| M158 | H196, L220 | RIYSGDGDTNYNGKFKG (19) | KASQSVDYAGDSYMN (24) | 0.36 |
| M159 | H25, L220 | RIYPGDGDTNYNGKFKG (3) | KASQSVDYAGDSYMN (24) | 2.23 |
| M160 | H196, L219 | RIYSGDGDTNYNGKFKG (19) | KASQSVDYAGDSFMN (25) | 0.12 |
| M161 | H196, L218 | RIYSGDGDTNYNGKFKG (19) | KASQSVDYFGDSLMN (32) | 1.34 |
| M162 | H196, L224 | RIYSGDGDTNYNGKFKG (19) | KASQSVDYYNSSFMN (36) | 0.43 |
| M163 | H196, L223 | RIYSGDGDTNYNGKFKG (19) | KASQSVDYWSDSBFMN (35) | 0.30 |
| M164 | H196, L222 | RIYSGDGDTNYNGKFKG (19) | KASQSVDYVGTSFMN (34) | 0.27 |
| M165 | H196, L221 | RIYSGDGDTNYNGKFKG (19) | KASQSVDYFRTSFMN (33) | 0.18 |
| M166 | H196, L217 | RIYSGDGDTNYNGKFKG (19) | KASQSVDYAHESFMN (31) | 0.10 |
| M167 | H196, L216 | RIYSGDGDTNYNGKFKG (19) | KASQSVDYFSESFMN (170) | 0.91 |

M158, M160 and M166 proteins were produced in 750 mL cultures of HEK293 cells, purified, and analyzed for binding kinetics to CD27-His on Biacore. The $K_D$ values were about 1 log higher than those measured by ProteOn with crude supernatants but showed the same values relative to each other (Table 16).

TABLE 16

| mAb ID | $k_{on}$ (M$^{-1}$s$^{-1}$) | $k_{off}$ (s$^{-1}$) | $K_D$ (pM) |
|---|---|---|---|
| M158 | (1.5 ± 0.03)E+06 | (6.6 ± 1.7)E−04 | 439 ± 114 |
| M160 | (1.6 ± 0.15)E+06 | ((1.8 ± 0.01)E−04 | 117 ± 11 |
| M166 | (1.62 ± 0.04)E+06 | (2.03 ± 0.16)E−04 | 126 ± 11 |

When re-evaluating the original HFA combinations, the VH5-51 adapted VH showed a 2-fold lower $K_D$ than the VH1-46 scaffold. The P52aS mutation in H-CDR2 was introduced into the VH5-51 VH creating H221. H221 was expressed with the L220, L219 and L217 light chains from the HFA parental mAb (M159) and the affinity improved variants M160 and M166, respectively, to generate mAbs M171, M169 and M170. BIAcore kinetic measurements on the purified mAbs showed a two-fold improvement in $K_D$ in comparison to the corresponding VH1-46 variants (compare Tables 16 and 17).

TABLE 17

| mAb ID | H/L Peptide ID | $K_{on}$ Ave (M$^{-1}$s$^{-1}$) | $K_{off}$ Ave (s$^{-1}$) | $K_D$ Ave (pM) |
|---|---|---|---|---|
| M169 | H221, L219 | (1.48 ± 0.13)E+06 | 1.02 ± 0.07)E−04 | 69 ± 8 |
| M170 | H221, L217 | 1.66E+06 | 1.16E−04 | 70 |
| M171 | H221, L220 | 1.53E+06 | 3.58E−04 | 234 |

Sequence analysis of M160, M169 and M170 identified a potential isomerization site at D54-G55 and a potential deamidation site at N61-G62 in CDR-H2 of H196 and H221. Additionally, a potential isomerization site was identified at D34 within CDR-L1 of L219. Mutations were introduced to remove these sites and evaluated for their impact on activity (Table 18). Purified mAbs were analyzed for affinity to CD27-His on ProteOn. The mutations either had no effect or a positive effect on $K_D$. For example, both M668 and M671 had almost 2 fold lower $K_D$s than their parental mAbs, M160 and CM169, respectively.

TABLE 18 mAb variants with PTM sequences mutated

| Parent mAb | mAb ID | H/L Peptide ID | CDR-H2 (SEQ ID NO) | CDR-L1 (SEQ ID NO) | $k_{on}$ Ave (M$^{-1}$s$^{-1}$) | $k_{off}$ Ave (s$^{-1}$) | $K_D$ Ave (pM) |
|---|---|---|---|---|---|---|---|
| M160 | M160 | H196, L219 | RIYSGDGDTNYNGKFKG (19) | KASQSVDYAGDSFMN (25) | 2.07E+06 | 2.23E−04 | 108 |
| M166 | M166 | H196, L217 | RIYSGDGDTNYNGKFKG (19) | KASQSVDYAHESFMN (31) | 1.84E+06 | 2.34E−04 | 127 |
| M169 | M169 | H221, L219 | RIYSGDGDTNYNGKFKG (19) | KASQSVDYAGDSFMN (25) | 2.36E+06 | 1.39E−04 | 59 |
| M160 | M668 | H255, L266 | RIYSGDADTNYAQKFKG (20) | KASQSVDYAGESFMN (29) | 2.14E+06 | 1.29E−04 | 60 |
| M160 | M669 | H256, L266 | RIYSGDADTNYNQKFKG (21) | KASQSVDYAGESFMN (29) | 2.49E+06 | 1.45E−04 | 58 |
| M169 | M670 | H257, L266 | RIYSGDADTNYAQKFKG (20) | KASQSVDYAGESFMN (29) | 1.73E+06 | 1.13E−04 | 65 |
| M169 | M671 | H258, L266 | RIYSGDADTNYNQKFKG (21) | KASQSVDYAGESFMN (29) | 2.52E+06 | 9.73E−05 | 39 |
| M166 | M672 | H255, L217 | RIYSGDADTNYAQKFKG (20) | KASQSVDYAGESFMN (29) | 1.83E+06 | 2.64E−04 | 144 |
| M166 | M673 | H256, L217 | RIYSGDADTNYNQKFKG (21) | KASQSVDYAGESFMN (29) | 1.89E+06 | 1.89E−04 | 100 |

Example 10: Optimization of C2191 HFR MAB M91

The methods applied for the optimization of the M91 (H31/L42) were as described in Example 8, except as noted. An alanine/germline scan of the CDRs of C2191 was carried out in a Fab format to evaluate positions important for interaction with CD27, using the C2191 parent VH and VL regions in a Fab format with human Ch1 and Ck constant regions. The libraries replaced the residues in the CDRs with alanine or the residue present in the corresponding germline sequence. Some positions in the CDRs were excluded as they had low or no solvent exposure based on modeling and subsequently on the determined structure (Example 5). Putative somatic mutations were back-mutated to mouse germline amino acids to assess their contribution to antibody affinity. Briefly, the mouse V regions were cloned into the Fab pIX display vector and the binding of the parent to biotinylated human CD27-ECD protein was verified by ELISA. Single mutations (according to the library design) were introduced by site-directed mutagenesis, performed essentially as described by Stratagene (La Jolla, Calif., USA). Sequence confirmed mutants were cherry-picked into new plates and grown together with parental Fab and negative control Fabs. The final single amino-acid-substitution variants were generated in E. coli, and then screened for expression and CD27 binding by ELISA. The expression and binding signals for the parent clones were averaged and set to 1.0 and the signals of the mutants were normalized relative to the parent. Two forms of antigen were used in the ELISAs: CD27 ECD (1-173 residues) and CD27 ECD-Fc chimera (R&D Systems).

The results of this scan coupled with co-crystal structure provided the basis for design of affinity maturation libraries. For the heavy chain; the positions selected for variation were T33 in H-CDR1 and Y50, S52, S52a, N56 and Y58 in CDR-H2 (Table 23). T33 is not a contact residue but a T33A mutation improved binding. Positions S52 and S52a are not contact residues but the substitutions in the scan showed some increased binding. The tyrosines at positions 50 and 58 are both contact sites and substitutions at these sites were selected in the parallel optimization path described in Example 11. Position N56 was not evaluated in the alanine/germline scan but it is a contact site and adjacent to T33, S52, and S52a in the crystal structure. For the light chain, the positions selected for variation were T30a, S30b, G30c and Y30d in CDR-L1 and L50 and N53 in CDR-L2 (Table 23). None of these residues contact antigen directly but are adjacent to residues that are in contact which the scan showed had substantial negative impact on binding. A L50A mutation had a moderate effect on binding and, in the crystal structure, is the only residue in CDR-L2 likely in contact with antigen. In addition, N53 was selected for limited diversification. Two parallel libraries were constructed, one with Y30d mutated to W, and another with Y30d kept as Y, since W could make the paratope more hydrophobic and thus less developable. Tables 19 and 20 below show the VH and VL affinity maturation library designs for M91.

TABLE 19

| 2191 | HC_CDR1 | | | HC_CDR2 | | |
|---|---|---|---|---|---|---|
| Antigen contact? | No | Yes | No | No | Yes | Yes |
| Position in HC (SEQ ID NO: 131) | T33 | Y50 | S52 | S52a | N56 | Y58 |
| Position in HC (SEQ ID NO: 131) | T33 | Y50 | S52 | S53 | N57 | Y59 |
| Sequence Diversity | All 20 amino acids | Y A W H | All 20 amino acids | All 20 amino acids | All 20 amino acids | Y I L W |

TABLE 20

| 2191 | LC_CDR1 | | | | LC_CDR2 | |
|---|---|---|---|---|---|---|
| Antigen contact | No | No | No | Yes | Yes | No |
| Position in LC (SEQ ID NO: 140) | T30a | S30b | G30c | Y30d | L50 | N53 |
| Position in LC (SEQ ID NO: 140) | T31 | S32 | G33 | Y34 | L54 | N57 |
| Sequence Diversity | All 20 amino acids | All 20 amino acids | G R | Y* W* | All 20 amino acids | N K R |

*Two separate libraries containing either Y or W at this position were created

Fab libraries displayed on phage coat protein IX were panned against biotinylated CD27-ECD. A total of 12 heavy and 12 light chain variants were selected that bound to CD27 equally or better than the parental chimeric Fab of C2191. The variants were converted to IgG1/kappa antibodies, produced in HEK293E cells as 144 combinations, and culture supernatants were evaluated for binding by ProteOn. Significant increases (>100-fold) in affinity were observed for some variants. Of the 144 VH and VL pairings, 8 were selected for further characterization (Table 21). These mAbs were classified into three sub-groups: Group 1 variants have the same heavy chain (H227, SEQ ID NO: 133) paired with four different light chains, while Group 2 and Group 3 each have one light chain paired with two different heavy chains. The four selected light chains varied at all four positions diversified in CDR-L1 (RASKSVSX$_1$X$_2$X$_3$X$_4$SFMH) (SEQ ID NO: 158); where X$_1$ is A, E, H, or L; X$_2$ is D, G, V, or W; X$_3$ is G or R; and X$_4$ is W or Y). They also varied in both positions diversified in CDR-L2 (X$_1$ASX$_2$LES) (SEQ ID NO:171); where X$_1$ is L or V; and where X$_2$ is K, N, or R). CDR-L3 was unaltered from the L42 sequence (SEQ ID NO: 140) and is QHSRELPWT.

TABLE 21

Pairing of heavy and light chain sequences of selected 2191 affinity matured leads

| Antibody ID | Light Chain Peptide ID | CDR-L1 (SEQ ID NO:) | CDR-L2 (SEQ ID NO:) | Heavy Chain Peptide ID | CDR-H1 (SEQ ID NO:) | CDR-H2 (SEQ ID NO:) |
|---|---|---|---|---|---|---|
| M427 | C27L244 | RASKSVSAWGYSFMH (60) | VASRLES (68) | C27H227 | GFTFSSYGMS (44) | YIDEGGGQTIYPDSVKG (47) |

TABLE 21-continued

Pairing of heavy and light chain sequences of selected 2191 affinity matured leads

| Antibody ID | Light Chain Peptide ID | CDR-L1 (SEQ ID NO:) | CDR-L2 (SEQ ID NO:) | Heavy Chain Peptide ID | CDR-H1 (SEQ ID NO:) | CDR-H2 (SEQ ID NO:) |
|---|---|---|---|---|---|---|
| M429 | C27L245 | RASKSVSHVRWSFMH (61) | LASKLES (69) | C27H227 | GFTFSSYGMS (44) | YIDEGGGQTIYPDSVKG (47) |
| M488 | C27L249 | RASKSVSEGRWSFMH (62) | VASRLES (68) | C27H227 | GFTFSSYGMS (44) | YIDEGGGQTIYPDSVKG (47) |
| M489 | C27L250 | RASKSVSLDRWSFMH (63) | LASNLES (67) | C27H227 | GFTFSSYGMS (44) | YIDEGGGQTIYPDSVKG (47) |
| M492 | C27L249 | RASKSVSEGRWSFMH (62) | VASRLES (68) | C27H228 | GFTFSSYSMS (45) | YIDAGGGFTIYPDSVKG (48) |
| M493 | C27L250 | RASKSVSLDRWSFMH (63) | LASNLES (67) | C27H228 | GFTFSSYSMS (45) | YIDAGGGFTIYPDSVKG (48) |
| M501 | C27L250 | RASKSVSLDRWSFMH (63) | LASNLES (67) | C27H231 | GFTFSSYSMS (45) | HIDAGGGRTWYPDSVKG (49) |
| M526 | C27L249 | RASKSVSEGRWSFMH (62) | VASRLES (68) | C27H222 | GFTFSSYGMS (44) | YIDRGGGVTIYPDSVKG (50) |

These eight variants were produced by transient expression in HEK293E cells in a volume of 750 ml. The harvested supernatants were purified via Protein A chromatography, and each variant was analyzed by SDS-PAGE and SE-HPLC to determine purity of the sample and percentage of monomer in the purified sample. All of the variants were greater than 90% pure and greater than 90% monomeric. To evaluate association properties of the antibodies, retention factors (k') were determined by performing cross-interaction chromatography for each purified variant (Jacobs S A, Wu S J, Feng Y, Bethea D & O'Neil K T (2010) Cross-interaction chromatography: a rapid method to identify highly soluble monoclonal antibody candidates. *Pharm Res* 27, 65-71). In this method, sample antibodies were passed through a column coupled with human IgG and evaluated for retention relative to control antibodies. Briefly, 50 mg of human IgG (Sigma Aldrich) were coupled to a 1 mL NHS-Sepharose column (GE Healthcare) following the manufacturer's instructions. Uncoupled IgG was removed by washing with 0.1M Tris, pH 8, 0.5M NaCl and unreacted NHS groups were blocked with the same buffer. The coupling efficiency was determined by measuring the protein concentration remaining in the unreacted coupling buffer and washes using Pierce's Coomassie Plus Assay Kit (Thermo Pierce) and subtracting from the amount of protein before immobilization. A control column was also prepared using the same protocol but without conjugation of IgG to the resin. The control column was run first on a Dionex UltiMate 3000 HPLC after being equilibrated with PBS, pH Tat a flow rate of 0.1 mL/min. 20 µL of the stock protein solution was injected first to ensure non-specific binding sites were blocked followed by 20 µL of 10% acetone to check the integrity of the column. Samples to be analyzed were diluted to 0.1 mg/mL in PBS, pH 7. 20 uL of each sample was injected onto each column and allowed to run at 0.1 mL/min for 30 min. Retention times were recorded and the retention factor (k') was calculated for each variant. The k' value was calculated as the difference in the retention times on the IgG and blank columns. All of the variants were purified to greater than 90% purity based on SDS-PAGE and SE-HPLC. All k' values were calculated to be less than 0.3, indicative of good solution properties (Table 22).

TABLE 22

Batch analysis of purified affinity matured variants

| Antibody ID | HC | LC | Conc. (mg/ml) | Total Protein | % Monomer | Gel | k' |
|---|---|---|---|---|---|---|---|
| M427 | H227 | L244 | 1.42 | 15.63 | 100 | ok | 0.02 |
| M429 | H227 | L245 | 0.97 | 10.21 | 100 | ok | 0.07 |
| M488 | H227 | L249 | 2.00 | 27.06 | 98.9 | ok | 0.07 |
| M489 | H227 | L250 | 1.59 | 23.03 | 100 | ok | 0.17 |
| M492 | H228 | L249 | 2.07 | 27.96 | 97.4 | ok | 0.25 |
| M493 | H228 | L250 | 0.58 | 8.12 | 100 | ok | 0.24 |
| M501 | H231 | L250 | 2.01 | 26.08 | 100 | ok | 0.28 |
| M526 | H222 | L249 | 0.90 | 10.74 | 100 | ok | 0.10 |

The eight variant mAbs and the HFR parent were evaluated for their affinity to CD27 ECD by BIAcore and their $IC_{50}$ in the κβ-reporter assay. Kinetic constants and affinity were measured by BIAcore. Table 23 summarizes the data collected on these variants. The expression and ELISA signal for binding to CD27 as measured from the initial small culture supernatants are also included in this table.

TABLE 23

C2191 AM library subset data summary

| Protein ID | Expression (ug/ml) | ELISA signal | NFκβ $IC_{50}$ (pM) | $k_a$ | $k_d$ | $K_D$ (pM) |
|---|---|---|---|---|---|---|
| M41 | n.d. | n.d. | 45 | 6.20E+05 | 8.44E-03 | 13650 |
| M427 | 14.6 | 0.93 | 19 | 7.18E+05 | 3.00E-05 | 41.7 |
| M429 | 16.1 | 0.86 | 42 | 6.62E+05 | 2.02E-05 | 30.4 |
| M488 | 20.7 | 0.92 | 23 | 1.01E+06 | 3.96E-05 | 39.4 |
| M489 | 24.2 | 0.96 | 41 | 9.06E+05 | 2.18E-05 | 24.1 |
| M492 | 20.1 | 0.77 | 15 | 1.03E+06 | 1.47E-04 | 142.0 |
| M493 | 24.5 | 0.85 | 14 | 7.23E+05 | 1.05E-04 | 145.0 |
| M501 | 30.9 | 0.77 | 4 | 8.31E+05 | 6.16E-05 | 74.2 |
| M526 | 14.3 | 0.69 | 6 | 1.00E+06 | 1.71E-04 | 171.0 |

Example 11: Combined HFR and Optimization of C2191 MAB

In this approach, a limited set of HFR variants were evaluated in a Fab format for expression, pIX display and binding and the best candidates were then advanced into optimization. CDRs from C2191 were human framework adapted into two heavy chains (VH3-23 and VH3-11) and two light chains (Vk4-1 and Vk012). These HFA variable domains were paired together in a 2×2 matrix as Fabs with human CH1 and Ck constant regions in the Fab pIX phage display vector. The VH3-23Nk012 variant (H39 (SEQ ID NO: 145)) and L40 (SEQ ID NO: 137) showed binding to CD27 and good display characteristics and was selected for construction of affinity maturation libraries. This Fab is referred to as "parent."

For selection of antibodies with improved affinity, multiple residues in all CDRs except CDR-H3 of H39 were fully diversified using NNK degenerate codons (Table 24). Each CDR library was constructed separately and subjected to phage panning for selection of affinity matured variants.

TABLE 24

Affinity maturation library design for C2191 variants

| | Parent amino acid and position |
|---|---|
| VH CDR | |
| CDR-H2 | Y50 |
| | S52 |
| | S53 |
| | N56 |
| | Y58 |
| CDR-H3 | H95 |
| | R96 |
| | G97 |
| | N98 |
| | P99 |
| VL CDR | |
| CDR-L1 | T30a |
| | S30b |
| | G30c |
| | Y30d |
| | F32 |
| CDR-L2 | L50 |
| | A51 |
| | S52 |
| | N53 |
| | L54 |
| | E55 |
| | S56 |
| CDR-L3 | H90 |
| | R92 |
| | E93 |
| | L94 |
| | Y96 |

The C2191 libraries with diversity in CDR-H2, CDR-L1 or CDR-L2 yielded 50 unique Fabs with improved binding to human CD27 relative to the parental HFR Fab as measured in the single point ELISA. These clones were further ranked in a multi-point ELISA and seventeen clones were selected for conversion to human IgG4alaala/kappa for further characterization (Table 25).

TABLE 25

Affinity matured Fabs selected for conversion to IgG

| Fab ID | HC Peptide ID | LC Peptide ID | CDR-H2 (SEQ ID NO:) | CDR-L1 (SEQ ID NO:) | CDR-L2 (SEQ ID NO:) |
|---|---|---|---|---|---|
| Parent | H39 | L40 | YISSGGGNTYYPDSVKG (46) | RASKSVSTSGYSFMH (59) | LASNLES (67) |
| F116 | H39 | L59 | YISSGGGNTYYPDSVKG (46) | RASKSVSTSGYSFMH (59) | VGNRLED (70) |
| F119 | H39 | L62 | YISSGGGNTYYPDSVKG (46) | RASKSVSTSGYSFMH (59) | VGDRRQE (71) |
| F178 | H145 | L40 | YISGGGGQTLYPDSVKG (54) | RASKSVSTSGYSFMH (59) | LASNLES (67) |
| F18 | H40 | L40 | AIDHGGGRTYYPDSVKG (51) | RASKSVSTSGYSFMH (59) | LASNLES (67) |
| F19 | H41 | L40 | AIDHGGGRTWYPDSVKG (52) | RASKSVSTSGYSFMH (59) | LASNLES (67) |
| F243 | H39 | L124 | YISSGGGNTYYPDSVKG (46) | RASKSVSTSGYSFMH (59) | VGSRMAF (72) |
| F250 | H39 | L131 | YISSGGGNTYYPDSVKG (46) | RASKSVSTSGYSFMH (59) | VGDRANW (73) |
| F256 | H39 | L137 | YISSGGGNTYYPDSVKG (46) | RASKSVSTSGYSFMH (59) | VGSRLDY (74) |
| F279 | H39 | L160 | YISSGGGNTYYPDSVKG (46) | RASKSVSYVRWSFMH (64) | LASNLES (67) |

TABLE 25-continued

Affinity matured Fabs selected for conversion to IgG

| Fab ID | HC Peptide ID | LC Peptide ID | CDR-H2 (SEQ ID NO:) | CDR-L1 (SEQ ID NO:) | CDR-L2 (SEQ ID NO:) |
|---|---|---|---|---|---|
| F291 | H39 | L172 | YISSGGGNTYYPDSVKG (46) | RASKSVSHIRWSFMH (65) | LASNLES (67) |
| F292 | H39 | L173 | YISSGGGNTYYPDSVKG (46) | RASKSVSHVRWSFMH (61) | LASNLES (67) |
| F295 | H39 | L176 | YISSGGGNTYYPDSVKG (46) | RASKSVSTSGYSFMH (59) | VADRVEV (173) |
| F297 | H190 | L40 | TIDRGGGSTWYPDSVKG (55) | RASKSVSTSGYSFMH (59) | LASNLES (67) |
| F298 | H191 | L40 | AIDGGGGATYYPDSVKG (56) | RASKSVSTSGYSFMH (59) | LASNLES (67) |
| F299 | H192 | L40 | VIDHGGGSTHYPDSVKG (57) | RASKSVSTSGYSFMH (59) | LASNLES (67) |
| F302 | H39 | L179 | YISSGGGNTYYPDSVKG (46) | RASKSVSLIRWSFMH (172) | LASNLES (67) |
| F57 | H79 | L40 | AIDHGGGQTLYPDSVKG (53) | RASKSVSTSGYSFMH (59) | LASNLES (67) |

IgG1/k mAbs were constructed as replicas of the Fabs and as a matrix of heavy and light chain variable regions (Table 26) and tested for affinity and solution properties. The mAb form of the parent Fab is denoted M131. M141 and M408 were selected for further characterization.

TABLE 26 mAbs derived from Fab affinity maturation

| Fab ID | mAb ID | H & L Peptide ID |
|---|---|---|
| Parent | M131 | H39, L40 |
| F18 | M132 | H40, L40 |
| F57 | M133 | H79, L40 |
| F298 | M134 | H191, L40 |
| F299 | M135 | H192, L40 |
| F292 | M136 | H39, L173 |
| F279 | M137 | H39, L160 |
| F256 | M138 | H39, L137 |
| Combination | M139 | C27H40, L173 |
| Combination | M140 | C27H40, L160 |
| Combination | M141 | C27H79, L173 |
| Combination | M142 | C27H79, L160 |
| Combination | M143 | C27H191, L160 |
| Combination | M144 | C27H191, L173 |
| Combination | M145 | C27H192, L173 |
| Combination | M146 | H192, L160 |
| Combination | M408 | H192, L137 |

Example 12: Characterization of Affinity Matured MABS

Selected affinity matured mAbs derived from the parental C2177 and C2191 hybridoma antibodies were codon optimized, introduced into a different vector for dual-expression of heavy and light chains, expressed in CHO-GS cell culture, and purified for further characterization. The IDs of these antibodies in relation to the matured variants described in the Examples above are shown in Table 27.

TABLE 27

| Parent | DNA ID | Single-gene DNA ID | LC Peptide ID | HC Peptide ID |
|---|---|---|---|---|
| 2191 | 429 | 696 | 27L245 | 27H227 |
| 2191 | 492 | 695 | 27L249 | 27H228 |
| 2191 | 488 | 694 | 27L249 | 27H227 |
| 2191 | 141 | 707 | 27H79 | 27L173 |
| 2191 | 408 | 708 | 27H192 | 27L137 |
| 2177 | 703 | 709 | 27H270 | 27L267 |
| 2177 | 706 | 710 | 27H272 | 27L267 |
| 2177 | 671 | 711 | 27H258 | 27L266 |
| 2177 | 668 | 713 | 27H255 | 27L266 |

Summary data for these mAbs is shown below for the $K_D$ analysis by Biacore and the $IC_{50}$ measured in a NF-κβ reporter gene assay (Tables 28 and 29). For this NF-κβ reporter assay, HEK-293F cells were transfected with a total of 36 ng of DNA containing both human CD27 and luciferase constructs, under control of the NF-κβ promoter. HEK-293F transfectants were plated $5\times10^4$ cells per well in 40 µL Freestyle media (Gibco) in 96-well plates. Dilutions of anti-CD27 hybridomas mAbs were added to the assay plate in Freestyle media for a final concentration of 50 µg/mL with 1:3 dilutions and plates were incubated at 37° C. (5% $CO_2$) for one hour. To test for ability of mAbs to neutralize CD70:CD27 signaling, terminally irradiated (4000 rads) HEK-293E CD70 episomal cells were added at 20% of the number of CD27 transfectant cells to the assay plate. To test for agonist activity of hybridoma mAbs, addition of CD70 episomal cells was omitted. Assay plates were incubated overnight at 37° C. (5% $CO_2$) and developed using the Steady-Glo® Luciferase Assay System (Promega) according to the instructions of the manufacturer.

TABLE 28

Characterization of matured variants derived from C2191

| mAb | $k_a$ (1/Ms) | $k_d$ (1/s) | $K_D$ (pM) | NF-κβ Assay IC$_{50}$ (pM) |
|---|---|---|---|---|
| C2191 parent chimera (M41) | 4.35E+05 | 0.0103 | 23678 | 2300 |
| M694 | 4.80E+05 | 7.60E−05 | 105 | 420 |
| M695 | 5.10E+05 | 1.70E−04 | 202 | 250 |
| M696 | 3.70E+05 | 2.1E−05 | 57 | 330 |
| M707 | 5.85E+05 | 1.24E−04 | 213 | 260 |
| M708 | 6.430E+05 | 2.25E−04 | 350 | 260 |

TABLE 29

Characterization of matured variants derived from C2177

| mAb | $k_a$ (1/Ms) | $k_d$ (1/s) | $K_D$ (pM) | NF-κβ Assay IC$_{50}$ (pM) |
|---|---|---|---|---|
| C2177 parent chimera (M40) | 1.06E+06 | 1.32E−03 | 1240 | 466 |
| M709 | 2.30E+06 | 5.89E−05 | 26 | 272 |
| M710 | 2.55E+06 | 4.88E−05 | 19 | 320 |
| M711 | 1.97E+05 | 5.82E−05 | 30 | 258 |
| M713 | 2.06E+05 | 1.16E−05 | 56 | 296 |

CDR and V Region Sequences

TABLE 30

| 2177 path 1 | | | | |
|---|---|---|---|---|
| VH | | CDR-H1 (SEQ ID NO:) | CDR-H2 (SEQ ID NO:) | CDR-H3 (SEQ ID NO:) |
| | | Kabat | Kabat | Kabat |
| H7 | M40 parent | SSWMN (1) | RIYPGDGDTNYNGKFKG (3) | SDYYGDYGFAY (23) |
| | | Extended CDR-H1 | Kabat-7 (+2 HFR residues to show PMT mutations) | Kabat |
| H28 | HFR(M69) | GYAFSSSWMN (2) | RIYPGDGDTNYS (4) | SDYYGDYGFAY (23) |
| H236 | | GYAFSSSWMN (2) | RIYPGDGDTNYS | ADYYGDYGFGY (162) |
| H237 | | GYAFSSSWMN (2) | RIFVRDGDTNYS (5) | SDYYGDYGFAY (23) |
| H238 | | GYAFSSSWMN (2) | RIYVGDGDTNYS (6) | SDYYGDYGFAY (23) |
| H239 | M596, M600 | GYAFSSSWMN (2) | RIYAGDGDTNYS (7) | SDYYGDYGFAY (23) |
| H240 | | GYAFSSSWMN (2) | RIYARDGDTNYS (8) | SDYYGDYGFAY (23) |
| H241 | | GYAFSSSWMN (2) | RIYGRDGDTNYS (9) | SDYYGDYGFAY (23) |
| H242 | | GYAFSSSWMN (2) | RIYANDGDTNYS (10) | SDYYGDYGFAY (23) |
| H243 | | GYAFSSSWMN (2) | RIYGGDGDTNYS (11) | SDYYGDYGFAY (23) |
| H244 | | GYAFSSSWMN (2) | RIYSGDGDTNYS (12) | SDYYGDYGFAY (23) |
| H245 | | GYAFSSSWMN (2) | RIYSRDGDTNYS (13) | SDYYGDYGFAY (23) |
| H259 | M678 | GYAFSSSWMN (2) | RIYAGDGDTAYS (14) | SDYYGDYGFAY (23) |
| H260 | M680 | GYAFSSSWMN (2) | RIYAGDGDTNYA (15) | SDYYGDYGFAY (23) |
| H270 | M703 = M709 | GYAFSSSWMN (2) | RIYAGDADTAYS (16) | SDYYGDYGFAY (23) |
| H272 | M706 = M710 | GYAFSSSWMN (2) | RIYAGDADTNYA (17) | SDYYGDYGFAY (23) |
| | | | $RIX_1X_2X_3DX_4DTX_5YX_6$ (151) | |

For SEQ ID NO: 151, $X_1$ is F or Y; $X_2$ is A, G, S, OR V; $X_3$ is G, N, or R; $X_4$ is A or G; $X_5$ is A or N; and $X_6$ is A or S

TABLE 31

| | | 2177 path 2 | | |
|---|---|---|---|---|
| VH | | CDR-H1 (SEQ ID NO:) Kabat | CDR-H2 (SEQ ID NO:) Kabat | CDR-H3 (SEQ ID NO:) Kabat |
| H7 | M40 parent | SSWMN (1) | RIYPGDGDTNYNGKFKG (3) | SDYYGDYGFAY (23) |
| | | Extended CDR-H1 | Kabat-7 (the rest of CDR is the same in mouse and HFR) | Kabat |
| H24 | HFR(M50) | GYAFSSSWMN (2) | RIYPGDGDTNYNGKFKG (18) | SDYYGDYGFAY (23) |
| H221 | M169, M170, M171 | GYAFSSSWMN (2) | RIYSGDGDTNYNGKFKG (19) | SDYYGDYGFAY (23) |
| H257 | M670 | GYAFSSSWMN (2) | RIYSGDADTNYAQKFKG (20) | SDYYGDYGFAY (23) |
| H258 | M671 = M711 | GYAFSSSWMN (2) | RIYSGDADTNYNQKFKG (21) | SDYYGDYGFAY (23) |
| H25 | HFR (M55); M149-156; M159 | GYAFSSSWMN (2) | RIYPGDGDTNYNGKFKG (18) | SDYYGDYGFAY (23) |
| H196 | M158; M160-167 | GYAFSSSWMN (2) | RIYSGDGDTNYNGKFKG (19) | SDYYGDYGFAY (23) |
| H255 | M668 = M713; M672; | GYAFSSSWMN (2) | RIYSGDADTNYAQKFKG (20) | SDYYGDYGFAY (23) |
| H256 | M669; M673 | GYAFSSSWMN (2) | RIYSGDADTNYNQKFKG (21) | SDYYGDYGFAY (23) |
| H197 | M157 | GYAFSSSWMN (2) | RIYQGDGDTNYNGKFKG (22) | SDYYGDYGFAY (23) |
| | | | RIYX$_1$GDX$_2$DTNYX$_3$X$_4$KFKG (152) | |

For SEQ ID NO: 152, X$_1$ is P, Q, or S; X$_2$ is A or G; X$_3$ is A or N; X$_4$ is G or Q.

TABLE 32

| | | 2177 path 1 | | |
|---|---|---|---|---|
| VL | | CDR-L1 (SEQ ID NO:) Kabat | CDR-L2 (SEQ ID NO:) Kabat | CDR-L3 (SEQ ID NO:) Kabat |
| L18 | M40 parent mouse | KASQSVDYAGDSYMN (24) | AASNLES (37) | QQSNEDPYT (41) |
| L35 | HFR (M69) | KASQSVDYAGDSYMN (24) | AASNLES (37) | QQSNEDPYT (41) |
| L255 | M600; M678; M680 | KASQSVDYAGDSFMN (25) | AASNLES (37) | QQSNEDPYT (41) |
| L256 | | KASQSVDYAGDSWMN (26) | VASNLES (38) | QQSNEDPYT (41) |
| L257 | M596 | KASQSVDYAGDSWMN (26) | TASNLES (39) | QQSNEDPYT (41) |
| L258 | | KASQSVDYAGSSFMN (27) | TASNLES (39) | QQSNEDPYT (41) |

TABLE 32-continued

2177 path 1

| VL | CDR-L1 (SEQ ID NO:) Kabat | CDR-L2 (SEQ ID NO:) Kabat | CDR-L3 (SEQ ID NO:) Kabat |
|---|---|---|---|
| L260 | KASQSVDWAGHSWMN (28) | TASNLES (39) | QQSNEDPYT (41) |
| L261 | KASQSVDYAGSS FMN (27) | EASNLES (40) | QQSNEDPYT (41) |
| L267 M703 = M709; M706 = M710 | KASQSVDYAGESFMN (29) | AASNLES (37) | QQSNEDPYT (41) |
|  | KASQSVDX$_1$AGX$_2$SX$_3$MN (153) | X$_1$ASNLES (154) |  |

For SEQ ID NO: 153, X$_1$ is W or Y; X$_2$ is D, E, S or H; X$_3$ is F, W, or Y.
For SEQ ID NO: 154, X$_1$ is A, E, T, or V;

TABLE 33

2177 path 2

| VL |  | CDR-L1 (SEQ ID NO:) Kabat | CDR-L2 (SEQ ID NO:) Kabat | CDR-L3 (SEQ ID NO:) Kabat |
|---|---|---|---|---|
| L18 | M40 parent mouse | KASQSVDYAGDSYMN (24) | AASNLES (37) | QQSNEDPYT (41) |
| L36 | HFR (M55; M50) | KASQSVDYAGDSYMN (24) | AASNLES (37) | QQSNEDPYT (41) |
| L216 | M156; M167 | KASQSVDYFSESYMN (30) | AASNLES (37) | QQSNEDPYT (41) |
| L217 | M155; M166; M170; M672; M673 | KASQSVDYAHES FMN (31) | AASNLES (37) | QQSNEDPYT (41) |
| L218 | M150; M161 | KASQSVDYFGDSLMN (32) | AASNLES (37) | QQSNEDPYT (41) |
| L219 | M149; M160; M169 | KASQSVDYAGDSFMN (25) | AASNLES (37) | QQSNEDPYT (41) |
| L266 | M668 = M713; M669; M670; M671 = M711; | KASQSVDYAGESFMN (31) | AASNLES (37) | QQSNEDPYT (41) |
| L220 | M157; M171; M158; M159 | KASQSVDYAGDSYMN (24) | AASNLES (37) | QQSNEDPYT (41) |
| L221 | M154 | KASQSVDYFRTSFMN (33) | AASNLES (37) | QQSNEDPYT (41) |
| L222 | M153 | KASQSVDYVGTSFMN (34) | AASNLES (37) | QQSNEDPYT (41) |
| L223 | M152; M163 | KASQSVDYWSDSFMN (35) | AASNLES (37) | QQSNEDPYT (41) |
| L224 | M151; M162 | KASQSVDYYNSSFMN (36) | AASNLES (37) | QQSNEDPYT (41) |
|  |  | KASQSVDYX$_1$X$_2$X$_3$MSX$_4$MN (155) |  |  |

For SEQ ID NO: 155, X$_1$ is A, F, V, W or Y; X$_2$ is G, H, N, R, or S; X$_3$ is D, E, S, or T; X$_4$ is F, L, or Y.

TABLE 34

2191 path 1

| VH | | CDR-H1 (SEQ ID NO:) | CDR-H2 (SEQ ID NO:) | CDR-H3 (SEQ ID NO:) |
|---|---|---|---|---|
| | | Kabat | Kabat | Kabat |
| H10 | M41 parent | SYTMS (42) | YISSGGGNTYYPDSVKG (46) | HRGNPFDY (58) |
| | | Extended CDR-H1 | Kabat | Kabat |
| H31 | HFR (M91) | GFTFSSYTMS (43) | YISSGGGNTYYPDSVKG (46) | HRGNPFDY (58) |
| H227 | M427, M429 = M696; M488 = M694; M489 | GFTFSSYGMS (44) | YIDEGGGQTIYPDSVKG (47) | HRGNPFDY (58) |
| H228 | M492 = M695; M493 | GFTFSSYSMS (45) | YIDAGGGFTIYPDSVKG (48) | HRGNPFDY (58) |
| H231 | M501 | GFTFSSYSMS (45) | HIDAGGGRTWYPDSVKG (49) | HRGNPFDY (58) |
| H222 | M526 | GFTFSSYGMS (44) | YIDRGGGVTIYPDSVKG (50) | HRGNPFDY (58) |
| H227 | Kabat defined CDR-H1 | SYGMS (161) | | |
| | | | X₁IX₂X₃GGGX₄TX₅YPDSVKG (156) | |

For SEQ ID NO: 156, X₁ is H or Y; X₂ is D or S; X₃ is A, E, R, or S; and X₄ is I, W, or Y.

TABLE 35

2191 path 2

| VH | | CDR-H1 (SEQ ID NO:) | CDR-H2 (SEQ ID NO:) | CDR-H3 (SEQ ID NO:) |
|---|---|---|---|---|
| | | Kabat | Kabat | Kabat |
| H10 | M41 parent | SYTMS (42) | YISSGGGNTYYPDSVKG (46) | HRGNPFDY (58) |
| | | Extended CDR-H1 | Kabat | Kabat |
| H39 | HFR; M131; M136-138 | GFTFSSYTMS (43) | YISSGGGNTYYPDSVKG (46) | HRGNPFDY (58) |
| H40 | M132; M139; M140 | GFTFSSYTMS (43) | AIDHGGGRTYYPDSVKG (51) | HRGNPFDY (58) |
| H41 | | GFTFSSYTMS (43) | AIDHGGGRTWYPDSVKG (52) | HRGNPFDY (58) |
| H79 | M133; M141 = M707; M142 | GFTFSSYTMS (43) | AIDHGGGQTLYPDSVKG (53) | HRGNPFDY (58) |
| H145 | | GFTFSSYTMS (43) | YISGGGGQTLYPDSVKG (54) | HRGNPFDY (58) |
| H190 | | GFTFSSYTMS (43) | TIDRGGGSTWYPDSVKG (55) | HRGNPFDY (58) |
| H191 | M134; M143; M144; | GFTFSSYTMS (43) | AIDGGGGATYYPDSVKG (56) | HRGNPFDY (58) |

TABLE 35-continued

2191 path 2

| VH | | CDR-H1 (SEQ ID NO:) | CDR-H2 (SEQ ID NO:) | CDR-H3 (SEQ ID NO:) |
|---|---|---|---|---|
| H192 | M135; M145; M146; M408 = M708 | GFTFSSYTMS (43) | VIDHGGGSTHYPDSVKG (57) | HRGNPFDY (58) |
|  |  |  | X₁IX₂X₃GGGX₄TX₅YPDSVKG (157) |  |

For SEQ ID NO: 157, $X_1$ is A, T, V, or Y; $X_2$ is D or S; $X_3$ is G, H, R, or S; $X_4$ is A, N, Q, R, or S; and $X_5$ is H, L, W, or Y.

TABLE 36

2191 path 1

| VL | | CDR-L1 (SEQ ID NO:) Kabat | CDR-L2 (SEQ ID NO:) Kabat | CDR-L3 (SEQ ID NO:) Kabat |
|---|---|---|---|---|
| L20 | M41 parent mouse | RASKSVSTSGYSFMH (59) | LASNLES (67) | QHSRELPWT (75) |
| L42 | HFR (M91) | RASKSVSTSGYSFMH (59) | LASNLES (67) | QHSRELPWT (75) |
| L244 | M427 | RASKSVSAWGYSFMH (60) | VASRLES (68) | QHSRELPWT (75) |
| L245 | M429 = M696 | RASKSVSHVRWSFMH (61) | LASKLES (69) | QHSRELPWT (75) |
| L249 | M488 = M694; M492 = M695; M526 | RASKSVSEGRWSFMH (62) | VASRLES (68) | QHSRELPWT (75) |
| L250 | M489; M493; M501 | RASKSVSLDRWSFMH (63) RASKSVSX₁X₂X₃X₄SFMH (158) | LASNLES (67) | QHSRELPWT (75) |

For SEQ ID NO: 158, $X_1$ is A, E, H, L, T, or Y; $X_2$ is D, G, I, S, V, or W; $X_3$ is G or R; and $X_4$ is W or Y.

TABLE 37

2191 path 2

| VL | | CDR-L1 (SEQ ID NO:) Kabat | CDR-L2 (SEQ ID NO:) Kabat | CDR-L3 (SEQ ID NO:) Kabat |
|---|---|---|---|---|
| L20 | M41 parent mouse | RASKSVSTSGYSFMH (59) | LASNLES (67) | QHSRELPWT (75) |
| L59 |  | RASKSVSTSGYSFMH (59) | VGNRLED (70) | QHSRELPWT (75) |
| L62 |  | RASKSVSTSGYSFMH (59) | VGDRRQE (71) | QHSRELPWT (75) |
| L124 |  | RASKSVSTSGYSFMH (59) | VGSRMAF (72) | QHSRELPWT (75) |
| L131 |  | RASKSVSTSGYSFMH (59) | VGDRANW (73) | QHSRELPWT (75) |
| L137 | M138; M408 = M708 | RASKSVSTSGYSFMH (59) | VGSRLDY (74) | QHSRELPWT (75) |
| L160 | M137; M160; M142; M143; M146 | RASKSVSYVRWSFMH (64) | LASNLES (67) | QHSRELPWT (75) |
| L172 |  | RASKSVSHIRWSFMH (65) | LASNLES | QHSRELPWT (75) |

TABLE 37-continued 2191 path 2

| VL | CDR-L1 (SEQ ID NO:) Kabat | CDR-L2 (SEQ ID NO:) Kabat | CDR-L3 (SEQ ID NO:) Kabat |
|---|---|---|---|
| L173 | M136; M139; M141 = M707; M144; M145 | RASKSVSHVRWSFMH (66) | LASNLES | QHSRELPWT (75) |

Protein and Antibody Variable Region Sequences

TABLE 38

| SEQ ID NO | Clone | Sequence (CDR sequences underlined) | Features or Origin | Comments |
|---|---|---|---|---|
| 174 | Human CD27 ECD | TPAPKSCPERHYWAQGKLCCQMCEPGTFLVKDCDQHR KAAQCDPCIPGVSFSPDHHTRPHCESCRHCNSGLLVR NCTITANAECACRNGWQCRDKECTECDPLPNPSLTAR SSQALSPHPQPTHLPYVSEMLEARTAGHMQTLADFRQ LPARTLSTHWPPQRSLCSSDFIRILHHHHHH | ECD: 1-173, His6 | |
| 175 | Human CD27 ECD truncated | TPAPKSCPERHYWAQGKLCCQMCEPGTFLVKDCDQHR KAAQCDPCIPGVSFSPDHHTRPHCESCRHCNSGLLVR NCTITANAECACRNGWQCRDKECTECDPLPNPSLTAR SSQALSPHPQLEVLFQGPHHHHHH | ECD: 1-121, cleavage site, His6 | |
| 176 | Human CD27 ECD truncated | TPAPKSCPERHYWAQGKLCCQMCEPGTFLVKDCDQHR KAAQCDPCIPGVSFSPDHHTRPHCESCRHCNSGLLVR NCTITANAECACRNGWQCRDKECTECDGGHHHH | ECD: 1-101 | Proteos |
| 150 | Human CD70 ECD | MPEEGSGCSVRRRPYGCVLRALVPLVAGLVICLVVCI QRFAQAQQQLPLESLGWDVAELQLNHTGPQQDPRLYW QGGPALGRSFLHGPELDKGQLRIHRDGIYMVHIQVTL AICSSTTASRHHPTTLAVGICSPASRSISLLRLSFHQ GCTIASQRLTPLARGDTLCTNLTGTLLPSRNTDETFF GVQWVRP | ECD | |
| 76 | C2186 Heavy Chain (HC) Variable Region | QVQLQQPGAELVKPGASVKLSCKASGYTFT<u>NYWMN</u>WV KQRPGRGLEWIG<u>RIHPSDSETHYNQNFKS</u>KATLTVDK SSSTAYIQLSSLTSEDSAVYYCAR<u>PVLYGDYGFPC</u>WG QGTLVTVSA | | Murine |
| 77 | C2186 Light Chain (LC) Variable Region | DIVLTQSPASLAVSLGQRATISC<u>KASQSVDYDGDSYM NW</u>YQQKPGQPPKLLIY<u>AASNLES</u>GIPARFSGSGSGTD FTLNIHPVEEEDAATYYC<u>QQSNEDPYT</u>FGGGTKLEIK | | Murine |
| 78 | C2192 Heavy Chain (HC) Variable Region | QVQLQQSGPELVKPGASVKISCKASGYAFS<u>SSWMN</u>WV KQRPGKGLEWIG<u>RIYPGDGDTNYNGKFKG</u>KATLTADK SSSTAYMQLSSLTSEDSAVYFCAR<u>RWDGGNYFFDY</u>WG QGTTLTVSS | | Murine |
| 79 | C2192 Light Chain (LC) Variable Region | DIVMTQSHKFMSTSVGDRVSITC<u>MASQDVGTAVA</u>WYQ RRPGQSPKLLIY<u>WTSTRHT</u>GVPDRFTGSGSGTDFTLT ISNVQSEDLADYFC<u>QQYSSYPLT</u>FGSGTKLEIK | | Murine |
| 80 | C2177 Heavy Chain (HC) Variable Region | QVQLQQSGPELVKPGASVKISCKASGYAFS<u>SSWMN</u>WV KQRPGKGLEWIG<u>RIYPGDGDTNYNGKFKG</u>KATLTADK SSSTAYMQLSSLTSEDSAVYFCAR<u>SDYYGDYGFAY</u>WG QGTLVTVSA | H7 | Murine |

TABLE 38-continued

| SEQ ID NO | Clone | Sequence (CDR sequences underlined) | Features or Origin | Comments |
|---|---|---|---|---|
| 81 | C2177 Light Chain (LC) Variable Region | DIVLTQSPASLAVSLGQRATISC<u>KASQSVDYAGDSYM NW</u>YQQKPGQPPKLLIY<u>AASNLES</u>GIPARFSGSGSGTD FTLNIHPVEEEDAATYYC<u>QQSNEDPYT</u>FGGGTKLEIK | L18 | Murine |
| 82 | L35 | DIVMTQSPDSLAVSLGERATINC<u>KASQSVDYAGDSYM NW</u>YQQKPGQPPKLLIY<u>AASNLES</u>GVPDRFSGSGSGTD FTLTISSLQAEDVAVYYC<u>QQSNEDPYT</u>FGQGTKLEIK | 4-1/2 | HFR selected for C2177 AM path 1 |
| 83 | L255 | DIVMTQSPDSLAVSLGERATINC<u>KASQSVDYAGDSFM NW</u>YQQKPGQPPKLLIY<u>AASNLES</u>GVPDRFSGSGSGTD FTLTISSLQAEDVAVYYC<u>QQSNEDPYT</u>FGQGTKLEIK |  | VL in M584, M600 AM clones; in M678, M680 PTM variants |
| 84 | L256 | DIVMTQSPDSLAVSLGERATINC<u>KASQSVDYAGDSWM NW</u>YQQKPGQPPKLLIY<u>VASNLES</u>GVPDRFSGSGSGTD FTLTISSLQAEDVAVYYC<u>QQSNEDPYT</u>FGQGTKLEIK |  | C2177 affinity maturation path 1 |
| 85 | L257 | DIVMTQSPDSLAVSLGERATINC<u>KASQSVDYAGDSWM NW</u>YQQKPGQPPKLLIY<u>TASNLES</u>GVPDRFSGSGSGTD FTLTISSLLAEDVAVYYC<u>QQSNEDPYT</u>FGQGTKLEIK |  | VL in M558, M596 AM clones |
| 86 | L258 | DIVMTQSPDSLAVSLGERATINC<u>KASQSVDYAGSSFM NW</u>YQQKPGQPPKLLIY<u>TASNLES</u>GVPDRFSGSGSGTD FTLTISSLQAEDVAVYYC<u>QQSNEDPYT</u>FGQGTKLEIK |  | C2177 affinity maturation path 1 |
| 87 | L260 | DIVMTQSPDSLAVSLGERATINC<u>KASQSVDWAGHSWM NW</u>YQQKPGQPPKLLIY<u>TASNLES</u>GVPDRFSGSGSGTD FTLTISSLQAEDVAVYYC<u>QQSNEDPYT</u>FGQGTKLEIK |  | C2177 affinity maturation path 1 |
| 88 | L261 | DIVMTQSPDSLAVSLGERATINC<u>KASQSVDYAGSSFM NW</u>YQQKPGQPPKLLIY<u>EASNLES</u>GVPDRFSGSGSGTD FTLTISSLQAEDVAVYYC<u>QQSNEDPYT</u>FGQGTKLEIK |  | C2177 affinity maturation path 1 |
| 89 | L267 | DIVMTQSPDSLAVSLGERATINC<u>KASQSVDYAGESFM NW</u>YQQKPGQPPKLLIY<u>AASNLES</u>GVPDRFSGSGSGTD FTLTISSLQAEDVAVYYC<u>QQSNEDPYT</u>FGQGTKLEIK |  | VL in M703, M706 PTM variants |
| 90 | L36 | DIQMTQSPSSLSASVGDRVTITC<u>KASQSVDYAGDSYM NW</u>YQQKPGKAPKLLIY<u>AASNLES</u>GVPSRFSGSGSGTD FTLTISSLQPEDFATYYC<u>QQSNEDPYT</u>FGQGTKLEIK | O12/2 | HFR selected for C2177 AM path 2 |
| 91 | L216 | DIQMTQSPSSLSASVGDRVTITC<u>KASQSVDYFSESYM NW</u>YQQKPGKAPKLLIY<u>AASNLES</u>GVPSRFSGSGSGTD FTLTISSLQPEDFATYYC<u>QQSNEDPYT</u>FGQGTKVEIK |  | C2177 AM path 2 |
| 92 | L217 | DIQMTQSPSSLSASVGDRVTITC<u>KASQSVDYAHESFM NW</u>YQQKPGKAPKLLIY<u>AASNLES</u>GVPSRFSGSGSGTD FTLTISSLQPEDFATYYC<u>QQSNEDPYT</u>FGQGTKVEIK |  | VL in M166 AM clone |
| 93 | L218 | DIQMTQSPSSLSASVGDRVTITC<u>KASQSVDYFGDSLM NW</u>YQQKPGKAPKLLIY<u>AASNLES</u>GVPSRFSGSGSGTD FTLTISSLQPEDFATYYC<u>QQSNEDPYT</u>FGQGTKVEIK |  | C2177 AM path 2 |
| 94 | L219 | DIQMTQSPSSLSASVGDRVTITC<u>KASQSVDYAGDSFM NW</u>YQQKPGKAPKLLIY<u>AASNLES</u>GVPSRFSGSGSGTD FTLTISSLQPEDFATYYC<u>QQSNEDPYT</u>FGQGTKVEIK |  | VL in M160, M169 AM clones |

TABLE 38-continued

| SEQ ID NO | Clone | Sequence (CDR sequences underlined) | Features or Origin | Comments |
|---|---|---|---|---|
| 95 | L219 PTM | DIQMTQSPSSLSASVGDRVTITC<u>KASQSVDYAGESFM</u><br><u>N</u>WYQQKPGKAPKLLIY<u>AASNLES</u>GVPSRFSGSGSGTD<br>FTLTISSLQPEDFATYYC<u>QQSNEDPYT</u>FGQGTKVEIK | | VL in M668, M669, M670, M671 PTM variants |
| 96 | L266 | DIQMTQSPSSLSASVGDRVTITC<u>KASQSVDYAGeSFM</u><br><u>N</u>WYQQKPGKAPKLLIY<u>AASNLES</u>GVPSRFSGSGSGTD<br>FTLTISSLQPEDFATYYC<u>QQSNEDPYT</u>FGQGTKVEIK | | VL in M668, M669, M670, M671 PTM variants |
| 97 | L220 | DIQMTQSPSSLSASVGDRVTITC<u>KASQSVDYAGDSYM</u><br><u>N</u>WYQQKPGKAPKLLIY<u>AASNLES</u>GVPSRFSGSGSGTD<br>FTLTISSLQPEDFATYYC<u>QQSNEDPYT</u>FGQGTKVEIK | | VL in M158 AM clone |
| 98 | L221 | DIQMTQSPSSLSASVGDRVTITC<u>KASQSVDYFRTSFM</u><br><u>N</u>WYQQKPGKAPKLLIY<u>AASNLES</u>GVPSRFSGSGSGTD<br>FTLTISSLQPEDFATYYC<u>QQSNEDPYT</u>FGQGTKVEIK | | C2177 AM path 2 |
| 99 | L222 | DIQMTQSPSSLSASVGDRVTITC<u>KASQSVDYVGTSFM</u><br><u>N</u>WYQQKPGKAPKLLIY<u>AASNLES</u>GVPSRFSGSGSGTD<br>FTLTISSLQPEDFATYYC<u>QQSNEDPYT</u>FGQGTKVEIK | | C2177 AM path 2 |
| 100 | L223 | DIQMTQSPSSLSASVGDRVTITC<u>KASQSVDYWSDSFM</u><br><u>N</u>WYQQKPGKAPKLLIY<u>AASNLES</u>GVPSRFSGSGSGTD<br>FTLTISSLQPEDFATYYC<u>QQSNEDPYT</u>FGQGTKVEIK | | C2177 AM path 2 |
| 101 | L224 | DIQMTQSPSSLSASVGDRVAITC<u>KASQSVDYYNSSFM</u><br><u>N</u>WYQQKPGKAPKLLIY<u>AASNLES</u>GVPSRFSGSGSGTD<br>FTLTISSLQPEDFATYYC<u>QQSNEDPYT</u>FGQGTKVEIK | | C2177 AM path 2 |
| 102 | H24 | EVQLVQSGAEVKKPGESLKISCKGS<u>GYAFSSSWMN</u>WV<br>RQMPGKGLEWMG<u>RIYPGDGDTNYNGKFKG</u>QVTISADK<br>SISTAYLQWSSLKASDTAMYYCAR<u>SDYYGDYGFAY</u>WG<br>QGTLVTVSS | IGHV5-51/4 | HFR selected C2177 AM path 2 |
| 103 | H221 | EVQLVQSGAEVKKPGESLKISCKGS<u>GYAFSSSWMN</u>WV<br>RQMPGKGLEWMG<u>RIYSGDGDTNYNGKFKG</u>QVTISADK<br>SISTAYLQWSSLKASDTAMYYCAR<u>SDYYGDYGFAY</u>WG<br>QGTLVTVSS | | VH in M169 AM clones |
| 104 | H257 | EVQLVQSGAEVKKPGESLKISCKGS<u>GYAFSSSWMN</u>WV<br>RQMPGKGLEWMG<u>RIYSGDaDTNYaqKFKG</u>QVTISADK<br>SISTAYLQWSSLKASDTAMYYCAR<u>SDYYGDYGFAY</u>WG<br>QGTLVTVSS | | VH in M670 PTM variant |
| 105 | H258 | EVQLVQSGAEVKKPGESLKISCKGS<u>GYAFSSSWMN</u>WV<br>RQMPGKGLEWMG<u>RIYSGDaDTNYNqKFKG</u>QVTISADK<br>SISTAYLQWSSLKASDTAMYYCAR<u>SDYYGDYGFAY</u>WG<br>QGTLVTVSS | | VH in M671 PTM variant |
| 106 | H25 | QVQLVQSGAEVKKPGASVKVSCKAS<u>GYAFSSSWMN</u>WV<br>RQAPGQGLEWMG<u>RIYPGDGDTNYNGKFKG</u>RVTMTRDT<br>STSTVYMELSSLRSEDTAVYYCAR<u>SDYYGDYGFAY</u>WG<br>QGTLVTVSS | IGHV1-46/4 | HFR selected for C2177 AM, path 2 |
| 107 | H196 | QVQLVQSGAEVKKPGASVKVSCKAS<u>GYAFSSSWMN</u>WV<br>RQAPGQGLEWMG<u>RIYSGDGDTNYNGKFKG</u>RVTMTRDT<br>STSTVYMELSSLRSEDTAVYYCAR<u>SDYYGDYGFAY</u>WG<br>QGTLVTVSS | | VH in M158, M160 AM clones |
| 108 | H255 | QVQLVQSGAEVKKPGASVKVSC<u>KASGYAFSSSWMN</u>WV<br>RQAPGQGLEWMGRIYSG<u>DADTNYAQKFKG</u>RVTMTRDT<br>STSTVYMELSSLRSEDTAVYYCAR<u>SDYYGDYGFAY</u>WG<br>QGTLVTVSS | | VH in M668, M672 PTM variants |
| 109 | H256 | QVQLVQSGAEVKKPGASVKVSC<u>KASGYAFSSSWMN</u>WV<br>RQAPGQGLEWMG<u>RIYSGDADTNYNQKFKG</u>RVTMTRDT<br>STSTVYMELSSLRSEDTAVYYCAR<u>SDYYGDYGFAY</u>WG<br>QGTLVTVSS | | VH in M669, M673 PTM variants |

TABLE 38-continued

| SEQ ID NO | Clone | Sequence (CDR sequences underlined) | Features or Origin | Comments |
|---|---|---|---|---|
| 110 | H197 | QVQLVQSGAEVKKPGASVKVSCKASGYAFSSSWMNWV RQAPGQGLEWMGRIYQGDGDTNYNGKFKGRVTMTRDT STSTVYMELSSLRSEDTAVYYCARSDYYGDYGFAYWG QGTLVTVSS | | C2177 AM clone |
| 111 | H28 | EVQLVQSGAEVKKPGESLKISCKGS<u>GYAFSSSWMN</u>WV RQMPGKGLEWMG<u>RIYPGDGDTN</u>YSPSFQGQVTISADK SISTAYLQWSSLKASDTAMYYCAR<u>SDYYGDYGFAY</u>WG QGTLVTVSS | IGHV5-51c/4 | HFR selected for C2177 affinity maturation (AM) path 1 |
| 112 | H236 | EVQLVQSGAEVKKPGESLKISCKGS<u>GYAFSSSWMN</u>WV RQMPGKGLEWMG<u>RIYPGDGDTN</u>YSPSFQGQVTISADK SISTAYLQWSSLKASDTAMYYCAR<u>ADYYGDYGFGY</u>WG QGTLVTVSS | | VH in M584 AM clone path 1 |
| 113 | H237 | EVQLVQSGAEVKKPGESLKISCKGS<u>GYAFSSSWMN</u>WV RQMPGKGLEWMG<u>RIFVRDGDTN</u>YSPSFQGQVTISADK SISTAYLQWSSLKASDTAMYYCAR<u>SDYYGDYGFAY</u>WG QGTLVTVSS | | C2177 AM clone path 1 |
| 114 | H238 | EVQLVQSGAEVKKPGESLKISCKGS<u>GYAFSSSWMN</u>WV RQMPGKGLEWMG<u>RIYVGDGDTN</u>YSPSFQGQVTISADK SISTAYLQWSSLKASDTAMYYCAR<u>SDYYGDYGFAY</u>WG QGTLVTVSS | | C2177 AM clone path 1 |
| 115 | H239 | EVQLVQSGAEVKKPGESLKISCKGS<u>GYAFSSSWMN</u>WV RQMPGKGLEWMG<u>RIYAGDGDTN</u>YSPSFQGQVTISADK SISTAYLQWSSLKASDTAMYYCAR<u>SDYYGDYGFAY</u>WG QGTLVTVSS | | VH in M596 AM clone path 1 |
| 116 | H240 | EVQLVQSGAEVKKPGESLKISCKGS<u>GYAFSSSWMN</u>WV RQMPGKGLEWMG<u>RIYARDGDTN</u>YSPSFQGQVTISADK SISTAYLQWSSLKASDTAMYYCAR<u>SDYYGDYGFAY</u>WG QGTLVTVSS | | VH in M558, M600 AM clones, path 1 |
| 117 | H241 | EVQLVQSGAEVKKPGESLKISCKGS<u>GYAFSSSWMN</u>WV RQMPGKGLEWMG<u>RIYGRDGDTN</u>YSPSFQGQVTISADK SISTAYLQWSSLKASDTAMYYCAR<u>SDYYGDYGFAY</u>WG QGTLVTVSS | | C2177 AM clone path 1 |
| 118 | H242 | EVQLVQSGAEVKKPGESLKISCKGS<u>GYAFSSSWMN</u>WV RQMPGKGLEWMG<u>RIYANDGDTN</u>YSPSFQGQVTISADK SISTAYLQWSSLKASDTAMYYCAR<u>SDYYGDYGFAY</u>WG QGTLVTVSS | | C2177 AM clone path 1 |
| 119 | H243 | EVQLVQSGAEVKKPGESLKISCKGS<u>GYAFSSSWMN</u>WV RQMPGKGLEWMG<u>RIYGGDGDTN</u>YSPSFQGQVTISADK SISTAYLQWSSLKASDTAMYYCAR<u>SDYYGDYGFAY</u>WG QGTLVTVSS | | C2177 AM clone path 1 |
| 120 | H244 | EVQLVQSGAEVKKPGESLKISCKGS<u>GYAFSSSWMN</u>WV RQMPGKGLEWMG<u>RIYSGDGDTN</u>YSPSFQGQVTISADK SISTAYLQWSSLKASDTAMYYCAR<u>SDYYGDYGFAY</u>WG QGTLVTVSS | | V2177 AM clone path 1 |
| 121 | H245 | EVQLVQSVAEVKKPGESLKISCKGS<u>GYAFSSSWMN</u>WV RQMPGKGLEWMG<u>RIYSRDGDTN</u>YSPSFQGQVTISADK SISTAYLQWSSLKASDTAMYYCAR<u>SDYYGDYGFAY</u>WG QGTLVTVSS | | C2177 AM clone path 1 |
| 122 | H259 | EVQLVQSGAEVKKPGESLKISCKGS<u>GYAFSSSWMN</u>WV RQMPGKGLEWMG<u>RIYAGDGDTA</u>YSPSFQGQVTISADK SISTAYLQWSSLKASDTAMYYCAR<u>SDYYGDYGFAY</u>WG QGTLVTVSS | | VH in M678 PTM mutant |
| 123 | H260 | EVQLVQSGAEVKKPGESLKISCKGS<u>GYAFSSSWMN</u>WV RQMPGKGLEWMG<u>RIYAGDGDTN</u>YAPSFQGQVTISADK SISTAYLQWSSLKASDTAMYYCAR<u>SDYYGDYGFAY</u>WG QGTLVTVSS | | VH in M680 PTM mutant |

TABLE 38-continued

| SEQ ID NO | Clone | Sequence (CDR sequences underlined) | Features or Origin | Comments |
|---|---|---|---|---|
| 124 | H270 | EVQLVQSGAEVKKPGESLKISCKGS<u>GYAFSSSWMN</u>WV RQMPGKGLEWMG<u>RIYAGDADTA</u>YSPSFQGQVTISADK SISTAYLQWSSLKASDTAMYYCAR<u>SDYYGDYGFAY</u>WG QGTLVTVSS | | VH in M703 PTM mutant |
| 125 | H272 | EVQLVQSGAEVKKPGESLKISCKGS<u>GYAFSSSWMN</u>WV RQMPGKGLEWMG<u>RIYAGDADTN</u>YAPSFQGQVTISADK SISTAYLQWSSLKASDTAMYYCAR<u>SDYYGDYGFAY</u>WG QGTLVTVSS | | VH in M706 PTM mutant |

TABLE 39

| SEQ ID | Clone | Sequence | Features or Origin | Comments |
|---|---|---|---|---|
| 126 | C2191 Heavy Chain (HC) Variable Region | EVKLVESGGGLVKPGGSLKLSCAASGFTF<u>SSYTMS</u>WVRQ TPEKRLEWVA<u>YISSGGGNTYYPDSVKG</u>RFTISRDNARNT LYLQMSSLRSEDTAMYYCS<u>RHRGNPFDY</u>WGQGTTLTVSS | H10 | Murine |
| 127 | C2191 Light Chain (LC) Variable Region | DIVLTQSPASLAVSLGQRATISC<u>RASKSVSTSGYSFMH</u>W YQQKPGQPPKLLIY<u>LASNLES</u>GVPARFSGSGSGTDFTLN IHPVEEEDAATYYC<u>QHSRELPWT</u>FGGGTKLEIK | L20 | Murine |
| 128 | H30 | EVQLLESGGGLVQPGGSLRLSCAASG<u>FTFSSYTMS</u>WVRQ APGKGLEWVS<u>YISSGGGNTYYPDSVKG</u>RFTISRDNSKNT LYLQMNSLRAEDTAVYYCAK<u>HRGNPFDY</u>WGQGTLVTVSS | IGHV3-23/4 | HFR selected for C2191 AM path 2 |
| 129 | H79 | EVQLLESGGGLVQPGGSLRLSCAASGFTFSSYTMSWVRQ APGKGLEWVSAIDHGGGQTLYPDSVKGRFTISRDNSKNT LYLQMNSLRAEDTAVYYCARHRGNPFDYWGQGTLVTVSS | | VH in M141 AM variant, path 2. Table 29 |
| 130 | H192 | EVQLLESGGGLVQPGGSLRLSCAASGFTFSSYTMSWVRQ APGKGLEWVSVIDHGGGSTHYPDSVKGRFTISRDNSKNT LYLQMNSLRAEDTAVYYCARHRGNPFDYWGQGTLVTVSS | | VH in M408 AM variant, path 2. Table 29 |
| 131 | H31 | QVQLVESGGGLVKPGGSLRLSCAASG<u>FTFSSYTMS</u>WIRQ APGKGLEWVS<u>YISSGGGNTYYPDSVKG</u>RFTISRDNAKNS LYLQMNSLRAEDTAVYYCAR<u>HRGNPFDY</u>WGQGTLVTVSS | IGHV3-11/4 | HFR selected for C2191 AM path 1 |
| 132 | H222 | QVQLVESGGGLVKPGGSLRLSCAASGFTFSSYGMSWIRQ APGKGLEWVSYIDRGGGVTIYPDSVKGRFTISRDNAKNS LYLQMNSLRAEDTAVYYCARHRGNPFDYWGQGTLVTVSS | | VH in M526 AM variant, path 1 |
| 133 | H227 | QVQLVESGGGLVKPGGSLRLSCAASGFTFSSYGMSWIRQ APGKGLEWVSYIDEGGGQTIYPDSVKGRFTISRDNAKNS LYLQMNSLRAEDTAVYYCARHRGNPFDYWGQGTLVTVSS | | VH in M427, M429, M488, M489 AM variants, path 1 |

TABLE 39-continued

| SEQ ID Clone | Sequence | Features or Origin | Comments |
|---|---|---|---|
| 134 H228 | QVQLVESGGGLVKPGGSLRLSCAASGFTFSSYSMSWIRQ APGKGLEWVSYIDAGGGFTIYPDSVKGRFTISRDNAKNS LYLQMNSLRAEDTAVYYCARHRGNPFDYWGQGTLVTVSS | | VH in M492, M493 AM variants, path 1 |
| 135 H231 | QVQLVESGGGLVKPGGSLRLSCAASGFTFSSYSMSWIRQ APGKGLEWVSHIDAGGGRTWYPDSVKGRFTISRDNAKNS LYLQMNSLRAEDTAVYYCARHRGNPFDYWGQGTLVTVSS | | VH in M501 AM variant, path 1 |
| 136 H232 | QVQLVESGGGLVKPGGSLRLSCAASGFTFSSYPMSWIRQ APGKGLEWVSHIATGGGNTYYPDSVKGRFTISRDNAKNS LYLQMNSLRAEDTAVYYCARHRGNPFDYWGQGTLVTVSS | | C2191 AM clone, path 1 |
| 137 L40 | DIQMTQSPSSLSASVGDRVTITCRASKSVSTSGYSFMHW YQQKPGKAPKLLIYLASNLESGVPSRFSGSGSGTDFTLT ISSLQPEDFATYYCQHSRELPWTFGQGTKVEIK | IGKV012/1 | HFR selected for C2191 AM, path 2 |
| 138 L137 | DIQMTQSPSSLSASVGDRVTITCRASKSVSTSGYSFMHW YQQKPGKAPKLLIYVGSRLDYGVPSRFSGSGSGTDFTLT ISSLQPEDFATYYCQHSRELPWTFGQGTKVEIK | | VL in M408 AM variant, path 2. Table 29 |
| 139 L173 | DIQMTQSPSSLSASVGDRVTITCRASKSVSHVRWSFMHW YQQKPGKAPKLLIYLASNLESGVPSRFSGSGSGTDFTLT ISSLQPEDFATYYCQHSRELPWTFGQGTKVEIK | | VL in M141 AM variant, path 2. Table 29 |
| 140 L42 | DIQMTQSPSSLSASVGDRVTITCRASKSVSTSGYSFMHW YQQKPGKAPKLLIYLASNLESGVPSRFSGSGSGTDFTFT ISSLQPEDIATYYCQHSRELPWTFGQGTKVEIK | IGKV08/1 | HFR selected for C2191 AM path 1 |
| 141 L244 | DIQMTQSPSSLSASVGDRVTITCRASKSVSAWGYSFMHW YQQKPGKAPKLLIYVASRLESGVPSRFSGSGSGTDFTFT ISSLQPEDIATYYCQHSRELPWTFGQGTKVEIK | | VL in M427 AM variant, path 1 |
| 142 L245 | DIQMTQSPSSLSASVGDRVTITCRASKSVSHVRWSFMHW YQQKPGKAPKLLIYLASKLESGVPSRFSGSGSGTDFTFT ISSLQPEDIATYYCQHSRELPWTFGQGTKVEIK | | VL in M429 AM variant, path 1 |
| 143 L249 | DIQMTQSPSSLSASVGDRVTITCRASKSVSEGRWSFMHW YQQKPGKAPKLLIYVASRLESGVPSRFSGSGSGTDFTFT ISSLQPEDIATYYCQHSRELPWTFGQGTKVEIK | | VL in M488, M492, M526 AM variants, path 1 |
| 144 L250 | DIQMTQSPSSLSASVGDRVTITCRASKSVSLDRWSFMHW YQQKPGKAPKLLIYLASNLESGVPSRFSGSGSGTDFTFT ISSLQPEDIATYYCQHSRELPWTFGQGTKVEIK | | VL in M489, M493, M501 AM variants, path 1 |

TABLE 39-continued

| SEQ ID | Clone | Sequence | Features or Origin | Comments |
|---|---|---|---|---|
| 145 | H39 | EVQLLESGGGLVQPGGSLRLSCAASGFTFSSYTMSWVRQ APGKGLEWVSYISSGGGNTYYPDSVKGRFTISRDNSKNT LYLQMNSLRAEDTAVYYCARHRGNPFDYWGQGTLVTVSS | | HFR; VH in M131; M136-138 AM clones, path 2 |
| 146 | H40 | EVQLLESGGGLVQPGGSLRLSCAASGFTFSSYTMSWVRQ APGKGLEWVSAIDHGGGRTYYPDSVKGRFTISRDNSKNT LYLQMNSLRAEDTAVYYCARHRGNPFDYWGQGTLVTVSS | | VH in M132; M139; M140 AM clones, path 2 |
| 147 | H191 | EVQLLESGGGLVQPGGSLRLSCAASGFTFSSYTMSWVRQ APGKGLEWVSAIDGGGGATYYPDSVKGRFTISRDNSKNT LYLQMNSLRAEDTAVYYCARHRGNPFDYWGQGTLVTVSS | | VH in M134; M143; M144; AM clones, path 2 |
| 148 | L160 | DIQMTQSPSSLSASVGDRVTITCRASKSVSYVRWSFMHW YQQKPGKAPKLLIYLASNLESGVPSRFSGSGSGTDFTLT ISSLQPEDFATYYCQHSRELPWTFGQGTKVEIK | | VL in M137; M160; M142; M143; M146 clones, path 2 |

TABLE 40

CD27 and CD70 Proteins

| SEQ ID NO: | DESCRIPTION | Features, Abbreviations |
|---|---|---|
| 149 | Human CD27 propolypeptide | 1-20 Signal, 21-191 Extracellular domain, 192-212 Transmembrane, 213-260 Intracellular TPAPKSCPER HYWAQGKLCC QMCEPGTFLV KDCDQHRKAA QCDPCIPGVS FSPDHHTRPH CESCRHCNSG LLVRNCTITA NAECACRNGW QCRDKECTEC DPLPNPSLTA RSSQALSPHP QPTHLPYVSE MLEARTAGHM QTLADFRQLP ARTLSTHWPP QRSLCSSDFI RILVIFSGMF LVFTLAGALF LHQRRKYRSN KGESPVEPAE PCRYSCPREE EGSTIPIQED YRKPEPACSP |
| 150 | Human CD70 propolypeptide | 1-17 intracellular, 18-38 transmembrane, and 39-193 extracellular MPEEGSGCSV RRRPYGCVLR AALVPLVAGL VICLVVCIQR FAQAQQQLPL ESLGWDVAEL QLNHTGPQQD PRLYWQGGPA LGRSFLHGPE LDKGQLRIHR DGIYMVHIQV TLAICSSTTA SRHHPTTLAV GICSPASRSI SLLRLSFHQG CTIASQRLTP LARGDTLCTN LTGTLLPSRN TDETFFGVQW VRP |

TABLE 41

Antibody constant region sequences

| Description | Sequence | SEQ ID NO: |
|---|---|---|
| Heavy chain human IgG4 Ala/Ala Ser to Pro constant region | astkgpsvfplapcsrstsestaalgclvkdyfpepvtvswn sgaltsgvhtfpavlqssglyslssvvtvpssslgtktytcn vdhkpsntkvdkrveskygppcppcpapeaaggpsvflfppk pkdtlmisrtpevtcvvvdvsqedpevqfnwyvdgvevhnak tkpreeqfnstyrvvsvltvlhqdwingkeykckvsnkglps siektiskakgqprepqvytlppsqeemtknqvsltclvkgf ypsdiavewesngqpennykttppvldsdgsfflysrltvdk srwqegnvfscsvmhealhnhytqkslslslgk | 159 |

TABLE 41-continued

Antibody constant region sequences

| Description | Sequence | SEQ ID NO: |
|---|---|---|
| Light chain human kappa constant region | rtvaapsvfifppsdeqlksgtasvvcllnnfypreakvqwk vdnalqsgnsqesvteqdskdstyslsstltlskadyekhkv yacevthqglsspvtksfnrgec | 160 |

TABLE 42

Antibody nucleotide sequences

| Description | Sequence | SEQ ID NO: |
|---|---|---|
| Light Chain encoding sequence (encodes the light chain sequence of SEQ ID NO: 160) | GACATCCAGATGACCCAGAGCCCCAGCAGCCTGAGCGCCAGCGTGGGCGACCGGG TGACCATCACCTGCCGGGCCAGCAAGAGCGTGAGCGAGGGGCGATGGAGCTTCAT GCACTGGTACCAGCAGAAGCCCGGCAAGGCCCCCAAGCTGCTGATCTACGTGGCC AGCAGACTGGAGAGCGGCGTGCCCAGCCGGTTCAGCGGCAGCGGCAGCGGCACCG ACTTCACCTTCACCATCAGCAGCCTGCAGCCCGAGGACATCGCCACCTACTACTG CCAGCACAGCCGGGAGCTGCCCTGGACCTTCGGCCAGGGCACCAAGGTGGAGATC AAGCGTACGGTGGCTGCACCATCTGTCTTCATCTTCCCGCCATCTGATGAGCAGT TGAAATCTGGAACTGCCTCTGTTGTGTGCCTGCTGAATAACTTCTATCCCAGAGA GGCCAAAGTACAGTGGAAGGTGGATAACGCCCTCCAATCGGGTAACTCCCAGGAG AGTGTCACAGAGCAGGACAGCAAGGACAGCACCTACAGCCTCAGCAGCACCCTGA CGCTGAGCAAAGCAGACTACGAGAAACACAAAGTCTACGCCTGCGAAGTCACCCA TCAGGGCCTGAGCTCGCCCGTCACAAAGAGCTTCAACAGGGGAGAGTGT | 163 |
| Heavy Chain encoding sequence (encodes the heavy chain sequence of SEQ ID NO: 159) | CAGGTGCAGCTGGTGGAGAGCGGCGGCGGCCTGGTGAAGCCCGGCGGCAGCCTGC GGCTGAGCTGCGCCGCCAGCGGCTTCACCTTCAGCAGCTACGGGATGAGCTGGAT CCGGCAGGCCCCCGGCAAGGGCCTGGAGTGGGTGAGCTACATCGATGAGGGCGGC GGCCAGACCATCTACCCCGACAGCGTGAAGGGCCGGTTCACCATCAGCCGGGACA ACGCCAAGAACAGCCTGTACCTGCAGATGAACAGCCTGCGGGCCGAGGACACCGC CGTGTACTACTGCGCCCGGCACCGGGGCAACCCCTTCGACTACTGGGGCCAGGGC ACCCTGGTGACCGTGAGCAGCGCTTCCACCAAGGGCCCATCCGTCTTCCCCCTGG CGCCCTGCTCCAGGAGCACCTCCGAGAGCACAGCCGCCCTGGGCTGCCTGGTCAA GGACTACTTCCCCGAACCGGTGACGGTGTCGTGGAACTCAGGCGCCCTGACCAGC GGCGTGCACACCTTCCCGGCTGTCCTACAGTCCTCAGGACTCTACTCCCTCAGCA GCGTGGTGACCGTGCCCTCCAGCAGCTTGGGCACGAAAACCTACACCTGCAACGT AGATCACAAGCCCAGCAACACCAAGGTGGACAAGAGAGTTGAGTCCAAATATGGT CCCCCATGCCCACCATGCCCAGCACCTGAGGCCGCCGGGGGACCATCAGTCTTCC TGTTCCCCCCAAAACCCAAGGACACTCTCATGATCTCCCGGACCCCTGAGGTCAC GTGCGTGGTGGTGGACGTGAGCCAGGAAGACCCCGAGGTCCAGTTCAACTGGTAC GTGGATGGCGTGGAGGTGCATAATGCCAAGACAAAGCCGCGGGAGGAGCAGTTCA ACAGCACGTACCGTGTGGTCAGCGTCCTCACCGTCCTGCACCAGGACTGGCTGAA CGGCAAGGAGTACAAGTGCAAGGTCTCCAACAAAGGCCTCCCGTCCTCCATCGAG AAAACCATCTCCAAAGCCAAAGGGCAGCCCCGAGAGCCACAGGTGTACACCCTGC CCCCATCCCAGGAGGAGATGACCAAGAACCAGGTCAGCCTGACCTGCCTGGTCAA AGGCTTCTACCCCAGCGACATCGCCGTGGAGTGGGAGAGCAATGGGCAGCCGGAG AACAACTACAAGACCACGCCTCCCGTGCTGGACTCCGACGGCTCCTTCTTCCTCT ACAGCAGGCTAACCGTGGACAAGAGCAGGTGGCAGGAGGGGAATGTCTTCTCATG CTCCGTGATGCATGAGGCTCTGCACAACCACTACACACAGAAGAGCCTCTCCCTG TCTCTGGGTAAA | 164 |

What is claimed:

1. A method of in vitro inhibiting T-cell mediated B-cell antibody production, comprising contacting a portion of human T-cells with an effective amount of a human CD27 antibody or antigen-binding fragment thereof comprising a light chain variable region and a heavy chain variable region, said light chain variable region comprising:
 a complementarity determining region light chain 1 (CDRL1) amino acid sequence selected from the group consisting of SEQ ID NOs: 59-66 and 158;
 a CDRL2 amino acid sequence selected from the group consisting of SEQ ID NOs: 67-74; and
 a CDRL3 amino acid sequence of SEQ ID NO: 75;
said heavy chain variable region comprising:
 a CDRH1 amino acid sequence selected from the group consisting of SEQ ID NOs: 42-45 and 161;
 a CDRH2 amino acid sequence selected from the group consisting of SEQ ID NOs: 46-57, 156, and 157; and
 a CDRH3 amino acid sequence of SEQ ID NO: 58, and the antibody or antigen binding portion thereof inhibits the activation of CD27 on said human T-cells in the presence of human CD70 protein.

2. The method of claim 1, wherein the contacting step comprises contacting the T-cells with an effective amount of a human CD27 antibody or antigen-binding fragment thereof comprising a light chain variable region and a heavy chain variable region, said light chain variable region comprising:
 a CDRL1 amino acid sequence of SEQ ID NO: 62;
 a CDRL2 amino acid sequence of SEQ ID NO: 68; and
 a CDRL3 amino acid sequence of SEQ ID NO: 75, and said heavy chain variable region comprising:
 a CDRH1 amino acid sequence selected from the group consisting of SEQ ID NOs: 44 and 161;
 a CDRH2 amino acid sequence of SEQ ID NO: 47; and
 a CDRH3 amino acid sequence of SEQ ID NO: 58.

3. The method of claim 1, wherein the contacting step comprises contacting the T-cells with an effective amount of a human CD27 antibody or antigen-binding fragment thereof comprising a light chain variable amino acid sequence of SEQ ID NO: 143 and a heavy chain variable amino acid sequence of SEQ ID NO: 133.

4. The method of claim 3, wherein the antibody further comprises an IgG4 heavy chain constant region and an IgG4 light chain constant region.

5. The method of claim 4, wherein the heavy chain constant region comprises the amino acid sequence of SEQ ID NO:159 and the light chain constant region comprises the amino acid sequence of SEQ ID NO:160.

* * * * *

SEQUENCE LISTING

<160> NUMBER OF SEQ ID NOS: 176

<210> SEQ ID NO 1
<211> LENGTH: 5
<212> TYPE: PRT
<213> ORGANISM: Artificial Sequence
<220> FEATURE:
<223> OTHER INFORMATION: CDR Heavy Chain Variable Sequence

<400> SEQUENCE: 1

Ser Ser Trp Met Asn
1               5

<210> SEQ ID NO 2
<211> LENGTH: 10
<212> TYPE: PRT
<213> ORGANISM: Artificial Sequence
<220> FEATURE:
<223> OTHER INFORMATION: CDR Heavy Chain Variable Sequence

<400> SEQUENCE: 2

Gly Tyr Ala Phe Ser Ser Ser Trp Met Asn
1               5                   10

<210> SEQ ID NO 3
<211> LENGTH: 17
<212> TYPE: PRT
<213> ORGANISM: Artificial Sequence
<220> FEATURE:
<223> OTHER INFORMATION: CDR Heavy Chain Variable Sequence

<400> SEQUENCE: 3

Arg Ile Tyr Pro Gly Asp Gly Asp Thr Asn Tyr Asn Gly Lys Phe Lys
1               5                   10                  15

Gly

<210> SEQ ID NO 4
<211> LENGTH: 12
<212> TYPE: PRT
<213> ORGANISM: Artificial Sequence
<220> FEATURE:
<223> OTHER INFORMATION: CDR Heavy Variable Sequence

<400> SEQUENCE: 4

Arg Ile Tyr Pro Gly Asp Gly Asp Thr Asn Tyr Ser
1               5                   10

<210> SEQ ID NO 5
<211> LENGTH: 12
<212> TYPE: PRT
<213> ORGANISM: Artificial Sequence
<220> FEATURE:
<223> OTHER INFORMATION: CDR Heavy Chain Variable Sequence

<400> SEQUENCE: 5

Arg Ile Phe Val Arg Asp Gly Asp Thr Asn Tyr Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: CDR Heavy Chain Variable Sequence

<400> SEQUENCE: 6

Arg Ile Tyr Val Gly Asp Gly Asp Thr Asn Tyr Ser
1               5                   10

<210> SEQ ID NO 7
<211> LENGTH: 12
<212> TYPE: PRT
<213> ORGANISM: Artificial Sequence
<220> FEATURE:
<223> OTHER INFORMATION: CDR Heavy Chain Variable Sequence

<400> SEQUENCE: 7

Arg Ile Tyr Ala Gly Asp Gly Asp Thr Asn Tyr Ser
1               5                   10

```
<210> SEQ ID NO 8
<211> LENGTH: 12
<212> TYPE: PRT
<213> ORGANISM: Artificial Sequence
<220> FEATURE:
<223> OTHER INFORMATION: CDR Heavy Chain Variable Sequence

<400> SEQUENCE: 8

Arg Ile Tyr Ala Arg Asp Gly Asp Thr Asn Tyr Ser
1               5                   10

<210> SEQ ID NO 9
<211> LENGTH: 12
<212> TYPE: PRT
<213> ORGANISM: Artificial Sequence
<220> FEATURE:
<223> OTHER INFORMATION: CDR Heavy Chain Variable Sequence

<400> SEQUENCE: 9

Arg Ile Tyr Gly Arg Asp Gly Asp Thr Asn Tyr Ser
1               5                   10

<210> SEQ ID NO 10
<211> LENGTH: 12
<212> TYPE: PRT
<213> ORGANISM: Artificial Sequence
<220> FEATURE:
<223> OTHER INFORMATION: CDR Heavy Chain Variable Sequence

<400> SEQUENCE: 10

Arg Ile Tyr Ala Asn Asp Gly Asp Thr Asn Tyr Ser
1               5                   10

<210> SEQ ID NO 11
<211> LENGTH: 12
<212> TYPE: PRT
<213> ORGANISM: Artificial Sequence
<220> FEATURE:
<223> OTHER INFORMATION: CDR Heavy Chain Variable Sequence

<400> SEQUENCE: 11

Arg Ile Tyr Gly Gly Asp Gly Asp Thr Asn Tyr Ser
1               5                   10

<210> SEQ ID NO 12
<211> LENGTH: 12
<212> TYPE: PRT
<213> ORGANISM: Artificial Sequence
<220> FEATURE:
<223> OTHER INFORMATION: CDR Heavy Chain Variable Sequence

<400> SEQUENCE: 12

Arg Ile Tyr Ser Gly Asp Gly Asp Thr Asn Tyr Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: CDR Heavy Chain Variable Sequence

<400> SEQUENCE: 13

Arg Ile Tyr Ser Arg Asp Gly Asp Thr Asn Tyr Ser
1               5                   10
```

```
<210> SEQ ID NO 14
<211> LENGTH: 12
<212> TYPE: PRT
<213> ORGANISM: Artificial Sequence
<220> FEATURE:
<223> OTHER INFORMATION: CDR Heavy Chain Variable Sequence

<400> SEQUENCE: 14

Arg Ile Tyr Ala Gly Asp Gly Asp Thr Ala Tyr Ser
1               5                   10

<210> SEQ ID NO 15
<211> LENGTH: 12
<212> TYPE: PRT
<213> ORGANISM: Artificial Sequence
<220> FEATURE:
<223> OTHER INFORMATION: CDR Heavy Chain Variable Sequence

<400> SEQUENCE: 15

Arg Ile Tyr Ala Gly Asp Gly Asp Thr Asn Tyr Ala
1               5                   10

<210> SEQ ID NO 16
<211> LENGTH: 12
<212> TYPE: PRT
<213> ORGANISM: Artificial Sequence
<220> FEATURE:
<223> OTHER INFORMATION: CDR Heavy Chain Variable Sequence

<400> SEQUENCE: 16

Arg Ile Tyr Ala Gly Asp Ala Asp Thr Ala Tyr Ser
1               5                   10

<210> SEQ ID NO 17
<211> LENGTH: 12
<212> TYPE: PRT
<213> ORGANISM: Artificial Sequence
<220> FEATURE:
<223> OTHER INFORMATION: CDR Heavy Chain Variable Sequence

<400> SEQUENCE: 17

Arg Ile Tyr Ala Gly Asp Ala Asp Thr Asn Tyr Ala
1               5                   10

<210> SEQ ID NO 18
<211> LENGTH: 17
<212> TYPE: PRT
<213> ORGANISM: Artificial Sequence
<220> FEATURE:
<223> OTHER INFORMATION: CDR Heavy Chain Variable Sequence

<400> SEQUENCE: 18

Arg Ile Tyr Pro Gly Asp Gly Asp Thr Asn Tyr Asn Gly Lys Phe Lys
1               5                   10                  15

Gly

<210> SEQ ID NO 19
<211> LENGTH: 17
<212> TYPE: PRT
<213> ORGANISM: Artificial Sequence
<220> FEATURE:
<223> OTHER INFORMATION: CDR Heavy Chain Variable Sequence

<400> SEQUENCE: 19

Arg Ile Tyr Ser Gly Asp Gly Asp Thr Asn Tyr Asn Gly Lys Phe Lys
1               5                   10                  15
```

Gly

<210> SEQ ID NO 20
<211> LENGTH: 17
<212> TYPE: PRT
<213> ORGANISM: Artificial Sequence
<220> FEATURE:
<223> OTHER INFORMATION: CDR Heavy Chain Variable Sequence

<400> SEQUENCE: 20

Arg Ile Tyr Ser Gly Asp Ala Asp Thr Asn Tyr Ala Gln Lys Phe Lys
1               5                   10                  15

Gly

<210> SEQ ID NO 21
<211> LENGTH: 17
<212> TYPE: PRT
<213> ORGANISM: Artificial Sequence
<220> FEATURE:
<223> OTHER INFORMATION: CDR Heavy Chain Variable Sequence

<400> SEQUENCE: 21

Arg Ile Tyr Ser Gly Asp Ala Asp Thr Asn Tyr Asn Gln Lys Phe Lys
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: CDR Heavy Chain Variable Sequence

<400> SEQUENCE: 22

Arg Ile Tyr Gln Gly Asp Gly Asp Thr Asn Tyr Asn Gly Lys Phe Lys
1               5                   10                  15

Gly

<210> SEQ ID NO 23
<211> LENGTH: 11
<212> TYPE: PRT
<213> ORGANISM: Artificial Sequence
<220> FEATURE:
<223> OTHER INFORMATION: CDR Heavy Chain Variable Sequence

<400> SEQUENCE: 23

Ser Asp Tyr Tyr Gly Asp Tyr Gly Phe Ala Tyr
1               5                   10

<210> SEQ ID NO 24
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 24

Lys Ala Ser Gln Ser Val Asp Tyr Ala Gly Asp Ser Tyr Met Asn
1               5                   10                  15

<210> SEQ ID NO 25
<211> LENGTH: 15
<212> TYPE: PRT
<213> ORGANISM: Artificial Sequence -continued

```
<220> FEATURE:
<223> OTHER INFORMATION: CDR Light Chain Variable Sequence

<400> SEQUENCE: 25

Lys Ala Ser Gln Ser Val Asp Tyr Ala Gly Asp Ser Phe Met Asn
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 26

Lys Ala Ser Gln Ser Val Asp Tyr Ala Gly Asp Ser Trp Met Asn
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 27

Lys Ala Ser Gln Ser Val Asp Tyr Ala Gly Ser Ser Phe Met Asn
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 28

Lys Ala Ser Gln Ser Val Asp Trp Ala Gly His Ser Trp Met Asn
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 29

Lys Ala Ser Gln Ser Val Asp Tyr Ala Gly Glu Ser Phe Met Asn
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 30

Lys Ala Ser Gln Ser Val Asp Tyr Phe Ser Glu Ser Tyr Met Asn
1               5                   10                  15

<210> SEQ ID NO 31
<211> LENGTH: 15
<212> TYPE: PRT
<213> ORGANISM: Artificial Sequence
<220> FEATURE:
```

```
<223> OTHER INFORMATION: CDR Light Chain Variable Sequence

<400> SEQUENCE: 31

Lys Ala Ser Gln Ser Val Asp Tyr Ala His Glu Ser Phe Met Asn
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 32

Lys Ala Ser Gln Ser Val Asp Tyr Phe Gly Asp Ser Leu Met Asn
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 33

Lys Ala Ser Gln Ser Val Asp Tyr Phe Arg Thr Ser Phe Met Asn
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 34

Lys Ala Ser Gln Ser Val Asp Tyr Val Gly Thr Ser Phe Met Asn
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 35

Lys Ala Ser Gln Ser Val Asp Tyr Trp Ser Asp Ser Phe Met Asn
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 36

Lys Ala Ser Gln Ser Val Asp Tyr Tyr Asn Ser Ser Phe Met Asn
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: CDR Light Chain Variable Sequence
```

<400> SEQUENCE: 37

Ala Ala Ser Asn Leu Glu Ser
1               5

<210> SEQ ID NO 38
<211> LENGTH: 7
<212> TYPE: PRT
<213> ORGANISM: Artificial Sequence
<220> FEATURE:
<223> OTHER INFORMATION: CD27 Sequence

<400> SEQUENCE: 38

Val Ala Ser Asn Leu Glu Ser
1               5

<210> SEQ ID NO 39
<211> LENGTH: 7
<212> TYPE: PRT
<213> ORGANISM: Artificial Sequence
<220> FEATURE:
<223> OTHER INFORMATION: CDR Light Chain Variable Sequence

<400> SEQUENCE: 39

Thr Ala Ser Asn Leu Glu Ser
1               5

<210> SEQ ID NO 40
<211> LENGTH: 7
<212> TYPE: PRT
<213> ORGANISM: Artificial Sequence
<220> FEATURE:
<223> OTHER INFORMATION: CDR Light Chain Variable Sequence

<400> SEQUENCE: 40

Glu Ala Ser Asn Leu Glu Ser
1               5

<210> SEQ ID NO 41
<211> LENGTH: 9
<212> TYPE: PRT
<213> ORGANISM: Artificial Sequence
<220> FEATURE:
<223> OTHER INFORMATION: CDR Light Chain Variable Sequence

<400> SEQUENCE: 41

Gln Gln Ser Asn Glu Asp Pro Tyr Thr
1               5

<210> SEQ ID NO 42
<211> LENGTH: 5
<212> TYPE: PRT
<213> ORGANISM: Artificial Sequence
<220> FEATURE:
<223> OTHER INFORMATION: CDR Heavy Chain Variable Sequence

<400> SEQUENCE: 42

Ser Tyr Thr Met Ser
1               5

<210> SEQ ID NO 43
<211> LENGTH: 10
<212> TYPE: PRT
<213> ORGANISM: Artificial Sequence
<220> FEATURE:
<223> OTHER INFORMATION: CDR Heavy Chain Variable Sequence

```
<400> SEQUENCE: 43

Gly Phe Thr Phe Ser Ser Tyr Thr Met Ser
1               5                   10

<210> SEQ ID NO 44
<211> LENGTH: 10
<212> TYPE: PRT
<213> ORGANISM: Artificial Sequence
<220> FEATURE:
<223> OTHER INFORMATION: CDR Heavy Chain Variable Sequence

<400> SEQUENCE: 44

Gly Phe Thr Phe Ser Ser Tyr Gly Met Ser
1               5                   10

<210> SEQ ID NO 45
<211> LENGTH: 10
<212> TYPE: PRT
<213> ORGANISM: Artificial Sequence
<220> FEATURE:
<223> OTHER INFORMATION: CDR Heavy Chain Variable Sequence

<400> SEQUENCE: 45

Gly Phe Thr Phe Ser Ser Tyr Ser Met Ser
1               5                   10

<210> SEQ ID NO 46
<211> LENGTH: 17
<212> TYPE: PRT
<213> ORGANISM: Artificial Sequence
<220> FEATURE:
<223> OTHER INFORMATION: CDR Heavy Chain Variable Sequence

<400> SEQUENCE: 46

Tyr Ile Ser Ser Gly Gly Gly Asn Thr Tyr Tyr Pro Asp Ser Val Lys
1               5                   10                  15

Gly

<210> SEQ ID NO 47
<211> LENGTH: 17
<212> TYPE: PRT
<213> ORGANISM: Artificial Sequence
<220> FEATURE:
<223> OTHER INFORMATION: CDR Heavy Chain Variable Sequence

<400> SEQUENCE: 47

Tyr Ile Asp Glu Gly Gly Gly Gln Thr Ile Tyr Pro Asp Ser Val Lys
1               5                   10                  15

Gly

<210> SEQ ID NO 48
<211> LENGTH: 17
<212> TYPE: PRT
<213> ORGANISM: Artificial Sequence
<220> FEATURE:
<223> OTHER INFORMATION: CDR Heavy Chain Variable Sequence

<400> SEQUENCE: 48

Tyr Ile Asp Ala Gly Gly Gly Phe Thr Ile Tyr Pro Asp Ser Val Lys
1               5                   10                  15

Gly

<210> SEQ ID NO 49
<211> LENGTH: 17
```

```
<212> TYPE: PRT
<213> ORGANISM: Artificial Sequence
<220> FEATURE:
<223> OTHER INFORMATION: CDR Heavy Chain Variable Sequence

<400> SEQUENCE: 49

His Ile Asp Ala Gly Gly Gly Arg Thr Trp Tyr Pro Asp Ser Val Lys
1               5                   10                  15
Gly

<210> SEQ ID NO 50
<211> LENGTH: 17
<212> TYPE: PRT
<213> ORGANISM: Artificial Sequence
<220> FEATURE:
<223> OTHER INFORMATION: CDR Heavy Chain Variable Sequence

<400> SEQUENCE: 50

Tyr Ile Asp Arg Gly Gly Gly Val Thr Ile Tyr Pro Asp Ser Val Lys
1               5                   10                  15
Gly

<210> SEQ ID NO 51
<211> LENGTH: 17
<212> TYPE: PRT
<213> ORGANISM: Artificial Sequence
<220> FEATURE:
<223> OTHER INFORMATION: CDR Heavy Chain Variable Sequence

<400> SEQUENCE: 51

Ala Ile Asp His Gly Gly Gly Arg Thr Tyr Tyr Pro Asp Ser Val Lys
1               5                   10                  15
Gly

<210> SEQ ID NO 52
<211> LENGTH: 17
<212> TYPE: PRT
<213> ORGANISM: Artificial Sequence
<220> FEATURE:
<223> OTHER INFORMATION: CDR Heavy Chain Variable Sequence

<400> SEQUENCE: 52

Ala Ile Asp His Gly Gly Gly Arg Thr Trp Tyr Pro Asp Ser Val Lys
1               5                   10                  15
Gly

<210> SEQ ID NO 53
<211> LENGTH: 17
<212> TYPE: PRT
<213> ORGANISM: Artificial Sequence
<220> FEATURE:
<223> OTHER INFORMATION: CDR Heavy Chain Variable Sequence

<400> SEQUENCE: 53

Ala Ile Asp His Gly Gly Gly Gln Thr Leu Tyr Pro Asp Ser Val Lys
1               5                   10                  15
Gly

<210> SEQ ID NO 54
<211> LENGTH: 17
<212> TYPE: PRT
<213> ORGANISM: Artificial Sequence
<220> FEATURE:
<223> OTHER INFORMATION: CDR Heavy Chain Variable Sequence
```

```
<400> SEQUENCE: 54

Tyr Ile Ser Gly Gly Gly Gly Gln Thr Leu Tyr Pro Asp Ser Val Lys
1               5                   10                  15

Gly

<210> SEQ ID NO 55
<211> LENGTH: 17
<212> TYPE: PRT
<213> ORGANISM: Artificial Sequence
<220> FEATURE:
<223> OTHER INFORMATION: CDR Heavy Chain Variable Sequence

<400> SEQUENCE: 55

Thr Ile Asp Arg Gly Gly Gly Ser Thr Trp Tyr Pro Asp Ser Val Lys
1               5                   10                  15

Gly

<210> SEQ ID NO 56
<211> LENGTH: 17
<212> TYPE: PRT
<213> ORGANISM: Artificial Sequence
<220> FEATURE:
<223> OTHER INFORMATION: CDR Heavy Chain Variable Sequence

<400> SEQUENCE: 56

Ala Ile Asp Gly Gly Gly Gly Ala Thr Tyr Tyr Pro Asp Ser Val Lys
1               5                   10                  15

Gly

<210> SEQ ID NO 57
<211> LENGTH: 17
<212> TYPE: PRT
<213> ORGANISM: Artificial Sequence
<220> FEATURE:
<223> OTHER INFORMATION: CDR Heavy Chain Variable Sequence

<400> SEQUENCE: 57

Val Ile Asp His Gly Gly Gly Ser Thr His Tyr Pro Asp Ser Val Lys
1               5                   10                  15

Gly

<210> SEQ ID NO 58
<211> LENGTH: 8
<212> TYPE: PRT
<213> ORGANISM: Artificial Sequence
<220> FEATURE:
<223> OTHER INFORMATION: CDR Heavy Chain Variable Sequence

<400> SEQUENCE: 58

His Arg Gly Asn Pro Phe Asp Tyr
1               5

<210> SEQ ID NO 59
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 59

Arg Ala Ser Lys Ser Val Ser Thr Ser Gly Tyr Ser Phe Met His
1               5                   10                  15
```

<210> SEQ ID NO 60
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 60

Arg Ala Ser Lys Ser Val Ser Ala Trp Gly Tyr Ser Phe Met His
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 61

Arg Ala Ser Lys Ser Val Ser His Val Arg Trp Ser Phe Met His
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 62

Arg Ala Ser Lys Ser Val Ser Glu Gly Arg Trp Ser Phe Met His
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 63

Arg Ala Ser Lys Ser Val Ser Leu Asp Arg Trp Ser Phe Met His
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 64

Arg Ala Ser Lys Ser Val Ser Tyr Val Arg Trp Ser Phe Met His
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 65

Arg Ala Ser Lys Ser Val Ser His Ile Arg Trp Ser Phe Met His
1               5                   10                  15

```
<210> SEQ ID NO 66
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 66

Arg Ala Ser Lys Ser Val Ser His Val Arg Trp Ser Phe Met His
1               5                   10                  15

<210> SEQ ID NO 67
<211> LENGTH: 7
<212> TYPE: PRT
<213> ORGANISM: Artificial Sequence
<220> FEATURE:
<223> OTHER INFORMATION: CDR Light Chain Variable Sequence

<400> SEQUENCE: 67

Leu Ala Ser Asn Leu Glu Ser
1               5

<210> SEQ ID NO 68
<211> LENGTH: 7
<212> TYPE: PRT
<213> ORGANISM: Artificial Sequence
<220> FEATURE:
<223> OTHER INFORMATION: CDR Light Chain Variable Sequence

<400> SEQUENCE: 68

Val Ala Ser Arg Leu Glu Ser
1               5

<210> SEQ ID NO 69
<211> LENGTH: 7
<212> TYPE: PRT
<213> ORGANISM: Artificial Sequence
<220> FEATURE:
<223> OTHER INFORMATION: CDR Light Chain Variable Sequence

<400> SEQUENCE: 69

Leu Ala Ser Lys Leu Glu Ser
1               5

<210> SEQ ID NO 70
<211> LENGTH: 7
<212> TYPE: PRT
<213> ORGANISM: Artificial Sequence
<220> FEATURE:
<223> OTHER INFORMATION: CDR Light Chain Variable Sequence

<400> SEQUENCE: 70

Val Gly Asn Arg Leu Glu Asp
1               5

<210> SEQ ID NO 71
<211> LENGTH: 7
<212> TYPE: PRT
<213> ORGANISM: Artificial Sequence
<220> FEATURE:
<223> OTHER INFORMATION: CDR Light Chain Variable Sequence

<400> SEQUENCE: 71

Val Gly Asp Arg Arg Gln Glu
1               5

<210> SEQ ID NO 72
```

<211> LENGTH: 7
<212> TYPE: PRT
<213> ORGANISM: Artificial Sequence
<220> FEATURE:
<223> OTHER INFORMATION: CDR Light Chain Variable Sequence

<400> SEQUENCE: 72

Val Gly Ser Arg Met Ala Phe
1               5

<210> SEQ ID NO 73
<211> LENGTH: 7
<212> TYPE: PRT
<213> ORGANISM: Artificial Sequence
<220> FEATURE:
<223> OTHER INFORMATION: CDR Light Chain Variable Sequence

<400> SEQUENCE: 73

Val Gly Asp Arg Ala Asn Trp
1               5

<210> SEQ ID NO 74
<211> LENGTH: 7
<212> TYPE: PRT
<213> ORGANISM: Artificial Sequence
<220> FEATURE:
<223> OTHER INFORMATION: CDR Light Chain Variable Sequence

<400> SEQUENCE: 74

Val Gly Ser Arg Leu Asp Tyr
1               5

<210> SEQ ID NO 75
<211> LENGTH: 9
<212> TYPE: PRT
<213> ORGANISM: Artificial Sequence
<220> FEATURE:
<223> OTHER INFORMATION: CDR Light Chain Variable Sequence

<400> SEQUENCE: 75

Gln His Ser Arg Glu Leu Pro Trp Thr
1               5

<210> SEQ ID NO 76
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 76

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met Asn Trp Val Lys Gln Arg Pro Gly Arg Gly Leu Glu Trp Ile
        35                  40                  45

Gly Arg Ile His Pro Ser Asp Ser Glu Thr His Tyr Asn Gln Asn Phe
    50                  55                  60

Lys Ser Lys Ala Thr Leu Thr Val Asp Lys Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Pro Val Leu Tyr Gly Asp Tyr Gly Phe Pro Cys Trp Gly Gln

```
                    100                 105                 110

Gly Thr Leu Val Thr Val Ser Ala
        115                 120

<210> SEQ ID NO 77
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 77

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 78
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 78

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Trp Asp Gly Gly Asn Tyr Phe Phe Asp Tyr Trp Gly Gln
            100                 105                 110

Gly Thr Thr Leu Thr Val Ser Ser
        115                 120

<210> SEQ ID NO 79
<211> LENGTH: 107
<212> TYPE: PRT
<213> ORGANISM: Artificial Sequence
<220> FEATURE:
<223> OTHER INFORMATION: Light Chain Variable Sequence

<400> SEQUENCE: 79
```

```
Asp Ile Val Met Thr Gln Ser His Lys Phe Met Ser Thr Ser Val Gly
1               5                   10                  15

Asp Arg Val Ser Ile Thr Cys Met Ala Ser Gln Asp Val Gly Thr Ala
            20                  25                  30

Val Ala Trp Tyr Gln Arg Pro Gly Gln Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ser Gly Thr Lys Leu Glu Ile Lys
            100                 105
```

<210> SEQ ID NO 80
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 80

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ala
        115                 120
```

<210> SEQ ID NO 81
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 81

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Ala
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
```

```
                65                  70                  75                  80
Pro Val Glu Glu Glu Asp Ala Ala Thr Tyr Tyr Cys Gln Gln Ser Asn
                    85                  90                  95
Glu Asp Pro Tyr Thr Phe Gly Gly Gly Thr Lys Leu Glu Ile Lys
                100                 105                 110

<210> SEQ ID NO 82
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 82

Asp Ile Val Met Thr Gln Ser Pro Asp Ser Leu Ala Val Ser Leu Gly
1               5                   10                  15
Glu Arg Ala Thr Ile Asn Cys Lys Ala Ser Gln Ser Val Asp Tyr Ala
                20                  25                  30
Gly Asp Ser Tyr Met Asn Trp Tyr Gln Gln Lys Pro Gly Gln Pro Pro
            35                  40                  45
Lys Leu Leu Ile Tyr Ala Ala Ser Asn Leu Glu Ser Gly Val Pro Asp
        50                  55                  60
Arg Phe Ser Gly Ser Gly Ser Gly Thr Asp Phe Thr Leu Thr Ile Ser
65                  70                  75                  80
Ser Leu Gln Ala Glu Asp Val Ala Val Tyr Tyr Cys Gln Gln Ser Asn
                85                  90                  95
Glu Asp Pro Tyr Thr Phe Gly Gln Gly Thr Lys Leu Glu Ile Lys
                100                 105                 110

<210> SEQ ID NO 83
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 83

Asp Ile Val Met Thr Gln Ser Pro Asp Ser Leu Ala Val Ser Leu Gly
1               5                   10                  15
Glu Arg Ala Thr Ile Asn Cys Lys Ala Ser Gln Ser Val Asp Tyr Ala
                20                  25                  30
Gly Asp Ser Phe Met Asn Trp Tyr Gln Gln Lys Pro Gly Gln Pro Pro
            35                  40                  45
Lys Leu Leu Ile Tyr Ala Ala Ser Asn Leu Glu Ser Gly Val Pro Asp
        50                  55                  60
Arg Phe Ser Gly Ser Gly Ser Gly Thr Asp Phe Thr Leu Thr Ile Ser
65                  70                  75                  80
Ser Leu Gln Ala Glu Asp Val Ala Val Tyr Tyr Cys Gln Gln Ser Asn
                85                  90                  95
Glu Asp Pro Tyr Thr Phe Gly Gln Gly Thr Lys Leu Glu Ile Lys
                100                 105                 110

<210> SEQ ID NO 84
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 84
```

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Ala
            20                  25                  30

Gly Asp Ser Trp Met Asn Trp Tyr Gln Gln Lys Pro Gly Gln Pro Pro
        35                  40                  45

Lys Leu Leu Ile Tyr Val Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 85
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 85

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Ala
            20                  25                  30

Gly Asp Ser Trp Met Asn Trp Tyr Gln Gln Lys Pro Gly Gln Pro Pro
        35                  40                  45

Lys Leu Leu Ile Tyr Thr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Leu Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 86
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 86

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Trp Ala
            20                  25                  30

Gly His Ser Trp Met Asn Trp Tyr Gln Gln Lys Pro Gly Gln Pro Pro
        35                  40                  45

Lys Leu Leu Ile Tyr Thr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn

```
                      85                  90                  95

Glu Asp Pro Tyr Thr Phe Gly Gln Gly Thr Lys Leu Glu Ile Lys
            100                 105                 110

<210> SEQ ID NO 87
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 87

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Trp Ala
            20                  25                  30

Gly His Ser Trp Met Asn Trp Tyr Gln Gln Lys Pro Gly Gln Pro Pro
        35                  40                  45

Lys Leu Leu Ile Tyr Thr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 88
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 88

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Ala
            20                  25                  30

Gly Ser Ser Phe Met Asn Trp Tyr Gln Gln Lys Pro Gly Gln Pro Pro
        35                  40                  45

Lys Leu Leu Ile Tyr Glu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 89
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 89

Asp Ile Val Met Thr Gln Ser Pro Asp Ser Leu Ala Val Ser Leu Gly
1               5                   10                  15
```

```
Glu Arg Ala Thr Ile Asn Cys Lys Ala Ser Gln Ser Val Asp Tyr Ala
            20                  25                  30

Gly Glu Ser Phe Met Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 90
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 90

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Ser Val Asp Tyr Ala
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 91
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 91

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Ser Val Asp Tyr Phe
            20                  25                  30

Ser Glu Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                85                  90                  95

Glu Asp Pro Tyr Thr Phe Gly Gln Gly Thr Lys Val Glu Ile Lys
```

<210> SEQ ID NO 92
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Ala
            20                  25                  30

His Glu Ser Phe Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Tyr Thr Phe Gly Gln Gly Thr Lys Val Glu Ile Lys
            100                 105                 110

<210> SEQ ID NO 93
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Phe
            20                  25                  30

Gly Asp Ser Leu Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Tyr Thr Phe Gly Gln Gly Thr Lys Val Glu Ile Lys
            100                 105                 110

<210> SEQ ID NO 94
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Ala
            20                  25                  30

Gly Asp Ser Phe Met Asn Trp Tyr Gln Gln Lys Pro Gly Lys Ala Pro
            35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Tyr Thr Phe Gly Gln Gly Thr Lys Val Glu Ile Lys
            100                 105                 110

<210> SEQ ID NO 95
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Ala
            20                  25                  30

Gly Glu Ser Phe Met Asn Trp Tyr Gln Gln Lys Pro Gly Lys Ala Pro
            35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Tyr Thr Phe Gly Gln Gly Thr Lys Val Glu Ile Lys
            100                 105                 110

<210> SEQ ID NO 96
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Ala
            20                  25                  30

Gly Glu Ser Phe Met Asn Trp Tyr Gln Gln Lys Pro Gly Lys Ala Pro
            35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Tyr Thr Phe Gly Gln Gly Thr Lys Val Glu Ile Lys
            100                 105                 110

<210> SEQ ID NO 97
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 97

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Ala
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Tyr Thr Phe Gly Gln Gly Thr Lys Val Glu Ile Lys
            100                 105                 110
```

<210> SEQ ID NO 98
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 98

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Phe
            20                  25                  30

Arg Thr Ser Phe Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Tyr Thr Phe Gly Gln Gly Thr Lys Val Glu Ile Lys
            100                 105                 110
```

<210> SEQ ID NO 99
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 99

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Val
            20                  25                  30

Gly Thr Ser Phe Met Asn Trp Tyr Gln Gln Lys Pro Gly Lys Ala Pro
        35                  40                  45
```

```
Lys Leu Leu Ile Tyr Ala Ala Ser Asn Leu Glu Ser Gly Val Pro Ser
         50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                 85                  90                  95

Glu Asp Pro Tyr Thr Phe Gly Gln Gly Thr Lys Val Glu Ile Lys
            100                 105                 110

<210> SEQ ID NO 100
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 100

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Ser Val Asp Tyr Trp
             20                  25                  30

Ser Asp Ser Phe Met Asn Trp Tyr Gln Gln Lys Pro Gly Lys Ala Pro
         35                  40                  45

Lys Leu Leu Ile Tyr Ala Ala Ser Asn Leu Glu Ser Gly Val Pro Ser
         50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                 85                  90                  95

Glu Asp Pro Tyr Thr Phe Gly Gln Gly Thr Lys Val Glu Ile Lys
            100                 105                 110

<210> SEQ ID NO 101
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 101

Asp Ile Gln Met Thr Gln Ser Pro Ser Ser Leu Ser Ala Ser Val Gly
 1               5                  10                  15

Asp Arg Val Ala Ile Thr Cys Lys Ala Ser Gln Ser Val Asp Tyr Tyr
             20                  25                  30

Asn Ser Ser Phe Met Asn Trp Tyr Gln Gln Lys Pro Gly Lys Ala Pro
         35                  40                  45

Lys Leu Leu Ile Tyr Ala Ala Ser Asn Leu Glu Ser Gly Val Pro Ser
         50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                 85                  90                  95

Glu Asp Pro Tyr Thr Phe Gly Gln Gly Thr Lys Val Glu Ile Lys
            100                 105                 110

<210> SEQ ID NO 102
<211> LENGTH: 120
<212> TYPE: PRT
```

<213> ORGANISM: Artificial Sequence
<220> FEATURE:
<223> OTHER INFORMATION: Heavy Chain Variable Sequence

<400> SEQUENCE: 102

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Met Asn Trp Val Arg Gln Met Pro Gly Lys Gly Leu Glu Trp Met
        35                  40                  45

Gly Arg Ile Tyr Pro Gly Asp Gly Asp Thr Asn Tyr Asn Gly Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120

<210> SEQ ID NO 103
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 103

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Met Asn Trp Val Arg Gln Met Pro Gly Lys Gly Leu Glu Trp Met
        35                  40                  45

Gly Arg Ile Tyr Ser Gly Asp Gly Asp Thr Asn Tyr Asn Gly Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120

<210> SEQ ID NO 104
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 104

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Met Asn Trp Val Arg Gln Met Pro Gly Lys Gly Leu Glu Trp Met
            35                  40                  45

Gly Arg Ile Tyr Ser Gly Asp Ala Asp Thr Asn Tyr Ala Gln Lys Phe
 50                  55                  60

Lys Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
            85                  90                  95

Ala Arg Ser Asp Tyr Tyr Gly Asp Tyr Gly Phe Ala Tyr Trp Gly Gln
           100                 105                 110

Gly Thr Leu Val Thr Val Ser Ser
           115                 120

<210> SEQ ID NO 105
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 105

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ala Phe Ser Ser Ser
            20                  25                  30

Trp Met Asn Trp Val Arg Gln Met Pro Gly Lys Gly Leu Glu Trp Met
            35                  40                  45

Gly Arg Ile Tyr Ser Gly Asp Ala Asp Thr Asn Tyr Asn Gln Lys Phe
 50                  55                  60

Lys Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
            85                  90                  95

Ala Arg Ser Asp Tyr Tyr Gly Asp Tyr Gly Phe Ala Tyr Trp Gly Gln
           100                 105                 110

Gly Thr Leu Val Thr Val Ser Ser
           115                 120

<210> SEQ ID NO 106
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 106

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Met
            35                  40                  45

Gly Arg Ile Tyr Pro Gly Asp Gly Asp Thr Asn Tyr Asn Gly Lys Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys

```
                    85                  90                  95
Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120

<210> SEQ ID NO 107
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 107

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Met
        35                  40                  45

Gly Arg Ile Tyr Ser Gly Asp Gly Asp Thr Asn Tyr Asn Gly Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120

<210> SEQ ID NO 108
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 108

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Met
        35                  40                  45

Gly Arg Ile Tyr Ser Gly Asp Ala Asp Thr Asn Tyr Ala Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120

<210> SEQ ID NO 109
<211> LENGTH: 120
```

```
<212> TYPE: PRT
<213> ORGANISM: Artificial Sequence
<220> FEATURE:
<223> OTHER INFORMATION: Heavy Chain Variable Sequence

<400> SEQUENCE: 109

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Met
        35                  40                  45

Gly Arg Ile Tyr Ser Gly Asp Ala Asp Thr Asn Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120

<210> SEQ ID NO 110
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Met
        35                  40                  45

Gly Arg Ile Tyr Gln Gly Asp Gly Asp Thr Asn Tyr Asn Gly Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120

<210> SEQ ID NO 111
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 111

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
```

```
                     20                  25                  30

Trp Met Asn Trp Val Arg Gln Met Pro Gly Lys Gly Leu Glu Trp Met
                35                  40                  45

Gly Arg Ile Tyr Pro Gly Asp Gly Asp Thr Asn Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Asp Tyr Tyr Gly Asp Tyr Gly Phe Ala Tyr Trp Gly Gln
                100                 105                 110

Gly Thr Leu Val Thr Val Ser Ser
                115                 120

<210> SEQ ID NO 112
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 112

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
                20                  25                  30

Trp Met Asn Trp Val Arg Gln Met Pro Gly Lys Gly Leu Glu Trp Met
                35                  40                  45

Gly Arg Ile Tyr Pro Gly Asp Gly Asp Thr Asn Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ala Asp Tyr Tyr Gly Asp Tyr Gly Phe Gly Tyr Trp Gly Gln
                100                 105                 110

Gly Thr Leu Val Thr Val Ser Ser
                115                 120

<210> SEQ ID NO 113
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 113

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
                20                  25                  30

Trp Met Asn Trp Val Arg Gln Met Pro Gly Lys Gly Leu Glu Trp Met
                35                  40                  45

Gly Arg Ile Phe Val Arg Asp Gly Asp Thr Asn Tyr Ser Pro Ser Phe
        50                  55                  60

Gln Gly Gln Val Thr Ile Ser Ala Asp Lys Ser Ile Ser Thr Ala Tyr
65                  70                  75                  80
```

-continued

Leu Gln Trp Ser Ser Leu Lys Ala Ser Asp Thr Ala Met Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120

<210> SEQ ID NO 114
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 114

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Met Asn Trp Val Arg Gln Met Pro Gly Lys Gly Leu Glu Trp Met
        35                  40                  45

Gly Arg Ile Tyr Val Gly Asp Gly Asp Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120

<210> SEQ ID NO 115
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 115

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Met Asn Trp Val Arg Gln Met Pro Gly Lys Gly Leu Glu Trp Met
        35                  40                  45

Gly Arg Ile Tyr Ala Gly Asp Gly Asp Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120

<210> SEQ ID NO 116

```
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 116

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Met Asn Trp Val Arg Gln Met Pro Gly Lys Gly Leu Glu Trp Met
        35                  40                  45

Gly Arg Ile Tyr Ala Arg Asp Gly Asp Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120

<210> SEQ ID NO 117
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 117

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Met Asn Trp Val Arg Gln Met Pro Gly Lys Gly Leu Glu Trp Met
        35                  40                  45

Gly Arg Ile Tyr Gly Arg Asp Gly Asp Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120

<210> SEQ ID NO 118
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 118

Glu Val Gln Leu Val Gln Ser Gly Ala Glu Val Lys Lys Pro Gly Glu
1               5                   10                  15
```

Ser Leu Lys Ile Ser Cys Lys Gly Ser Gly Tyr Ala Phe Ser Ser
            20                  25                  30

Trp Met Asn Trp Val Arg Gln Met Pro Gly Lys Gly Leu Glu Trp Met
        35                  40                  45

Gly Arg Ile Tyr Ala Asn Asp Gly Asp Thr Asn Tyr Ser Pro Ser Phe
50                      55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
            115                 120

<210> SEQ ID NO 119
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 119

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Met Asn Trp Val Arg Gln Met Pro Gly Lys Gly Leu Glu Trp Met
        35                  40                  45

Gly Arg Ile Tyr Gly Gly Asp Gly Asp Thr Asn Tyr Ser Pro Ser Phe
50                      55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
            115                 120

<210> SEQ ID NO 120
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 120

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Met Asn Trp Val Arg Gln Met Pro Gly Lys Gly Leu Glu Trp Met
        35                  40                  45

Gly Arg Ile Tyr Ser Gly Asp Gly Asp Thr Asn Tyr Ser Pro Ser Phe
50                      55                  60

Gln Gly Gln Val Thr Ile Ser Ala Asp Lys Ser Ile Ser Thr Ala Tyr
65                  70                  75                  80

```
Leu Gln Trp Ser Ser Leu Lys Ala Ser Asp Thr Ala Met Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120
```

<210> SEQ ID NO 121
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 121

```
Glu Val Gln Leu Val Gln Ser Val Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Met Asn Trp Val Arg Gln Met Pro Gly Lys Gly Leu Glu Trp Met
        35                  40                  45

Gly Arg Ile Tyr Ser Arg Asp Gly Asp Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120
```

<210> SEQ ID NO 122
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 122

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Met Asn Trp Val Arg Gln Met Pro Gly Lys Gly Leu Glu Trp Met
        35                  40                  45

Gly Arg Ile Tyr Ala Gly Asp Gly Asp Thr Ala Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120
```

```
<210> SEQ ID NO 123
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 123

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Met Asn Trp Val Arg Gln Met Pro Gly Lys Gly Leu Glu Trp Met
        35                  40                  45

Gly Arg Ile Tyr Ala Gly Asp Gly Asp Thr Asn Tyr Ala Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120

<210> SEQ ID NO 124
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 124

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Ser Ser
            20                  25                  30

Trp Met Asn Trp Val Arg Gln Met Pro Gly Lys Gly Leu Glu Trp Met
        35                  40                  45

Gly Arg Ile Tyr Ala Gly Asp Ala Asp Thr Ala Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
        115                 120

<210> SEQ ID NO 125
<211> LENGTH: 120
<212> TYPE: PRT
<213> ORGANISM: Artificial Sequence
<220> FEATURE:
<223> OTHER INFORMATION: Heavy Chain Variable Sequence

<400> SEQUENCE: 125

Glu Val Gln Leu Val Gln Ser Gly Ala Glu Val Lys Lys Pro Gly Glu
1               5                   10                  15
```

-continued

Ser Leu Lys Ile Ser Cys Lys Gly Ser Gly Tyr Ala Phe Ser Ser
            20                  25                  30

Trp Met Asn Trp Val Arg Gln Met Pro Gly Lys Gly Leu Glu Trp Met
            35                  40                  45

Gly Arg Ile Tyr Ala Gly Asp Ala Asp Thr Asn Tyr Ala Pro Ser Phe
 50                  55                  60

Gln Gly Gln Val Thr Ile Ser Ala Asp Lys Ser Ile Ser Thr Ala Tyr
65                   70                  75                  80

Leu Gln Trp Ser Ser Leu Lys Ala Ser Asp Thr Ala Met Tyr Tyr Cys
                85                  90                  95

Ala Arg Ser Asp Tyr Tyr Gly Asp Tyr Gly Phe Ala Tyr Trp Gly Gln
            100                 105                 110

Gly Thr Leu Val Thr Val Ser Ser
            115                 120

<210> SEQ ID NO 126
<211> LENGTH: 117
<212> TYPE: PRT
<213> ORGANISM: Artificial Sequence
<220> FEATURE:
<223> OTHER INFORMATION: Heavy Chain Variable Sequence

<400> SEQUENCE: 126

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
            35                  40                  45

Ala Tyr Ile Ser Ser Gly Gly Asn Thr Tyr Tyr Pro Asp Ser Val
 50                  55                  60

Lys Gly Arg Phe Thr Ile Ser Arg Asp Asn Ala Arg Asn Thr Leu Tyr
65                   70                  75                  80

Leu Gln Met Ser Ser Leu Arg Ser Glu Asp Thr Ala Met Tyr Tyr Cys
                85                  90                  95

Ser Arg His Arg Gly Asn Pro Phe Asp Tyr Trp Gly Gln Gly Thr Thr
            100                 105                 110

Leu Thr Val Ser Ser
            115

<210> SEQ ID NO 127
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 127

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Asn Ile His

```
              65                  70                  75                  80
Pro Val Glu Glu Glu Asp Ala Ala Thr Tyr Tyr Cys Gln His Ser Arg
                    85                  90                  95
Glu Leu Pro Trp Thr Phe Gly Gly Gly Thr Lys Leu Glu Ile Lys
                100                 105                 110

<210> SEQ ID NO 128
<211> LENGTH: 117
<212> TYPE: PRT
<213> ORGANISM: Artificial Sequence
<220> FEATURE:
<223> OTHER INFORMATION: Heavy Chain Variable Sequence

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Tyr Ile Ser Ser Gly Gly Gly Asn Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Arg Gly Asn Pro Phe Asp Tyr Trp Gly Gln Gly Thr Leu
                100                 105                 110

Val Thr Val Ser Ser
        115

<210> SEQ ID NO 129
<211> LENGTH: 117
<212> TYPE: PRT
<213> ORGANISM: Artificial Sequence
<220> FEATURE:
<223> OTHER INFORMATION: Heavy Chain Variable Sequence

<400> SEQUENCE: 129

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Ala Ile Asp His Gly Gly Gln Thr Leu Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Asn Pro Phe Asp Tyr Trp Gly Gln Gly Thr Leu
                100                 105                 110

Val Thr Val Ser Ser
        115

<210> SEQ ID NO 130
<211> LENGTH: 117
```

```
<212> TYPE: PRT
<213> ORGANISM: Artificial Sequence
<220> FEATURE:
<223> OTHER INFORMATION: Heavy Chain Variable Sequence

<400> SEQUENCE: 130

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Val Ile Asp His Gly Gly Ser Thr His Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Asn Pro Phe Asp Tyr Trp Gly Gln Gly Thr Leu
            100                 105                 110

Val Thr Val Ser Ser
        115

<210> SEQ ID NO 131
<211> LENGTH: 117
<212> TYPE: PRT
<213> ORGANISM: Artificial Sequence
<220> FEATURE:
<223> OTHER INFORMATION: Heavy Chain Variable Sequence

<400> SEQUENCE: 131

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Ile Arg Gln Ala Pro Gly Lys Gly Leu Glu Trp Val
        35                  40                  45

Ser Tyr Ile Ser Ser Gly Gly Gly Asn Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Asn Pro Phe Asp Tyr Trp Gly Gln Gly Thr Leu
            100                 105                 110

Val Thr Val Ser Ser
        115

<210> SEQ ID NO 132
<211> LENGTH: 117
<212> TYPE: PRT
<213> ORGANISM: Artificial Sequence
<220> FEATURE:
<223> OTHER INFORMATION: Heavy Chain Variable Sequence

<400> SEQUENCE: 132

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
```

20                  25                  30
Gly Met Ser Trp Ile Arg Gln Ala Pro Gly Lys Gly Leu Glu Trp Val
            35                  40                  45

Ser Tyr Ile Asp Arg Gly Gly Val Thr Ile Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Asn Pro Phe Asp Tyr Trp Gly Gln Gly Thr Leu
            100                 105                 110

Val Thr Val Ser Ser
        115

<210> SEQ ID NO 133
<211> LENGTH: 117
<212> TYPE: PRT
<213> ORGANISM: Artificial Sequence
<220> FEATURE:
<223> OTHER INFORMATION: Heavy Chain Variable Sequence

<400> SEQUENCE: 133

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Ile Arg Gln Ala Pro Gly Lys Gly Leu Glu Trp Val
            35                  40                  45

Ser Tyr Ile Asp Glu Gly Gly Gly Gln Thr Ile Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Asn Pro Phe Asp Tyr Trp Gly Gln Gly Thr Leu
            100                 105                 110

Val Thr Val Ser Ser
        115

<210> SEQ ID NO 134
<211> LENGTH: 117
<212> TYPE: PRT
<213> ORGANISM: Artificial Sequence
<220> FEATURE:
<223> OTHER INFORMATION: Heavy Chain Variable Sequence

<400> SEQUENCE: 134

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Ile Arg Gln Ala Pro Gly Lys Gly Leu Glu Trp Val
            35                  40                  45

Ser Tyr Ile Asp Ala Gly Gly Phe Thr Ile Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Asn Pro Phe Asp Tyr Trp Gly Gln Gly Thr Leu
            100                 105                 110

Val Thr Val Ser Ser
        115

<210> SEQ ID NO 135
<211> LENGTH: 117
<212> TYPE: PRT
<213> ORGANISM: Artificial Sequence
<220> FEATURE:
<223> OTHER INFORMATION: Heavy Chain Variable Sequence

<400> SEQUENCE: 135

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Ile Arg Gln Ala Pro Gly Lys Gly Leu Glu Trp Val
        35                  40                  45

Ser His Ile Asp Ala Gly Gly Arg Thr Trp Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Asn Pro Phe Asp Tyr Trp Gly Gln Gly Thr Leu
            100                 105                 110

Val Thr Val Ser Ser
        115

<210> SEQ ID NO 136
<211> LENGTH: 117
<212> TYPE: PRT
<213> ORGANISM: Artificial Sequence
<220> FEATURE:
<223> OTHER INFORMATION: Heavy Chain Variable Sequence

<400> SEQUENCE: 136

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Ile Arg Gln Ala Pro Gly Lys Gly Leu Glu Trp Val
        35                  40                  45

Ser His Ile Ala Thr Gly Gly Asn Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Asn Pro Phe Asp Tyr Trp Gly Gln Gly Thr Leu
            100                 105                 110

Val Thr Val Ser Ser
        115

<210> SEQ ID NO 137

```
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Leu Pro Trp Thr Phe Gly Gln Gly Thr Lys Val Glu Ile Lys
            100                 105                 110

<210> SEQ ID NO 138
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Ser Phe Met His Trp Tyr Gln Gln Lys Pro Gly Lys Ala Pro
        35                  40                  45

Lys Leu Leu Ile Tyr Val Gly Ser Arg Leu Asp Tyr Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Leu Pro Trp Thr Phe Gly Gln Gly Thr Lys Val Glu Ile Lys
            100                 105                 110

<210> SEQ ID NO 139
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser His Val
            20                  25                  30

Arg Trp Ser Phe Met His Trp Tyr Gln Gln Lys Pro Gly Lys Ala Pro
        35                  40                  45
```

```
Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Leu Pro Trp Thr Phe Gly Gln Gly Thr Lys Val Glu Ile Lys
                100                 105                 110

<210> SEQ ID NO 140
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
                20                  25                  30

Gly Tyr Ser Phe Met His Trp Tyr Gln Gln Lys Pro Gly Lys Ala Pro
            35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln His Ser Arg
                85                  90                  95

Glu Leu Pro Trp Thr Phe Gly Gln Gly Thr Lys Val Glu Ile Lys
                100                 105                 110

<210> SEQ ID NO 141
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Ala Trp
                20                  25                  30

Gly Tyr Ser Phe Met His Trp Tyr Gln Gln Lys Pro Gly Lys Ala Pro
            35                  40                  45

Lys Leu Leu Ile Tyr Val Ala Ser Arg Leu Glu Ser Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln His Ser Arg
                85                  90                  95

Glu Leu Pro Trp Thr Phe Gly Gln Gly Thr Lys Val Glu Ile Lys
                100                 105                 110

<210> SEQ ID NO 142
<211> LENGTH: 111
<212> TYPE: PRT
<213> ORGANISM: Artificial Sequence
```

```
<220> FEATURE:
<223> OTHER INFORMATION: Light Chain Variable Sequence

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser His Val
            20                  25                  30

Arg Trp Ser Phe Met His Trp Tyr Gln Gln Lys Pro Gly Lys Ala Pro
        35                  40                  45

Lys Leu Leu Ile Tyr Leu Ala Ser Lys Leu Glu Ser Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln His Ser Arg
                85                  90                  95

Glu Leu Pro Trp Thr Phe Gly Gln Gly Thr Lys Val Glu Ile Lys
            100                 105                 110

<210> SEQ ID NO 143
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Glu Gly
            20                  25                  30

Arg Trp Ser Phe Met His Trp Tyr Gln Gln Lys Pro Gly Lys Ala Pro
        35                  40                  45

Lys Leu Leu Ile Tyr Val Ala Ser Arg Leu Glu Ser Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln His Ser Arg
                85                  90                  95

Glu Leu Pro Trp Thr Phe Gly Gln Gly Thr Lys Val Glu Ile Lys
            100                 105                 110

<210> SEQ ID NO 144
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Leu Asp
            20                  25                  30

Arg Trp Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60
```

```
Arg Phe Ser Gly Ser Gly Ser Gly Thr Asp Phe Thr Phe Thr Ile Ser
 65                  70                  75                  80

Ser Leu Gln Pro Glu Asp Ile Ala Thr Tyr Tyr Cys Gln His Ser Arg
                 85                  90                  95

Glu Leu Pro Trp Thr Phe Gly Gln Gly Thr Lys Val Glu Ile Lys
                100                 105                 110
```

<210> SEQ ID NO 145
<211> LENGTH: 117
<212> TYPE: PRT
<213> ORGANISM: Artificial Sequence
<220> FEATURE:
<223> OTHER INFORMATION: Heavy Chain Variable Sequence

<400> SEQUENCE: 145

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Thr Met Ser Trp Val Arg Gln Ala Pro Gly Lys Gly Leu Glu Trp Val
             35                  40                  45

Ser Tyr Ile Ser Ser Gly Gly Asn Thr Tyr Tyr Pro Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Arg Gly Asn Pro Phe Asp Tyr Trp Gly Gln Gly Thr Leu
                100                 105                 110

Val Thr Val Ser Ser
            115
```

<210> SEQ ID NO 146
<211> LENGTH: 117
<212> TYPE: PRT
<213> ORGANISM: Artificial Sequence
<220> FEATURE:
<223> OTHER INFORMATION: Heavy Chain Variable Sequence

<400> SEQUENCE: 146

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Thr Met Ser Trp Val Arg Gln Ala Pro Gly Lys Gly Leu Glu Trp Val
             35                  40                  45

Ser Ala Ile Asp His Gly Gly Arg Thr Tyr Tyr Pro Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Arg Gly Asn Pro Phe Asp Tyr Trp Gly Gln Gly Thr Leu
                100                 105                 110

Val Thr Val Ser Ser
            115
```

<210> SEQ ID NO 147

```
<211> LENGTH: 117
<212> TYPE: PRT
<213> ORGANISM: Artificial Sequence
<220> FEATURE:
<223> OTHER INFORMATION: Heavy Chain Variable Sequence

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Ala Ile Asp Gly Gly Gly Ala Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Asn Pro Phe Asp Tyr Trp Gly Gln Gly Thr Leu
            100                 105                 110

Val Thr Val Ser Ser
            115

<210> SEQ ID NO 148
<211> LENGTH: 111
<212> TYPE: PRT
<213> ORGANISM: Artificial Sequence
<220> FEATURE:
<223> OTHER INFORMATION: Light Chain Variable Sequence

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Tyr Val
            20                  25                  30

Arg Trp Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Leu Pro Trp Thr Phe Gly Gln Gly Thr Lys Val Glu Ile Lys
            100                 105                 110

<210> SEQ ID NO 149
<211> LENGTH: 240
<212> TYPE: PRT
<213> ORGANISM: Homo sapiens

<400> SEQUENCE: 149

Thr Pro Ala Pro Lys Ser Cys Pro Glu Arg His Tyr Trp Ala Gln Gly
1               5                   10                  15

Lys Leu Cys Cys Gln Met Cys Glu Pro Gly Thr Phe Leu Val Lys Asp
            20                  25                  30

Cys Asp Gln His Arg Lys Ala Ala Gln Cys Asp Pro Cys Ile Pro Gly
        35                  40                  45
```

```
Val Ser Phe Ser Pro Asp His His Thr Arg Pro His Cys Glu Ser Cys
 50                  55                  60

Arg His Cys Asn Ser Gly Leu Leu Val Arg Asn Cys Thr Ile Thr Ala
 65                  70                  75                  80

Asn Ala Glu Cys Ala Cys Arg Asn Gly Trp Gln Cys Arg Asp Lys Glu
                 85                  90                  95

Cys Thr Glu Cys Asp Pro Leu Pro Asn Pro Ser Leu Thr Ala Arg Ser
                100                 105                 110

Ser Gln Ala Leu Ser Pro His Pro Gln Pro Thr His Leu Pro Tyr Val
            115                 120                 125

Ser Glu Met Leu Glu Ala Arg Thr Ala Gly His Met Gln Thr Leu Ala
130                 135                 140

Asp Phe Arg Gln Leu Pro Ala Arg Thr Leu Ser Thr His Trp Pro Pro
145                 150                 155                 160

Gln Arg Ser Leu Cys Ser Ser Asp Phe Ile Arg Ile Leu Val Ile Phe
                165                 170                 175

Ser Gly Met Phe Leu Val Phe Thr Leu Ala Gly Ala Leu Phe Leu His
            180                 185                 190

Gln Arg Arg Lys Tyr Arg Ser Asn Lys Gly Glu Ser Pro Val Glu Pro
            195                 200                 205

Ala Glu Pro Cys Arg Tyr Ser Cys Pro Arg Glu Glu Glu Gly Ser Thr
210                 215                 220

Ile Pro Ile Gln Glu Asp Tyr Arg Lys Pro Glu Pro Ala Cys Ser Pro
225                 230                 235                 240

<210> SEQ ID NO 150
<211> LENGTH: 193
<212> TYPE: PRT
<213> ORGANISM: Homo sapiens

<400> SEQUENCE: 150

Met Pro Glu Glu Gly Ser Gly Cys Ser Val Arg Arg Arg Pro Tyr Gly
 1               5                  10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
             35                  40                  45

Pro Leu Glu Ser Leu Gly Trp Asp Val Ala Glu Leu Gln Leu Asn His
 50                  55                  60

Thr Gly Pro Gln Gln Asp Pro Arg Leu Tyr Trp Gln Gly Gly Pro Ala
 65                  70                  75                  80

Leu Gly Arg Ser Phe Leu His Gly Pro Glu Leu Asp Lys Gly Gln Leu
                 85                  90                  95

Arg Ile His Arg Asp Gly Ile Tyr Met Val His Ile Gln Val Thr Leu
                100                 105                 110

Ala Ile Cys Ser Ser Thr Thr Ala Ser Arg His His Pro Thr Thr Leu
            115                 120                 125

Ala Val Gly Ile Cys Ser Pro Ala Ser Arg Ser Ile Ser Leu Leu Arg
130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
```

Pro

<210> SEQ ID NO 151
<211> LENGTH: 12
<212> TYPE: PRT
<213> ORGANISM: Artificial Sequence
<220> FEATURE:
<223> OTHER INFORMATION: CDR Heavy Chain Variable Sequence
<220> FEATURE:
<221> NAME/KEY: Xaa can be any naturally occurring amino acid
<222> LOCATION: (3)..(3)
<220> FEATURE:
<221> NAME/KEY: Xaa can be any naturally occurring amino acid
<222> LOCATION: (4)..(4)
<220> FEATURE:
<221> NAME/KEY: Xaa can be any naturally occurring amino acid
<222> LOCATION: (5)..(5)
<220> FEATURE:
<221> NAME/KEY: Xaa can be any naturally occurring amino acid
<222> LOCATION: (7)..(7)
<220> FEATURE:
<221> NAME/KEY: Xaa can be any naturally occurring amino acid
<222> LOCATION: (10)..(10)
<220> FEATURE:
<221> NAME/KEY: Xaa can be any naturally occurring amino acid
<222> LOCATION: (12)..(12)

<400> SEQUENCE: 151

Arg Ile Xaa Xaa Xaa Asp Xaa Asp Thr Xaa Tyr Xaa
1               5                   10

<210> SEQ ID NO 152
<211> LENGTH: 17
<212> TYPE: PRT
<213> ORGANISM: Artificial Sequence
<220> FEATURE:
<223> OTHER INFORMATION: CDR Heavy Chain Variable Sequence
<220> FEATURE:
<221> NAME/KEY: Xaa can be any naturally occurring amino acid
<222> LOCATION: (4)..(4)
<220> FEATURE:
<221> NAME/KEY: Xaa can be any naturally occurring amino acid
<222> LOCATION: (7)..(7)
<220> FEATURE:
<221> NAME/KEY: Xaa can be any naturally occurring amino acid
<222> LOCATION: (12)..(12)
<220> FEATURE:
<221> NAME/KEY: Xaa can be any naturally occurring amino acid
<222> LOCATION: (13)..(13)

<400> SEQUENCE: 152

Arg Ile Tyr Xaa Gly Asp Xaa Asp Thr Asn Tyr Xaa Xaa Lys Phe Lys
1               5                   10                  15

Gly

<210> SEQ ID NO 153
<211> LENGTH: 13
<212> TYPE: PRT
<213> ORGANISM: Artificial Sequence
<220> FEATURE:
<223> OTHER INFORMATION: CDR Light Chain Variable Sequence
<220> FEATURE:
<221> NAME/KEY: Xaa can be any naturally occurring amino acid
<222> LOCATION: (8)..(8)
<220> FEATURE:
<221> NAME/KEY: Xaa can be any naturally occurring amino acid
<222> LOCATION: (11)..(11)
<220> FEATURE:
<221> NAME/KEY: Xaa can be any naturally occurring amino acid
<222> LOCATION: (13)..(13)

```
<400> SEQUENCE: 153

Lys Ala Ser Gln Ser Val Asp Xaa Ala Gly Xaa Ser Xaa
1               5                   10

<210> SEQ ID NO 154
<211> LENGTH: 7
<212> TYPE: PRT
<213> ORGANISM: Artificial Sequence
<220> FEATURE:
<223> OTHER INFORMATION: CDR Light Chain Variable Sequence
<220> FEATURE:
<221> NAME/KEY: Xaa can be any naturally occurring amino acid
<222> LOCATION: (1)..(1)

<400> SEQUENCE: 154

Xaa Ala Ser Asn Leu Glu Ser
1               5

<210> SEQ ID NO 155
<211> LENGTH: 16
<212> TYPE: PRT
<213> ORGANISM: Artificial Sequence
<220> FEATURE:
<223> OTHER INFORMATION: CDR Light Chain Variable Sequence
<220> FEATURE:
<221> NAME/KEY: Xaa can be any naturally occurring amino acid
<222> LOCATION: (9)..(9)
<220> FEATURE:
<221> NAME/KEY: Xaa can be any naturally occurring amino acid
<222> LOCATION: (10)..(10)
<220> FEATURE:
<221> NAME/KEY: Xaa can be any naturally occurring amino acid
<222> LOCATION: (11)..(11)
<220> FEATURE:
<221> NAME/KEY: Xaa can be any naturally occurring amino acid
<222> LOCATION: (14)..(14)

<400> SEQUENCE: 155

Lys Ala Ser Gln Ser Val Asp Tyr Xaa Xaa Xaa Met Ser Xaa Met Asn
1               5                   10                  15

<210> SEQ ID NO 156
<211> LENGTH: 17
<212> TYPE: PRT
<213> ORGANISM: Artificial Sequence
<220> FEATURE:
<223> OTHER INFORMATION: CDR Heavy Chain Variable Sequence
<220> FEATURE:
<221> NAME/KEY: Xaa can be any naturally occurring amino acid
<222> LOCATION: (1)..(1)
<220> FEATURE:
<221> NAME/KEY: Xaa can be any naturally occurring amino acid
<222> LOCATION: (3)..(3)
<220> FEATURE:
<221> NAME/KEY: Xaa can be any naturally occurring amino acid
<222> LOCATION: (4)..(4)
<220> FEATURE:
<221> NAME/KEY: Xaa can be any naturally occurring amino acid
<222> LOCATION: (8)..(8)
<220> FEATURE:
<221> NAME/KEY: Xaa can be any naturally occurring amino acid
<222> LOCATION: (10)..(10)

<400> SEQUENCE: 156

Xaa Ile Xaa Xaa Gly Gly Gly Xaa Thr Xaa Tyr Pro Asp Ser Val Lys
1               5                   10                  15
Gly

<210> SEQ ID NO 157
<211> LENGTH: 17
```

```
<212> TYPE: PRT
<213> ORGANISM: Artificial Sequence
<220> FEATURE:
<223> OTHER INFORMATION: CDR Heavy Chain Variable Sequence
<220> FEATURE:
<221> NAME/KEY: Xaa can be any naturally occurring amino acid
<222> LOCATION: (1)..(1)
<220> FEATURE:
<221> NAME/KEY: Xaa can be any naturally occurring amino acid
<222> LOCATION: (3)..(3)
<220> FEATURE:
<221> NAME/KEY: Xaa can be any naturally occurring amino acid
<222> LOCATION: (4)..(4)
<220> FEATURE:
<221> NAME/KEY: Xaa can be any naturally occurring amino acid
<222> LOCATION: (8)..(8)
<220> FEATURE:
<221> NAME/KEY: Xaa can be any naturally occurring amino acid
<222> LOCATION: (10)..(10)

<400> SEQUENCE: 157

Xaa Ile Xaa Xaa Gly Gly Gly Xaa Thr Xaa Tyr Pro Asp Ser Val Lys
1               5                   10                  15

Gly

<210> SEQ ID NO 158
<211> LENGTH: 15
<212> TYPE: PRT
<213> ORGANISM: Artificial Sequence
<220> FEATURE:
<223> OTHER INFORMATION: CDR Light Chain Variable Sequence
<220> FEATURE:
<221> NAME/KEY: Xaa can be any naturally occurring amino acid
<222> LOCATION: (8)..(8)
<220> FEATURE:
<221> NAME/KEY: Xaa can be any naturally occurring amino acid
<222> LOCATION: (9)..(9)
<220> FEATURE:
<221> NAME/KEY: Xaa can be any naturally occurring amino acid
<222> LOCATION: (10)..(10)
<220> FEATURE:
<221> NAME/KEY: Xaa can be any naturally occurring amino acid
<222> LOCATION: (11)..(11)

<400> SEQUENCE: 158

Arg Ala Ser Lys Ser Val Ser Xaa Xaa Xaa Xaa Ser Phe Met His
1               5                   10                  15

<210> SEQ ID NO 159
<211> LENGTH: 327
<212> TYPE: PRT
<213> ORGANISM: Artificial Sequence
<220> FEATURE:
<223> OTHER INFORMATION: Heavy Chain Constant Region

<400> SEQUENCE: 159

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95
```

Arg Val Glu Ser Lys Tyr Gly Pro Pro Cys Pro Pro Cys Pro Ala Pro
                100                 105                 110

Glu Ala Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 160
<211> LENGTH: 107
<212> TYPE: PRT
<213> ORGANISM: Artificial Sequence
<220> FEATURE:
<223> OTHER INFORMATION: Light Chain Constant Region

<400> SEQUENCE: 160

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 161

```
<211> LENGTH: 5
<212> TYPE: PRT
<213> ORGANISM: Artificial Sequence
<220> FEATURE:
<223> OTHER INFORMATION: CDR Heavy Chain Variable Sequence

<400> SEQUENCE: 161

Ser Tyr Gly Met Ser
1               5

<210> SEQ ID NO 162
<211> LENGTH: 11
<212> TYPE: PRT
<213> ORGANISM: Artificial Sequence
<220> FEATURE:
<223> OTHER INFORMATION: CDR Heavy Chain Variable Sequence

<400> SEQUENCE: 162

Ala Asp Tyr Tyr Gly Asp Tyr Gly Phe Gly Tyr
1               5                   10

<210> SEQ ID NO 163
<211> LENGTH: 654
<212> TYPE: DNA
<213> ORGANISM: Artificial Sequence
<220> FEATURE:
<223> OTHER INFORMATION: Antibody Light Chain Sequence

<400> SEQUENCE: 163
gacatccaga tgacccagag ccccagcagc ctgagcgcca gcgtgggcga ccgggtgacc      60
atcacctgcc gggccagcaa gagcgtgagc gaggggcgat ggagcttcat gcactggtac     120
cagcagaagc ccggcaaggc ccccaagctg ctgatctacg tggccagcag actggagagc     180
ggcgtgccca gccggttcag cggcagcggc agcggcaccg acttcacctt caccatcagc     240
agcctgcagc ccgaggacat cgccacctac tactgccagc acagccggga gctgcccctgg    300 accttcggcc agggcaccaa ggtggagatc aagcgtacgg tggctgcacc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc     600 acccatcagg gcctgagctc gcccgtcaca aagagcttca caggggaga gtgt           654

<210> SEQ ID NO 164
<211> LENGTH: 1332
<212> TYPE: DNA
<213> ORGANISM: Artificial Sequence
<220> FEATURE:
<223> OTHER INFORMATION: Antibody Heavy Chain Sequence

<400> SEQUENCE: 164
caggtgcagc tggtggagag cggcggcggc ctggtgaagc ccggcggcag cctgcggctg      60
agctgcgccg ccagcggctt caccttcagc agctacggga tgagctggat ccggcaggcc    120
cccggcaagg gcctggagtg ggtgagctac atcgatgagg gcggcggcca gaccatctac    180
cccgacagcg tgaagggccg gttcaccatc agccgggaca cgccaagaa cagcctgtac    240 ctgcagatga acagcctgcg ggccgaggac accgccgtgt actactgcgc ccggcaccgg    300 ggcaaccccct cgactactg gggccagggc accctggtga ccgtgagcag cgcttccacc    360
aagggcccat ccgtcttccc cctggcgccc tgctccagga gcacctccga gagcacagcc    420
```

```
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacgaaaac ctacacctgc    600
aacgtagatc acaagcccag caacaccaag gtggacaaga gagttgagtc caaatatggt    660
cccccatgcc caccatgccc agcacctgag gccgccgggg gaccatcagt cttcctgttc    720
cccccaaaac ccaaggacac tctcatgatc tcccggaccc ctgaggtcac gtgcgtggtg    780
gtggacgtga gccaggaaga ccccgaggtc cagttcaact ggtacgtgga tggcgtggag    840
gtgcataatg ccaagacaaa gccgcgggag gagcagttca acagcacgta ccgtgtggtc    900
agcgtcctca ccgtcctgca ccaggactgg ctgaacggca aggagtacaa gtgcaaggtc    960
tccaacaaag gcctcccgtc ctccatcgag aaaaccatct ccaaagccaa agggcagccc   1020
cgagagccac aggtgtacac cctgccccca tcccaggagg agatgaccaa gaaccaggtc   1080
agcctgacct gcctggtcaa aggcttctac cccagcgaca tcgccgtgga gtgggagagc   1140
aatgggcagc cggagaacaa ctacaagacc acgcctcccg tgctggactc cgacggctcc   1200
ttcttcctct acagcaggct aaccgtggac aagagcaggt ggcaggaggg gaatgtcttc   1260
tcatgctccg tgatgcatga ggctctgcac aaccactaca cacagaagag cctctccctg   1320
tctctgggta aa                                                       1332
```

```
<210> SEQ ID NO 165
<211> LENGTH: 17
<212> TYPE: PRT
<213> ORGANISM: Artificial Sequence
<220> FEATURE:
<223> OTHER INFORMATION: CDR Heavy Variable Sequence

<400> SEQUENCE: 165

Arg Ile Tyr Ala Gly Asp Gly Asp Thr Asn Tyr Ser Pro Ser Phe Gln
1               5                   10                  15
Gly

<210> SEQ ID NO 166
<211> LENGTH: 17
<212> TYPE: PRT
<213> ORGANISM: Artificial Sequence
<220> FEATURE:
<223> OTHER INFORMATION: CDR Heavy Variable Sequence

<400> SEQUENCE: 166

Arg Ile Tyr Ala Gly Asp Gly Asp Thr Ala Tyr Ser Pro Ser Phe Gln
1               5                   10                  15
Gly

<210> SEQ ID NO 167
<211> LENGTH: 17
<212> TYPE: PRT
<213> ORGANISM: Artificial Sequence
<220> FEATURE:
<223> OTHER INFORMATION: CDR Heavy Variable Sequence

<400> SEQUENCE: 167

Arg Ile Tyr Ala Gly Asp Gly Asp Thr Asn Tyr Ala Pro Ser Phe Gln
1               5                   10                  15
Gly
```

```
<210> SEQ ID NO 168
<211> LENGTH: 17
<212> TYPE: PRT
<213> ORGANISM: Artificial Sequence
<220> FEATURE:
<223> OTHER INFORMATION: CDR Heavy Variable Sequence

<400> SEQUENCE: 168

Arg Ile Tyr Ala Gly Asp Ala Asp Thr Ala Tyr Ser Pro Ser Phe Gln
1               5                   10                  15

Gly

<210> SEQ ID NO 169
<211> LENGTH: 17
<212> TYPE: PRT
<213> ORGANISM: Artificial Sequence
<220> FEATURE:
<223> OTHER INFORMATION: CDR Heavy Variable Sequence

<400> SEQUENCE: 169

Arg Ile Tyr Ala Gly Asp Ala Asp Thr Asn Tyr Ala Pro Ser Phe Gln
1               5                   10                  15

Gly

<210> SEQ ID NO 170
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 170

Lys Ala Ser Gln Ser Val Asp Tyr Phe Ser Glu Ser Phe Met Asn
1               5                   10                  15

<210> SEQ ID NO 171
<211> LENGTH: 7
<212> TYPE: PRT
<213> ORGANISM: Artificial Sequence
<220> FEATURE:
<223> OTHER INFORMATION: CDR Light Chain Variable Sequence
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be any naturally occurring amino acid

<400> SEQUENCE: 171

Xaa Ala Ser Xaa Leu Glu Ser
1               5

<210> SEQ ID NO 172
<211> LENGTH: 15
<212> TYPE: PRT
<213> ORGANISM: Artificial Sequence
<220> FEATURE:
<223> OTHER INFORMATION: CDR Light Chain Variable Sequence

<400> SEQUENCE: 172

Arg Ala Ser Lys Ser Val Ser Leu Ile Arg Trp Ser Phe Met His
1               5                   10                  15

<210> SEQ ID NO 173
<211> LENGTH: 7
```

```
<212> TYPE: PRT
<213> ORGANISM: Artificial Sequence
<220> FEATURE:
<223> OTHER INFORMATION: CDR Light Chain Variable Sequence

<400> SEQUENCE: 173

Val Ala Asp Arg Val Glu Val
1               5

<210> SEQ ID NO 174
<211> LENGTH: 179
<212> TYPE: PRT
<213> ORGANISM: Homo sapiens

<400> SEQUENCE: 174

Thr Pro Ala Pro Lys Ser Cys Pro Glu Arg His Tyr Trp Ala Gln Gly
1               5                   10                  15

Lys Leu Cys Cys Gln Met Cys Glu Pro Gly Thr Phe Leu Val Lys Asp
                20                  25                  30

Cys Asp Gln His Arg Lys Ala Ala Gln Cys Asp Pro Cys Ile Pro Gly
            35                  40                  45

Val Ser Phe Ser Pro Asp His His Thr Arg Pro His Cys Glu Ser Cys
        50                  55                  60

Arg His Cys Asn Ser Gly Leu Leu Val Arg Asn Cys Thr Ile Thr Ala
65                  70                  75                  80

Asn Ala Glu Cys Ala Cys Arg Asn Gly Trp Gln Cys Arg Asp Lys Glu
                85                  90                  95

Cys Thr Glu Cys Asp Pro Leu Pro Asn Pro Ser Leu Thr Ala Arg Ser
            100                 105                 110

Ser Gln Ala Leu Ser Pro His Pro Gln Pro Thr His Leu Pro Tyr Val
        115                 120                 125

Ser Glu Met Leu Glu Ala Arg Thr Ala Gly His Met Gln Thr Leu Ala
    130                 135                 140

Asp Phe Arg Gln Leu Pro Ala Arg Thr Leu Ser Thr His Trp Pro Pro
145                 150                 155                 160

Gln Arg Ser Leu Cys Ser Ser Asp Phe Ile Arg Ile Leu His His His
                165                 170                 175

His His His

<210> SEQ ID NO 175
<211> LENGTH: 135
<212> TYPE: PRT
<213> ORGANISM: Homo sapiens

<400> SEQUENCE: 175

Thr Pro Ala Pro Lys Ser Cys Pro Glu Arg His Tyr Trp Ala Gln Gly
1               5                   10                  15

Lys Leu Cys Cys Gln Met Cys Glu Pro Gly Thr Phe Leu Val Lys Asp
                20                  25                  30

Cys Asp Gln His Arg Lys Ala Ala Gln Cys Asp Pro Cys Ile Pro Gly
            35                  40                  45

Val Ser Phe Ser Pro Asp His His Thr Arg Pro His Cys Glu Ser Cys
        50                  55                  60

Arg His Cys Asn Ser Gly Leu Leu Val Arg Asn Cys Thr Ile Thr Ala
65                  70                  75                  80

Asn Ala Glu Cys Ala Cys Arg Asn Gly Trp Gln Cys Arg Asp Lys Glu
                85                  90                  95
```

```
Cys Thr Glu Cys Asp Pro Leu Pro Asn Pro Ser Leu Thr Ala Arg Ser
                100                 105                 110

Ser Gln Ala Leu Ser Pro His Pro Gln Leu Glu Val Leu Phe Gln Gly
        115                 120                 125

Pro His His His His His
        130             135

<210> SEQ ID NO 176
<211> LENGTH: 107
<212> TYPE: PRT
<213> ORGANISM: Homo sapiens

<400> SEQUENCE: 176

Thr Pro Ala Pro Lys Ser Cys Pro Glu Arg His Tyr Trp Ala Gln Gly
1               5                   10                  15

Lys Leu Cys Cys Gln Met Cys Glu Pro Gly Thr Phe Leu Val Lys Asp
            20                  25                  30

Cys Asp Gln His Arg Lys Ala Ala Gln Cys Asp Pro Cys Ile Pro Gly
            35                  40                  45

Val Ser Phe Ser Pro Asp His His Thr Arg Pro His Cys Glu Ser Cys
        50                  55                  60

Arg His Cys Asn Ser Gly Leu Leu Val Arg Asn Cys Thr Ile Thr Ala
65                  70                  75                  80

Asn Ala Glu Cys Ala Cys Arg Asn Gly Trp Gln Cys Arg Asp Lys Glu
                85                  90                  95

Cys Thr Glu Cys Asp Gly Gly His His His His
                100                 105
```